United States Patent [19]
Zychlinsky et al.

[11] Patent Number: 5,972,899
[45] Date of Patent: Oct. 26, 1999

[54] APOPTOSIS INDUCED BY SHIGELLA IPAB

[75] Inventors: Arturo Zychlinsky, New York; Yajing Chen, Elmhurst, both of N.Y.

[73] Assignee: New York University, New York, N.Y.

[21] Appl. No.: 08/591,079

[22] Filed: Jan. 25, 1996

[51] Int. Cl.⁶ .......................... A61K 48/00; C12N 15/31; C12N 15/85

[52] U.S. Cl. ........................ 514/44; 424/93.2; 435/320.1; 435/455

[58] Field of Search .......................... 514/46; 435/320.1, 435/240.2, 172.3, 69.1, 455, 325; 424/93.1, 93.2; 536/23.5; 935/47

[56] References Cited

FOREIGN PATENT DOCUMENTS 9416060   7/1994   WIPO .
WO 94/16060   7/1994   WIPO .

OTHER PUBLICATIONS

Baudry, B. et al., "Localization of Plasmid Loci Necessary for the Entry of *Shigella flexneri* into HeLa Cells, and Characterization of One Locus Enconding Four Immunogenic Polypeptides" *J. Gen. Microbiol.* 133:3403–3413 (1987).

Baudry, B. et al., "Nucleotide sequence of the invasion plasmid antigen B and C genes (ipaB and ipaC) of *Shigella flexneri*" *Microb. Pathogenesis* 4:345–357 (1988).

Berkner, K., et al. "Development of Adenovirus Vectors for the Expression of Heterologous Genes" *BioTechniques* 6:616–629 (1988).

Boyd, J. .M. et al., "Adenovirus E1B 19kDa and Bcl–2 Proteins Interact with a Common Set of Cellular Proteins," *Cell* 79:341 (1994).

Bursch, W. et al., "Cell death by apoptosis and its protective role against disease" *Trends Pharmacol.* Sci. 13:245 (1992).

Buysse, J. M. et al. "Molecular Cloning of Invasion Plasmid Antigen (ipa) Genes from *Shigella flexneri*: Analysis of ipa Gene Products and Genetic Mapping" *J. Bacteriol.* 169:2561–2569 (1987).

Chander, R. et al. Artificial Viral Envelopes Containing Recombinant Human Immunodeficiency Virus (HIV) gp¹⁶⁰ *Life Sci.* (1992) 504:481–489.

Clem, R. J. et al., "Prevention of Apoptosis by a Baculovirus Gene During Infection of Insect Cells" *Science* 254:1388 (1991).

Clem, R. J. et al., "Control of Programmed Cell Death by the Baculovirus Genes p35 and iap" *Molec. Cell. Biol.* 14:5212 (1994).

Datta, R., et al., "Ionizing radiation activates transcription of the EGR1 gene via CArG elements" *Proc. Natl. Acad. Sci. USA* (1992) 89:10149–10153.

Dixit, M., "Construction and expression of a recombinant adeno–associated virus that harbors a human β–globin–encoding cDNA" *Gene* 104:253–257 (1991).

Farhood, H. et al., "Cationic Liposomes for Direct Gene Transfer in Therapy of Cancer and Other Diseases" *Ann NY Acad. Sci.* (1994) 716:23–35.

Felgner, P.L., et al., "Lipoection: A Highly Efficient, Lipid–Mediated DNA–Transfection Procedure"; *Proc. Natl. Acad. Sci. U.S.A.*; (1987)vol. 84, No. 21, pp. 7413–7417.

Geller, A.I., et al., A Defective HSV–1 Vector Expresses *Escherichia coli* β–Galactosidase in Cultured Peripheral Neurons:, *Am. Ass. for the Adv. of Sci.* (1988) pp. 1667–1669.

Hakansson, S. et al., "YopB and YopD Constitute a Novel Class of Yersinia Yop Proteins" *Infect. Immun.* 61:71–80 (1993).

Hallahan, D.C., et al. "Spatial and temporal control of gene therapy using ionizing radiation" *Nature Med.* (1995) 1:786–791.

Henderson, S. et al., "Epstein–Barr virus–coded BHRF1 protein, a viral homologue of Bcl–2, protects human B cells from programmed cell death" *Proc. Natl. Acad. Sci. USA* 90:8479 (1993).

Hermant, D. et. al., "Functional conservation of the Salmonella and Shigella effectors of entry into epithelial cells" *Mol. Microbiol.* 17:781–789 (1995).

High, N. et al., "IpaB of *Shigella flexneri* causes entry into epithelial cells and escape from the phagocytic vacuole" *EMBO J.* 12:1191–1999 (1992).

Huber, B.E., et al., "Gene Therapy for Neoplastic Diseases"; *Ann. of the NY Aca of Sci* (1994), pp. 23–35.

(List continued on next page.)

*Primary Examiner*—Scott D. Priebe
*Attorney, Agent, or Firm*—Shmuel Livnat Rader Fishman & Grauer

[57] ABSTRACT

Shigella IpaB protein or functional derivative binds to interleukin-1β-converting enzyme (ICE) or an ICE homologue and activates a program of apoptosis. DNA encoding the Shigella IpaB protein, the IpaB protein or a functional derivative thereof is provided to a eukaryotic, preferably human, cell to induce apoptosis of that cell. This approach useful in treating diseases or disorders treatable by the eradication of unwanted cells, including cancer, autoimmunity, inflammation and chronic viral infections. Protein or peptide molecules (and the DNA coding therefor) which act as competitive antagonists for ICE binding without activating the apoptosis program are useful in treating or preventing diseases which involve an apoptotic mechanisms in their pathogenesis, for example AIDS, degenerative diseases such as Alzheimer's disease, myelodysplastic disorders, ischemic injuries or toxin-induced liver diseases. Various methods of gene therapy relying upon controlled expression of IpaB in a target cell are disclosed. Also provided are methods for: inhibiting the interaction of an apoptosis-inducing protein or peptide with ICE, detecting a compound capable of inhibiting the binding of IpaB to ICE or to an ICE homologue, screening a candidate protein or peptide for its ability to interact with IpaB in a cell, isolating from a complex mixture a compound capable of binding to IpaB protein

20 Claims, 5 Drawing Sheets

OTHER PUBLICATIONS

Kaniga, K. et al., "Homologs of the Shigella IpaB and OpaC Invasins Are Required for *Salmonella typhimurium* Entry into Cultured Epithelial Cells" *J. Bacteriol.* 177: 3965–3971 (1995).

LaBrec, E. H. et al., "Epithelial Cell Penetration as an Essential Step in the Pathogenesis of Bacillary Dysentery" *J. Bacteriol.* 88:1503–1518 (1964).

Mannino, R. J., et al. "Liposome Mediated Gene Transfer" *BioTechniques* 6:682–690 (1988).

McGrory, W.J., et al., "Short Communications: A Simple Technique for the Rescue of Early Region I Mutations into Infectious Human Adenovirus Type 5"; *Virology* (1988) 163:614–617.

Menard, R. et al., "Nonpolar Mutagenesis of the ipa Genes Defines IpaB, IpaC, and IpaD as Effectors of *Shigella flexneri* Entry into Epithelial Cells" *J. Bacteriol.* 175:5899–5906 (1993).

Miura, M. et al., "Induction of Apoptosis in Fibroblasts by IL–1β–Converting Enzyme, a Mammalian Homolog of the *C. elegans* Cell Death Gene ced–3" *Cell* 75:653–660 (1993).

Miller, A.D., et al., "Current Topics in Microbiology 158 and Immunology" *Retroviral Vectors* (1992) 158:2–24.

Morishita, R. et al., "Novel in Virto Gene Transfer Method for Study of Local Modulators in Vascular Smooth Muscel Cells"; *American Heart Association*: Hypertension (1993) 21:894899.

Moss, B., et al., "Poxvirus Vectors: cytoplasmic expression of transferred genes" *Current Opinion in Genetics and Development* 3:86–90 (1993).

Neilan, J.G. et al., "An African Swine Fever Virus Gene with Similarity to the Proto–Oncogene bcl–2 and the Epstein–Barr Virus Gene BHRF1" *J. Virol.* 67:4391–4394 (1993).

Nicolau, C., et al., "In Vivo Expression of Rat Insulin After Intravenous Administration of the Liposome–Entrapped Gene for Rat Insulin I"; *Proc. of the Nat. Aca. of Sci.* (1983) 80:1068–1072.

Ohi, S., et al., "Construction and Replication of an Adeno–Associated Virus Expression Vector That Contains Human β–Globin cDNA"; *Gene*: An International Journal Focusing on Gene Cloning and gene Structure and Function (1990) 89:279–282.

Rao, L. et al., "The adenovirus E1A proteins induce apoptosis, which is inhibited by the E1B 19–kDa and Bcl–2 proteins," *Proc. Natl. Acad. Sci. USA* 89:7742–7746 (1992).

Ray, C. A. et al., "Viral Inhibition of Inflammation: Cowpox Virus Encodes an Inhibitor of the Interleukin–1β Converting Enzyme", *Cell* 69:597–604 (1992).

Samulski, R.J., et al., "Targeted Integration of Adeno–Associated Virus (AAV) into Human Chromosome 19"; *The Embo Journal* (1991) 10:3941–3950.

Sansonetti, P.J. et al., "Role of Interleukin–1 in the Pathogenesis of Experimental Shigellosis" *J. Clin. Inv.* (1995) 96:884–892.

Schreier H. et al. "(Patho)physiologic Pathways to Drug Targeting: Artificial Viral Envelopes" *J. Mol. Recognit.* (1995) 8:59–62.

Sells, M. A., et al., "Delivery of Protein in Cells Using Polycationic" *Short Technical Reports* 19:72–78 (1995).

Sizemore, D.R. et al., "Attenuated Shigella as a DNA Delivery Vehicle for DNA–Mediated Immunization" *Science* (1995) 270:299–302.

Soriano, P., et al., "Targeted and Nontargeted Liposomes for In Vivo Transfer to Rat Liver Cells of a Plasmid Containing the Preproinsulin I Gene" *Proc. Natl. Aca. of Sci.* (1983) 80:7128–7131.

Spencer, D.M. et al., "Controlling Signal Transduction with Synthetic Ligands" *Science* (1993) 262:1019–1024.

Straus, S.E., "Adenovirus Infections in Humans"; *The Adenoviruses*, pp. 451–496.

Thompson, C. B., "Apoptosis in the Pathogenesis and Treatment of Disease", *Science* 267:1456–1462 (1995).

Tomita, N., et al., "Direct in Vivo Gene Introduction Into Rat Kidney"; *Biochemical and Biophysical Research Communications* (1992) 186:129–134.

Vaux, G. et al., "An Evolutionary Perspective on Apoptosis, "*Cell* 76:777–779 (1994).

Vilk et al. (1995) "Targeted Gene Therapy", FASEB J. 9:190–199.

Wu, C.H., et al., "Targeting Genes: Delivery and Persistent Expression of a Foreign Gene Driven by Mammalian Regulatory Elements in Vivo", *The Journal of Biological Chemistry*, 264:1698516987.

Zychlinsky, A. et al., "IpaB mediates macrophage apoptosis induced by *Shigella felxneri,*" Molec. *Microbiol.* 11:619–627 (1994).

Zychlinsky, A. et al., "*Shigella flexneri* induces apoptosis in infected macrophages", Nature 358:167–168 (1992).

Zychlinsky, A. et al. "Interleukin 1 is Released by Murine Macrophages during Apoptosis Induced by *Shigella flexneri*" *J. Clin. Invest.* (1994) 94:1328–1332.

Orkin et al., "Report and recommendations of the panel to assess the NIH investment in research on gene therapy", issued by the U.S. National Institutes of Health, Dec. 5, 1995.

E. Marshall (1995) Science 269:1050–1055.

Vile et al (1995) "Targeted Gene Therapy", FASEB J. 9: 190–199.

Cook et al (1994) Cancer Biotherapy 9: 131–141.

APOPTOSIS INDUCED BY SHIGELLA IPAB

BACKGROUND OF THE INVENTION

1. Field of the Invention

The invention in the fields of molecular biology and medicine relates to methods for inducing controlled cell death or apoptosis in a eukaryotic cell by providing either DNA encoding the Shigella IpaB protein or the IpaB protein to the cell. This method is useful in treating diseases or disorders treatable by the eradication of unwanted cells, for example cancer, autoimmunity, inflammation and chronic viral infections.

2. Description of the Background Art

Apoptosis, or programmed cell death, is considered an essential process in normal development of multicellular organisms. Apoptosis is also thought to serve as a defense against viral infection and oncogenesis (Thompson, C. B., Science 267:1456–1462 (1995)).

A number of activators or inducers of apoptosis are listed in Table I, below. (See also Thompson, supra.). Diseases which are associated with either induction or inhibition of apoptosis are listed in Table II, below.

Cellular and certain viral genes act as inhibitors of apoptosis. The best known cellular "death repressor" gene, bcl2, was first discovered in human tumor cells. This gene can replace the structurally similar adenoviral elb gene (Rao, L. et al., Proc. Natl. Acad. Sci. USA 89:7742 (1992)) as an inhibitor of apoptosis (Boyd, J. M. et al., Cell 79:341 (1994)). Other genes which are similar in sequence and function to bcl2 are the bhrf1 gene of Epstein-Barr virus (EBV) and the lmw5-hl gene of African swine fever virus (Neilan, J. G., et al, J. Virol. 67:4391 (1993), Henderson, S. et al., Proc. Natl. Acad. Sci. USA 90:8479 (1993)). Other structurally dissimilar genes that inhibit

TABLE I

INDUCERS OF APOPTOSIS

| Physiological Activators | Damage-Related Inducers, Drugs and Toxins |
|---|---|
| TNF family (Fas ligand, TNF) | Viral infections, Bacterial toxins, |
| TGFβ | Oncogenes (myc, rel, E1A) |
| Neurotransmitters (glutamate, | Tumor Suppressors (p53) |
| dopamine, NMDA) | Cytotoxic T lymphocytes |
| Withdrawal of growth factors, | Oxidants and free radicals |
| nutrient deprivation | Heat shock |
| Loss of matrix attachment | Chemotherapeutic drugs |
| Calcium | (antimetabolites) |
| Glucocorticoids | Gamma and UV irradiation |
|  | Ethanol |
|  | β-amyloid peptides |

TABLE II

Diseases Associated with Induction or Inhibition of Apoptotic Cell Death

| Inhibition of Apoptosis | Increased Apoptosis |
|---|---|
| 1. Cancer | 1. AIDS |
| Carcinomas with p53 mutations | 2. Neurodegenerative disorders |
| Follicular | Alzheimer's disease |
| lymphomas | Parkinson's disease |
| Hormone-dependent tumors | Amyotrophic lateral sclerosis |
| Breast cancer | Retinitis pigmentosa |
| Prostate cancer | Cerebellar degeneration |
| Ovarian cancer | 3. Myelodysplastic syndromes |
| 2. Autoimmune disorders | Aplastic anemia |

TABLE II-continued

Diseases Associated with Induction or Inhibition of Apoptotic Cell Death

| Inhibition of Apoptosis | Increased Apoptosis |
|---|---|
| Systemic lupus erythematosus | 4. Ischemic injury |
| Immune glomerulonephritis | Myocardial infarction |
| 3. Viral infections | Stroke |
| Herpesviruses | Reperfusion injury |
| Poxviruses | 5. Toxin-induced liver diseases |
| Adenoviruses | Alcoholism | apoptosis include the p35 gene and the iap gene in baculoviruses ((Clem, R. J. et al., Science 254:1388 (1991); Molec. Cell Biol. 14:5212 (1994)); cowpox virus crmA (Ray, C. A. et al., Cell 69:597 91992)), Herpesvirus K1.34.5.

A central death effector molecule in the apoptosis pathway is the cysteine protease interleukin-1β-converting enzyme (ICE). This enzyme was first discovered based on its cleavage of IL-1β precursor protein to mature active IL-1β. ICE therefore plays a crucial role in the initiation of cytokine cascades involved in inflammatory and host defense responses. ICE is closely related to the protein encoded by the Caenorhabditis elegans cell death gene, ced-3, the product of which is required for cells to undergo programmed cell death during development (M. Miura et al., Cell 75:653 (1993)). The important role of ICE in apoptosis is supported by the observations that a number of the viral inhibitors of apoptosis are specific inhibitors of ICE.

Recent evidence suggests that the failure of cells to undergo apoptotic cell death might be involved in the pathogenesis of a variety of human diseases, including cancer, autoimmune diseases, and viral infections (Vaux, G. et al., Cell 76:777 (1994); Bursch, W. et al., Trends Pharmacol Sci. 13:245 (1992)). In contrast, a large number of diseases characterized by cell loss, including neurodegenerative disorders, AIDS (acquired immunodeficiency syndrome), and osteoporosis, may result from accelerated rates of physiologic cell death. Hence, the art recognizes the need for specific methods designed to enhance or decrease the susceptibility of individual cell types to apoptosis as a basis for treating a variety of human diseases. It is to this problem that the present invention is addressed.

Apoptosis Induced by Shigella Bacteria

Shigella, the etiological agent of dysentery, kills macrophages by inducing apoptosis. After being phagocytosed by a macrophage, Shigella flexneri cells escape from the phagosome into the cytoplasm and induce apoptosis both in vitro (Zychlinsky, A. et al., Nature 358:167–168 (1992)) and in vivo. S. flexneri invasiveness and cytotoxicity are encoded in a 220 kb plasmid (LaBrec, E. H. et al., J. Bacteriol. 88:1503–1518 (1964)) which includes among many other genes the ipa operon. The gene products IpaB, C and D are essential for cell invasion (Menard, R. et al., J. Bacteriol. 175:5899–5906 (1993); High, N. et al., EMBO J. 12:1191–1999(1992)). However, Ipab is required to initiate apoptosis. This was shown by using an ipaB deletion mutant which lacked invasiveness (Zychlinsky, A., et al. Molec. Microbiol. 11:619–627 (1994)). In the absence of ipaB, apoptosis does not occur. IpaB and its neighboring genes of the Shigella invasion plasmid have been cloned and characterized (Buysse, J. M. et al., J. Bacteriol. 169:2561–2569 (1987; Baudry, B. et al., J. Gen. Microbiol. 133:3403–3413 (1987); Baudry, B. et al., Microb. Pathogenesis 4:345–357 (1988)). The nucleotide sequence (SEQ ID NO:1) of ipaB and the amino acid sequence of the IpaB protein (SEQ ID NO:2) are provided below. However, the ability of IpaB alone to induce apoptosis upon delivery to a target cell as an isolated gene or protein has not previously been known and is the subject matter of the present invention.

Homologues of IpaB have been found in other bacterial species. These include yopB of *Yersinia enterocolitica* and *Yersinia pseudotuberculosis* (Hakansson, S. et al., *Infect. Immun.* 61:71–80 (1993)), sipB in *Salmonella typhimurium* (Kaniga, K. et al., *J. Bacteriol* 177:3965–3971 (1995) and in *Salmonella typhi* (Hermant, D. et al., *Mol. Microbial* 17:781–789 (1995)). The complete nucleotide sequences encoding these four IpaB homologues are SEQ ID NO:3, 5, 7 and 9, respectively. The amino acid sequences of these four homologues are SEQ ID NO:4, 6, 8 and 10, respectively.

SUMMARY OF THE INVENTION

The present inventors discovered that the Shigella IpaB protein binds to ICE in a eukaryotic cell and activates a program of apoptosis without the need for any other bacteria-derived gene product and that this finding could be used to kill undesired cells in a subject, particularly neoplastic cells.

The present invention is directed to a method of inducing apoptosis in a eukaryotic cell thereby killing the cell, comprising:

(a) providing to a cell to be killed a DNA molecule in expressible form which encodes the Shigella IpaB protein or a functional derivative of the IpaB protein, wherein the DNA molecule is substantially free of sequences encoding other proteins with which IpaB is natively associated; and (b) causing the DNA molecule to be expressed in the cell, thereby producing the IpaB protein or derivative which induces apoptosis and kills the cell.

The DNA molecule above preferably encodes the IpaB protein, more preferably SEQ ID NO:1. A preferred functional derivative is a homologue of the IpaB protein from a genus other than Shigella, including but not limited to *Yersinia enterocolitica* yopB, *Yersinia pseudotuberculosis* yopB, *Salmonella typhimurium* sipB and *Salmonella typhi* sipB. The functional derivative may also be a fusion protein of IpaB or a fusion protein of an apoptosis-inducing fragment of IpaB.

In a preferred embodiment of the above method, the DNA, in the form of a vector, preferably a viral vector, is provided to the cell in a live animal. The DNA molecule may be an expression plasmid encoding a fusion protein of IpaB and glutathione-S-transferase. The viral vector may be a retroviral vector, an adenoviral vector, an adeno-associated viral vector, a herpes viral vector or a vaccinia viral vector.

In other embodiments of the above method, the DNA is provided by liposome-mediated gene transfer or by artificial viral envelope.

The cell to be targeted in the above method is any cell undergoing unwanted proliferation, preferably a tumor cell or an activated lymphocyte mediating an autoimmune response. Also included is a virus-infected cell.

The present invention also provides a method of inducing apoptosis in, and killing, a eukaryotic cell, comprising delivering to a cell to be killed a composition which includes an effective amount of IpaB protein, preferably isolated, or a functional derivative thereof The protein preferably has the amino acid sequence SEQ ID NO:2.

In this method, the functional derivative is preferably a homologue of the IpaB protein from a genus other than Shigella, including but not limited to *Yersinia enterocolitica* yopB, *Yersinia pseudotuberculosis* yopB, *Salmonella typhimurium* sipB and *Salmonella typhi* sipB. The functional derivative may also be a fusion protein of IpaB or a fusion protein of an apoptosis-inducing fragment of IpaB.

In the above method, the composition is preferably delivered by microinjecting the composition into the cell, lipofecting the cell with a cationic lipid preparation or administering an artificial viral envelope containing the composition.

The target cell for the above method is any cell undergoing unwanted proliferation such as a tumor cell or an activated lymphocyte mediating an autoimmune response. Also included is a virus-infected cell.

The present invention is further directed to a method for removing undesired cells in a subject having a disease or disorder associated with the presence of undesired cells, comprising inducing apoptosis in the undesired cells in the subject using any of the above methods, thereby removing the cells. The diseases or disorders included in this invention include, but are not limited to, cancer, benign hyperplasia, atherosclerosis, autoimmunity, or chronic viral infection.

Also provided is a method of inhibiting the interaction of an apoptosis-inducing protein or peptide with ICE in a cell, comprising providing to the cell in which the apoptosis-inducing protein or peptide is expressed an effective amount of an ICE-binding IpaB fragment or derivative which fragment or derivative does not itself induce apoptosis.

The present invention includes a method for detecting in a chemical or biological sample a compound capable of inhibiting the binding of IpaB to ICE or to an ICE homologue, the method comprising:

(a) contacting the sample with a solid support on which is immobilized
  i. Ipab or an ICE-binding portion or derivative thereof, or
  ii. ICE, an ICE homologue or an lpaB-binding portion of ICE or of the ICE homologue,
in the presence of:
  (1) soluble IpaB or an ICE-binding portion of IpaB when the ICE, ICE homologue or Ipab-binding portion is immobilized, or
  (2) soluble ICE, an ICE homologue or an IpaB-binding portion of ICE or the ICE homologue, when the IpaB or and ICE-binding portion is immobilized;

(b) measuring the binding of ICE to the IpaB-immobilizing solid support or the binding of IpaB to the ICE-immobilizing or ICE homologue-immobilizing solid support (c) comparing the binding measured in step (b) to the binding of ICE to the to the IpaB-immobilizing solid support or the binding of IpaB to the ICE-immobilizing or ICE homologue-immobilizing solid support in the absence of the sample, wherein a lower measurable binding in step (b) as compared to step (c) detects the compound.

Also provided is a method for screening a candidate protein or peptide for its ability to interact with IpaB in a cell, comprising:

(a) producing a first plasmid which comprises DNA encoding IpaB linked to DNA encoding the DNA-binding domain of GAL4, such that expression of the first plasmid DNA results in a IpaB-GAL4 DNA binding domain fusion protein;

(b) producing a second plasmid which comprises DNA encoding the candidate protein or peptide linked to DNA encoding the transcriptional activation domain of GAL4 such that expression of the second plasmid DNA results in a fusion protein of the candidate protein or peptide and the GAL4 activation domain, wherein the first plasmid and the second plasmid are capable of transforming yeast cells, (c) transforming a yeast cell which includes a reporter gene having an upstream GAL4 binding site, wherein the expression of the reporter gene requires the action of an intact GAL4 transcriptional activator composed of a DNA-binding domain and an activation domain;

(d) measuring or detecting expression of the reporter gene, wherein expression of the reporter gene indicates that the candidate protein interacts with IpaB protein in the cell.

Another embodiment is directed to a method for detecting in a biological sample the presence of a compound which inhibits the apoptosis-inducing action of IpaB in cells, comprising (a) delivering to the cells an apoptosis-inducing amount of an isolated IpaB protein or a functional derivative thereof, (b) delivering the cells the biological sample; and (c) measuring apoptosis in the cells in comparison with control cells which have not been treated with the sample, wherein inhibition of apoptosis in the presence of the sample compared to the apoptosis induced in the absence of the sample indicates the presence of the compound.

Also provided is a method for isolating from a complex mixture a compound capable of binding to IpaB protein, comprising:

(a) immobilizing IpaB protein, or a compound-binding portion thereof, to a solid support;

(b) contacting the complex mixture with the immobilized IpaB protein, or portion thereof, allowing the compound to bind, and washing away any unbound material; and (c) eluting the bound compound from the solid support, thereby isolating the compound.

In another embodiment, the present invention is directed to a method of treating a subject having shigellosis comprising administering to the subject an effective amount of (a) an IpaB analogue or competitive antagonist which binds to ICE and inhibits the binding of active IpaB and, thereby, the induction of apoptosis by IpaB, or (b) an ICE inhibitor such as Ac-YVAD-CHO (see below), a functional derivative of the YVAD tetrapeptide any other peptide or peptide analogue or derivative that binds to the active site of ICE and inhibits ICE action leading to apoptosis.

BRIEF DESCRIPTION OF THE DRAWINGS

FIG. 1 shows the affinity purification of IpaB-binding proteins from J774 cells. J774 cells were metabolically labeled with $^{35}$S-methionine and lysed. The cell lysate was incubated with Glutathione-Sepharose beads coupled with either GST (lane 1) or GST-IpaB (lane 2). The proteins bound to the beads were resolved on 5–15% gradient SDS-PAGE. Four bands, indicated with arrows and their apparent molecular weight, bound specifically to IpaB.

FIG. 2 shows western blotting analysis of GST (lane 1) and GST-IpaB (lane 2) affinity purified proteins and J774 lysate (lane 3) resolved on 5–18% SDS-PAGE with rabbit anti-mouse Interleukin 1β converting enzyme (ICE) antiserum (provided by Dr. M. J. Tocci, Merck). Three of the four proteins identified by affinity purification were immunoreactive with the anti-ICE antibody. There was also a nonspecific band of around 30 kDa.

FIG. 3 shows western blot analysis with an ICE serum of proteins co-immunoprecipitated with an anti-IpaB mAb from BS176-(lane 1) or M90T-(Lane 2) infected J774 cells. Both P10 and P20 were co-immunoprecipitated with IpaB from shigella infected macrophages, indicating that in vivo IpaB binds the mature form of ICE.

FIG. 5 shows cytotoxicity assayed by release of lactate dehydrogenase (LDH) 2 h after infection of J774 cells with M90T in the presence or absence of an ICE inhibitor.

FIG. 6 shows the cleavage of IL-1β in peritoneal macrophages (lane 1), macrophages infected with M90T (lane 2), macrophages treated with ICE inhibitor and then infected with M90T (lane 3).

DESCRIPTION OF THE PREFERRED EMBODIMENTS

Figure 1:
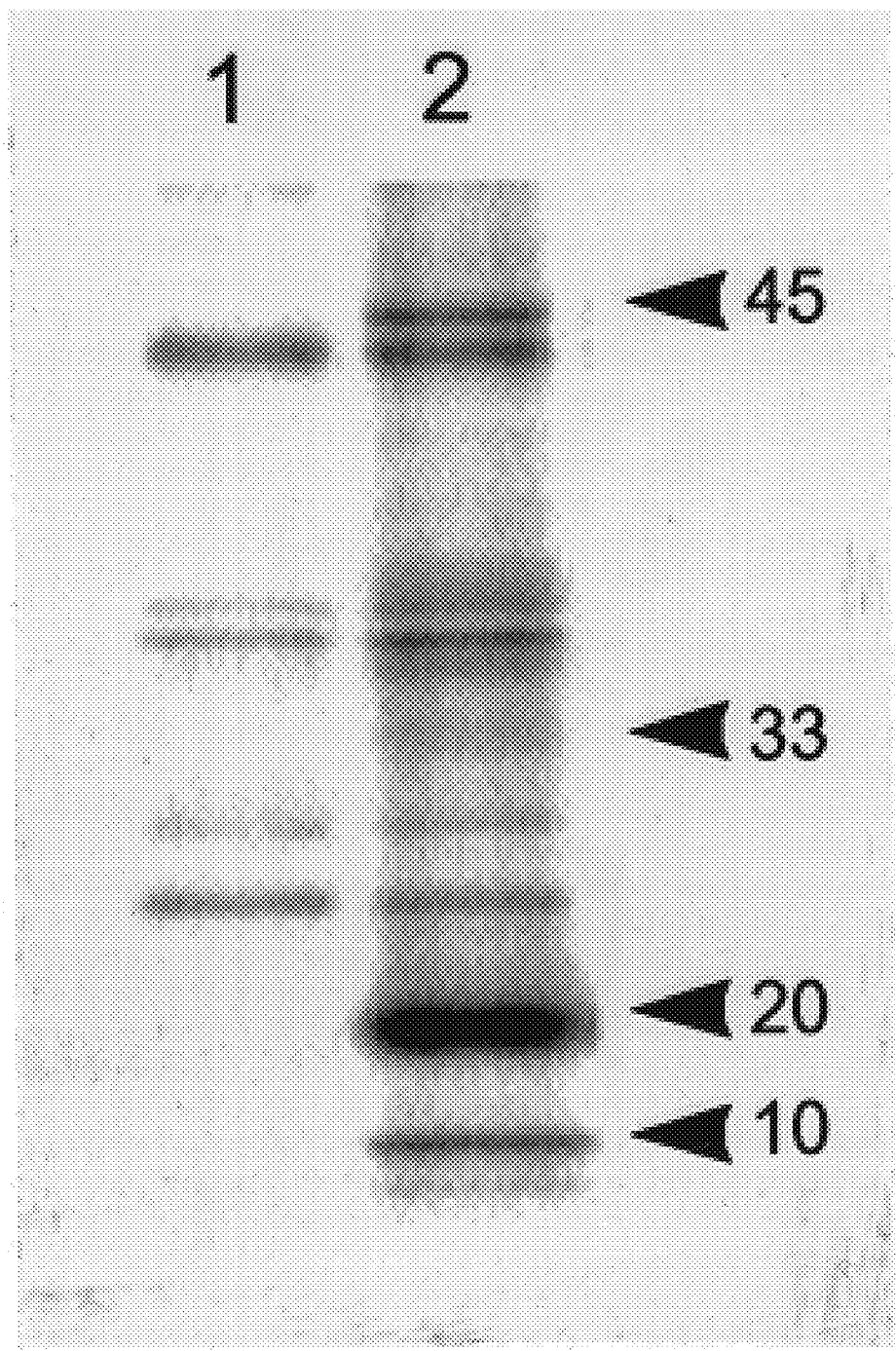
FIGS. 1–3 show results of studies which identify macrophage IpaB-binding proteins.

The present inventors are the first to discover that a bacterial protein alone induces apoptosis in mammalian cells by direct interaction with the target cell's death program. In terms of the pathophysiology of bacterial infection and the host response to such infection, this discovery suggests a dual role for Shigella induced apoptosis in macrophages mediated by ICE activation: (1) bacterial evasion of macrophage killing, and (2) concomitant release of mature IL-1β (Zychlinsky, A. et al., *J. Clin.Invest.* 94:1328–1332 (1994)), which elicits the inflammation characteristic of dysentery (Sansonetti, P. J. et al., *J. Clin. Inv.* 96:884–892 (1995)). These findings highlight the convergent role of the bi-functional ICE as a proinflammatory and a cell death molecule. The isolated Ipab protein is the first known activator of ICE which acts as a proximal trigger of the ICE-initiated apoptotic process.

The present invention is directed to a method for inducing apoptosis in a eukaryotic cell by providing to that cell a DNA molecule encoding Ipab or encoding a peptide thereof which induces apoptosis in the cell. In another embodiment, the present invention is directed to a method of inducing apoptosis in a eukaryotic cell by providing to that cell the IpaB protein or an apoptosis-inducing functional derivative thereof When the IpaB-encoding DNA molecule, and the protein or peptide encoded thereby, are expressed in the cell, apoptosis is induced, and the cells undergoes programmed cell death.

The present invention is based on the unexpected discovery that the ipaB gene derived from the virulence plasmid of Shigella bacteria is independently capable of inducing apoptosis in the absence of any other Shigella gene. Thus, in the methods of the present invention, DNA which encodes the IpaB protein or that portion of IpaB which has the apoptosis-inducing activity is provided to cells to activate the apoptosis machinery and kill the cells.

The preparation of various of these DNA molecules is done using methods well known in the art. Methods of expressing these DNA molecules in the target cell to induce apoptosis employ any of a number of plasmid vectors which include the ipaB DNA in expressible form.

In addition, an alternative approach to inducing apoptosis utilizes the direct administration to a eukaryotic cell of the Ipab protein, or a functional derivative thereof which is able to bind and activate ICE, thereby activating the apoptosis program in the cell.

The compositions and methods described herein are useful for killing any type of cell in vitro and in vivo, and are of particular utility for the treatment of a tumor or an autoimmune process in an animal. However, the teachings provided herein will allow the skilled artisan to induce apoptosis in, and thereby kill, any targeted cell. For example, it is possible to kill cells which have been transfected with a retroviral vector and introduced into a subject to achieve gene therapy once the survival of these cells is no longer desired.

In another embodiment, the ability of IpaB to bind to ICE is exploited in a method to inhibit apoptosis. Here an ICE-binding functional derivative of IpaB which lacks the apoptosis-inducing activity ("competitive antagonists" discussed below) is provided to a cell to inhibit apoptosis caused by endogenous or exogenous stimuli.

An effective amount or dose of (a) Ipab or a functional derivative for inducing apoptosis in a cell, (b) an ICE-binding IpaB fragment or derivative which fragment or derivative does not itself induce apoptosis (for inhibiting apoptosis) or (c) an inhibitor of ICE such as a chemically modified YVAD peptide, is in the range of about 0.01 femtogram to about 1 picogram per cell. Effective doses may be determined, preferably by injecting cells in vitro, in order to identify the optimal dose range using various of the methods described herein. The dosage administered will in part be dependent upon the health and weight of the recipient, the existence of other concurrent treatment, if any, frequency of treatment, and the nature of the effect desired, for example, eradication of a tumor or treatment of autoimmunity.

Administration of DNA or a vector or other vehicle containing the DNA, as in the gene therapy embodiments described herein, is performed using any of a number of routes, depending on the location of the cells being targeted. Thus, administration may be by any parenteral route, including but not limited to intramuscular, subcutaneous or transdermal, intravenous (including into the portal circulation), intrathecal, intraperitoneal, intragastric and by inhalation or instillation into the lungs. Oral administration of certain of the delivery vehicles disclosed herein is also known in the art.

The present invention is particularly directed to the treatment of disorders associated with increased cell survival. Diseases characterized by the accumulation of cells include cancer, autoinmmune diseases, and certain viral illnesses as well as benign hyperplasia and vascular restenosis. Cell accumulation can result from either increased proliferation or the failure of cells to undergo apoptosis in response to appropriate stimuli (Table I, above). Alterations in the control of cell survival are important in the pathogenesis of these so-called proliferative disorders.

Cells from a wide variety of human malignancies have a decreased ability to undergo apoptosis in response to at least some physiologic stimuli (Hoffman, B. et al., *Oncogene* 9:1807 (1994)), in particular in metastatic tumors. Recent advances are beginning to shed some light on the molecular bases for the increased resistance of tumor cells to undergo apoptosis is under intense scrutiny by investigators in the field. Several genes that are critical in the regulation of apoptosis are known. bcl2 is one member of a family of genes that can control the apoptotic threshold of a cell (Boise, L. H. et al., *Cell* 74:597 (1993); E. Y. Lin et al., *J. Immunol.* 151:1979 (1993); K. M. Kozopas et al., *Proc. Natl. Acad. Sci. USA* 90: 3516 (1993); Z. N. Oltvai e al., *Cell* 74:609 (1993)). Five homologues of bcl-2 have been described. Overexpression of bcl2 or of the related gene bclx confers resistance to cell death in response to chemotherapeutic agents (T. Ohmon et al., *Biochem. Biophys. Res. Commun.* 192:30 (1993)). The primary mechanism by which most chemotherapeutic agents induce cell death is by altering cell physiology leading to the induction of apoptosis. Cell death in response to DNA damage by these or other agents typically results from apoptosis. Thus, the use of IpaB to induce apoptosis, as disclosed herein, provides a novel form of chemotherapeutic intervention against cancer.

Another therapeutic target of the present invention is autoimmune disease. Proper regulation of cell death is essential for eliminating potentially autoreactive lymphocytes during development and for removing excess cells after the completion of an immune response. Failure to remove autoinmmune cells that arise during development or that develop as a result of somatic mutation during an immune response can result in autoimmune disease. Dysregulated apoptosis is central to the etiology of autoimmune diseases. One molecule critical in regulating cell death in lymphocytes is the cell surface receptor Fas (Watanabe-Fukunaga et al., *Nature* 356:314 (1992)). Stimulation of Fas on activated lymphocytes induces apoptosis and acts by activation of ICE, the target of IpaB according to the present invention. bcl-2 blocks fas-mediated cell death (Itoh, N. et al., *J. Immunol.* 151:621–627 (1993) by inhibiting the action of ICE. Two forms of hereditary autoimmune disease are attributed to alterations in Fas-mediated apoptosis (Watanabe-Fukunaga, supra; T. Suda et al., *Cell* 75:1169 (1993)).

Treatment of cells with IpaB to induce apoptosis and cell death, as described herein. is therefore useful in arresting the progression of autoimmune diseases such as systemic lupus erythematosus, rheumatoid arthritis, psoriasis, inflammatory bowel disease, and autoimmune diabetes mellitus, just to name a few. Altered susceptibility of lymphocytes to death by apoptosis has been reported in several of these diseases (J. D. Mountz et al., *J. Immunol.* 152:3685 (1994)).

The present invention is also useful in the treatment of virus infections. The disruption of cell physiology following viral infection can cause an infected cell to undergo apoptosis (B. Levine et al., *Nature* 361:739 (1993)). The suicide of an infected cell or its lysis by specific cytotoxic T lymphocytes are both cellular defense mechanism to prevent viral propagation. T cells can induce cell death by activating the target cell's endogenous cell death program (D. Kagieta et al., *Science* 265:528 (1994)).

Viruses can circumvent such defenses by disrupting the normal regulation of apoptosis in infected cells. For example, establishment of an adenoviral infection depends on the function of the 19 kDa E1B protein (Rao, L. et al., *Proc. Natl. Acad. Sci. USA* 89:7742 (1992)) which blocks apoptosis directly (and can be replaced in adenovirus by bcl2. Other genes with similar actions are bhrfI in EBV and lmw5hl in African swine fever virus (Neilan et al., supra) as well as the p35 gene and the inhibitor of apoptosis gene (AP) in baculoviruses (Clem et al., supra). p35 inhibits apoptosis independently, without requiring expression of any other viral proteins. Poxviruses appear to inhibit apoptosis by producing an inhibitor of ICE. The cowpox gene crmA is a member of the serpin family of protease inhibitors and acts as a specific inhibitor of ICE (C. A. Ray et al., Cell 69:597 (1992)).

Thus, the IpaB protein and DNA constructs of the present invention can be used in an antiviral therapeutic approach, by introduction into cells infected with virus. This is particularly important for latent viral infection or situations in which viral replication does not lead to cell death. Indeed, the prevention of apoptosis by a virus is important for the establishment of viral latency. EBV establishes a latent infection in B cells and expresses the LAMP-I gene which specifically up-regulates the expression of bcl2, potentially providing a survival advantage to latently infected cells (Henderson et al., Cell 65:1107 (1991)). Chronic Sindbis virus infection is also dependent on the host cell's expression of bcl2 (Levine, B. et al., Nature 361:739 (1993)). According to the present invention IpaB (as protein or DNA) is introduced into chronically infected cells to overcome the anti-apoptotic action of viral genes, resulting in death of the cells and eradication of the chronic or latent infection.

Because the activation of ICE by IpaB also initiates an inflammatory process, via the release of I1-1β and the cytokine cascade which follows, the methods of the present invention may be used to treat conditions in which it is desirable to initiate or stimulate inflammation. Examples of such conditions include unresolved bacterial granulomas such as in tuberculosis or other mycobacterial infections, including leprosy. The activation of ICE leading to inflammation is beneficial for treating early or small tumors which can be eradicated in situ by macrophages activated as part of this inflammatory cascade.

Also included in the present invention are DNA and protein molecules, more specifically peptides, which act as competitive antagonists for ICE binding. Such molecules, preferably Ipab fragments, retain the capacity to bind to ICE but do not activate the apoptosis program. These agents can be used in the treatment or prevention of diseases which involve an apoptotic mechanisms in their pathogenesis, for example AIDS, degenerative diseases such as Alzheimer's disease, myelodysplastic disorders, ischemic injuries or toxin-induced liver diseases. Such IpaB fragments can be screened readily for their ICE-inhibiting activity in competition with intact IpaB or any other protein which activates ICE. Such screening methods may rely either on apoptosis or on ICE enzymatic activity as an endpoint. Alternatively, simpler binding assays may be used. Once Ipab fragments having the desired activity are identified, they are prepared either recombinantly or by peptide synthesis using methods well-known in the art. A useful IpaB fragment or derivative thereof (defined below) for use as a competitive antagonist may have any amino acid sequence provided that it shares sufficient structural similarity with IpaB that permits binding to the IpaB binding site(s) of ICE and competition with the biological action of IpaB in activating ICE.

Also useful in this regard are low molecular weight peptidomimetic compounds which influence the interactions between ICE and IpaB and stimulate ICE to initiate the apoptotic program. Such peptidomimetics may be identified by structural studies which compare the co-crystallization of ICE and IpaB in the presence or absence of a candidate peptidomimetic. Better knowledge of the stereochemistry of ICE-IpaB interactions will permit rational design of such peptidomimetic agents.

Protein-protein interactions between IpaB and ICE proteins or fragment can be analyzed in vivo using the yeast-based "two-hybrid" genetic assay, developed by Fields and coworkers ((Bartel, P. L., et al. (1993) in: Cellular Interactions in Development: A Practical Approach, D. A. Hartley, ed., Oxford University Press, Oxford, pp. 153+179; Chien, C. T. et al. (1991) Proc. Natl. Acad. Sci. USA 88:9578+9582; Fields, S. et al., 1989, Nature 340:245–247; Fritz, C. C. et al., Current. Biol. 2:403–405; Guarente, L., 1993, Proc. Natl. Acad. Sci. USA 90:1639–1541). This method is described in more detail in CLONTECHECHniques (January 1995 and July 1995 issues), which references are incorporated by reference in their entirety). One advantage of this method is that it enables not only identification of interacting proteins, but also results in the immediate availability of the cloned genes for these proteins. In addition, the two-hybrid method often detects weak and transient interactions. Neither purified target proteins nor antibodies are required. The assay is performed in vivo, so that the proteins being tested are more likely to be in their native conformations. The two-hybrid method can be used to determine if two known proteins (for which corresponding genes have been cloned) interact. Once two proteins have been shown to interact, further analysis pinpoints the regions that are directly involved in the interaction (Luban, J. et al., 1993, 73:1067–1078; Li, B. et al. (1993) FASEB J. 7:957+963; Iwabuchi, K. et al., 1993, Oncogene 8:1693–1696; Vojtek, A. et al., 1993, Cell 94:205)). Another important application of the two-hybrid method is to identify previously unknown proteins that interact with a target protein.

The two-hybrid method uses the restoration of transcriptional activation to indicate the interaction between two proteins. The yeast GAL4 transcriptional activator, for example, contains a DNA-binding domain (DNA-BD) and a transcriptional activation domain (AD) (Ma, J. et al., (1987) Cell 55:443+446). Two different cloning vectors are used to generate separate fusions of these GAL4 domains to genes encoding proteins that potentially interact with each other. The recombinant hybrid proteins are coexpressed in yeast reporter strains and are targeted to the yeast nucleus. If the target- and candidate-protein portions of the two hybrids interact with each other, the DNA-BD will be tethered to its AD. Thus, as a result of a two-hybrid interaction, the GAL4 transcriptional activator will be functionally reconstituted and will activate transcription of reporter genes (i.e., lacZ or HIS3) having upstream GAL4 binding sites. This makes the protein interaction phenotypically detectable. The Clontech MATCHMAKER® "Two-Hybrid System" (and "System 2") takes advantage of the ability of domains to assemble in vivo. Sequences encoding the two functional domains of the GAL4 transcriptional activator have been cloned into two expression vectors (pGBT9 and pGAD424 in one system; Bartel et al., supra). The pGBT9 (or the pAS2-1) vector is used to generate a fusion of the GAL4 DNA-BD and a target protein X, such as IpaB or ICE. The pGAD424 (or pACT2) vector is used to generate a fusion of the GAL4 AD and a target protein Y (such as ICE or IpaB, depending on the choice of protein X). An entire library of hybrids with the activation domain can also be constructed to search for new or unknown proteins that interact with IpaB or ICE. When interaction occurs between the IpaB or ICE and a candidate interacting protein, the two GAL4 transcription factor domains (for DNA-BD and the AD) are brought together and produce functional restoration of transcriptional activation. The two hybrids are cotransformed into a yeast host strain with a reporter gene (e.g., lacZ or HIS3) containing upstream GAL4 binding sites (GAL1 UAS); transcription of the reporter gene, which may be observed visually, indicates interaction between the candidate protein and the target protein (e.g., IpaB or ICE). This assay has been used successfully to detect various types of protein-protein interactions with non-yeast proteins as well, as listed below

| Protein X (target protein) | Protein Y (library-encoded protein) | Reference |
| --- | --- | --- |
| TNFR | TNFR | 1 |
| TNFR | TNFR | 2 |
| p40$^{phox}$ | p47$^{phox}$, p67$^{phox}$ | 3 |
| XPA | RPA | 4 |
| PPAR | PPRE | 5 |
| TOR | FKBP12 + Rapamycin | 6 |
| FAS/APO1 | MORT1* | 7 |
| FAS/APO1 | FAP-1* | 8 |
| TNFR | TRAP-1* | 9 |
| TNFR | TRAF-1*, TRAF-2* | 10 |
| CDK6 | p18* | 11 |

*Interaction first discovered using this system.
References:
1. Boldin, M. P. et al. (1995) J. Biol. Chem. 270: 387–391;
2. Song, H. Y. et al. (1994) J. Biol Chem. 270: 3574–3581;
3. Fuchs, A. et al. (1995) J. Biol. Chem. 270: 5695–5697;
4. Matsuda, T. et al. (1995) J. Biol. Chem. 270: 4152–4157;
5. Miyata, K. S. et al. (1994) Gene 148: 327–330;
6. Stan, R. et al. (1994) J. Biol. Chem. 269: 32027–32030;
7. Boldin, M. P. et al. (1995) J. Biol. Chem. 270: 7795–7798;
8. Sato, T. et al. (1995) Science 268: 411–415;
9. Song, H. Y. et al. (1995) J. Biol Chem. 270: 3574–3581;
10. Rothe, M. et al. (1994) Cell 78: 681–692;
11. Guan, K., et al. (1994) Genes Dev. 8: 2939–2952

Complete kits for identifying protein-protein interactions between two specific proteins using the two-hybrid technique are commercially available from Clontech. The MATCHMAKER Two-Hybrid System uses reconstitution of the GAL4 transcriptional activator as the basis of its assay and employs a yeast strain (SFY526 or HF7c) (Bartel, P. L. et al. (1993) Biotechniques 14:920–924; Feilutter, H. E. et al. (1994) Nucleic Acids Res. 22:1502–1503) that possesses the lacZ gene under the control of GAL4 recognition sites as the reporter system. Blue/white screening is thus used to indicate interaction between the two candidate proteins. System 2 cloning plasmids (pAS2-1 and the AD plasmid, pACT2) are high-level expression vectors, which allow detection of fusion proteins on Western blots using yeast GAL4-specific mAbs. Because of higher expression levels, System 2 would detect certain types of protein-protein interactions with greater sensitivity. The relatively lower expression levels with the original System plasmids may be advantageous when one of the hybrid proteins is toxic to the host cells.
Plasmids The DNA molecules and derivatives of the present invention may be expressed using any appropriate expression vector as is well-known in the art (Sambrook, J. et al., Molecular Cloning. A Laboratory Manual, 2nd Edition, Cold Spring Harbor Press, Cold Spring Harbor, N.Y., 1989). One useful expression vector is pGEX-KG which encodes a fusion protein between GST and IpaB. A more preferred construct comprises IpaB alone without any fusion protein partner.

More generally, a DNA molecule encoding IpaB or a derivative thereof may be recombined with vector DNA in accordance with conventional techniques, including blunt-ended or staggered-ended termini for ligation, restriction enzyme digestion to provide appropriate termini, filling in of cohesive ends as appropriate, alkaline phosphatase treatment to avoid undesirable joining, ligation with appropriate ligases, or the synthesis of fragments by the polymerase chain reaction (PCR). Techniques for such manipulations are disclosed by Sambrook, et al. (supra) and are well known in the art.

To target a particular type of cell, for example tumor cells growing in vivo, any of a number of alternate vectors which include the IpaB-encoding DNA molecules of the present invention may be selected. First, control sequences with tissue specificity for the tissue type of the target cells may be used. Examples of promoters with such specific modes of action include the insulin gene promoter for selective expression in the pancreas or the MMTV or lactalbumin promoter for expression in breast tissue.

For expression of IpaB protein or peptide or other functional derivative from the plasmids in the target cells, the endogenous translation stop codons may be utilized. If an IpaB construct having a C-terminal truncation is used in which the endogenous stop codon is lacking, a stop codon is inserted in the vector just downstream of the cloning site.

For transfection of a cell in vitro according to the present invention, a selectable marker gene (such as G418-resistance) may be added, either on the same plasmid or by contransfection using a second plasmid such as pSV2neo (Southern, P. J. et al. J Mol Appl Genet (1982) 1:327–341) or the plPB1 plasmid (Biamonti, G. et al. Nucl Acid Res (1985) 13:5547–5561). For transfection of a cell with IpaB in vivo, a selection marker useful in vivo is required, for example, the tk gene of HSV (see below).
Promoters and Enhancers A promoter is a region of a DNA or RNA molecule which is capable of binding RNA polymerase and promoting the transcription of an "operably linked" nucleic acid sequence. As used herein, a "promoter sequence" is the sequence of the promoter which is found on that strand of the DNA or RNA which is transcribed by the RNA polymerase. Two sequences of a nucleic acid molecule, such as a promoter and a coding sequence, are said to be "operably linked" when they are linked to each other in a manner which either permits both sequences to be transcribed onto the same RNA transcript, or permits an RNA transcript, begun in one sequence to be extended into the second sequence. Thus, two sequences, such as a promoter sequence and a coding sequence of DNA or RNA are operably linked if transcription commencing in the promoter sequence will produce an RNA transcript of the operably linked coding sequence. In order to be "operably linked" it is not necessary that two sequences be immediately adjacent to one another.

The promoter sequences of the present invention necessary for expression of the DNA of the invention must be functional in mammalian cells, and may be either eukaryotic or viral promoters. Suitable promoters are inducible, repressible or constitutive. An example of a preferred constitutive promoter is the viral promoter MSV-LTR, which is efficient and active in a variety of cell types, and, in contrast to most other promoters, has the same enhancing activity in arrested and growing cells. Other preferred viral promoters include that present in the CMV-LTR (from cytomegalovirus) (Bashart, M. et al., Cell 41:521 (1985)) or in the RSV-LTR (from Rous sarcoma virus) (Gorman, C. M., Proc. Natl. Acad. Sci. USA 79:6777 (1982). Also useful are the promoter of the mouse metallothionein I gene (Hamer, D., et al., J. Mol. Appl. Gen. 1:273–288 (1982)); the TK promoter of Herpes virus (McKnight, S., Cell 31:355–365 (1982)); the SV40 early promoter (Benoist, C., et al., Nature 290:304–310 (1981)); and the yeast gal4 gene promoter (Johnston, S. A., et al., Proc. Natl. Acad. Sci. (USA) 79:6971–6975 (1982); Silver, P. A., et al., Proc. Natl. Acad. Sci. (USA) 81:5951–5955 (1984)). Other illustrative descriptions of transcriptional factor association with promoter regions and the separate activation and DNA binding of transcription factors include: Keegan et al., Nature (1986)

231:699; Fields et al., *Nature* (1989) 340:245; Jones, *Cell* (1990) 61:9; Lewin, *Cell* (1990) 61:1161; Ptashne et al., *Nature* (1990) 346:329; Adams et al., *Cell* (1993) 72:306. All of the above-listed references are incorporated by reference herein. The promoter region may further include an octamer region which may also function as a tissue specific enhancer, by interacting with certain proteins found in the specific tissue. The enhancer domain of the DNA construct of the present invention is one which is specific for the target cells to be transfected, or is highly activated by cellular factors of such target cells. Examples of vectors (plasmid or retrovirus) are disclosed in (Roy-Burman et al., U.S. Pat. No. 5,112,767). For a general discussion of enhancers and their actions in transcription, see, Lewin, B. M., *Genes IV*, Oxford University Press, Oxford, (1990), pp. 552–576. Particularly useful are retroviral enhancers (e.g., viral LTR). The enhancer is preferably placed upstream from the promoter with which it interacts to stimulate gene expression. For use with retroviral vectors, the endogenous viral LTR may be rendered enhancer-less and substituted with other desired enhancer sequences which confer tissue specificity or other desirable properties such as transcriptional efficiency on the IpaB encoding DNA molecule of the present invention.

Inducible Systems for Apoptosis Induction

The utility of inducible (in contrast to constitutive) systems for inducing apoptosis is exemplified by estrogen-inducible constructs described in Braselmann, S. et al. *Proc Natl Acad Sci USA* (1993) 90:1657–1661, which reference is incorporated by reference in its entirety. Other inducible promoters well-known in the art can be used to produce analogous inducible systems for expression of the DNA molecules according to the present invention and for the induction of apoptosis in vitro or in vivo. Thus, one means for inducing apoptosis in a controllable manner is to use an IpaB DNA construct in combination with inducible or repressible control elements such as an estrogen-inducible system (Braselmann et al, supra) wherein the ipaB gene or portion thereof encoding an effective IpaB fragment is controlled by a GAL4-responsive promoter which is trans-activated in the presence of 17-β estradiol by the GAL-ER-Vp16 transcription factor, a fusion protein consisting of the DNA-binding domain of GAL4, the estrogen-binding domain of the estrogen receptor and the transactivation domain of Vp16 (of Herpes simplex virus).

For induction of expression of the IpaB DNA molecules in an estrogen-inducible system in an animal, local or systemic treatment with estrogen would be required. An effective dose of an estrogen is a dose which would trigger the expression of the IpaB DNA to induce apoptosis of cells such as tumor cells. Such doses can be ascertained by one skilled in the art. Preferably, doses in the range of about 0.05 to 100 mg/kg of an estrogen are used in a single dose or in multiple doses over a period of about one week to about 2 months, or even longer. Forms and preparations of estrogen and their usage in animals, particularly in humans, are well-known in the art (Gilman, A. G. et al., *Goodman and Gilman's The Pharmacological Basis of Therapeutics*, 7th Ed., MacMillan Publ. Co., New York, 1985). Estrogen analogs which are capable of specifically activating the exogenous transactivator while having fewer biological effects and side effects are preferred.

Another controllable system has been described by Gossen, M. et al., *Proc. Natl. Acad. Sci. USA* 89:5547–5551 (1992)) and is based on the use of control elements of the tetracycline-resistance operon encoded in Tn10 of *E. coli*. The tet repressor is fused with the activating domain of Herpes simplex virus VP16 to generate a tetracycline-controlled transactivator. Such a transactivator is used to stimulate transcription from a promoter sequence, such as the human CMV promoter IE. This is a repressible system in contrast to the estrogen-inducible system described above. A gene controlled by a promoter acting under the influence of the tetracycline-controlled transactivator can be constitutively expressed an turned off by using an effective concentration of tetracycline. Such a system can regulate a gene over about five orders of magnitude. The tetracycline-repressible system functions in vivo in mammals, where tetracycline administration via the diet is used to keep the expression of the inducible gene off. Tetracycline analogs which cross the blood-brain barrier can be used if gene activity is desired in the brain.

According to the present invention, the IpaB DNA molecule is placed under the control of a promoter subject to regulation by a tetracycline-controlled transactivator. Such a construct (in a single vector or preferably two vector form) is delivered into target cells such as tumor cells growing in vivo. To kill the tumor cells, tetracycline is withheld so that the IpaB DNA is expressed. To prevent the action of the Ipab DNA locally, tetracycline or an active congener of tetracycline is administered locally to the cells transfected with the constructs. Effective systemic doses (oral or parenteral) of tetracycline are in the range of about 0.1 mg to 1 g per day. In a preferred embodiment, the tetracycline-repressible construct is introduced into selected cells, such as cells of a particular tumor. The transactivator is maintained in the "off" position using tetracycline until the desirable localization can be demonstrated. At that time, tetracycline is withheld, stimulating expression of IpaB leading to apoptotic death of the transfected cells.

Most known approaches to gene therapy for the treatment of neoplastic or other cell proliferative diseases are not well localized. Ionizing radiation has been used to activate the transcription of exogenous genes that encode a cytotoxic protein such as TNFα (Weichselbaum, R. R. et al., *Int. J. Radiation Oncology Biol. Phys.* 24:565–567 (1992)) This may be accomplished through the use of radiation-responsive elements distal to the transcription start site of such genes. See, for example, Hallahan, D. et al. *Proc. Natl. Acad. Sci. USA* 88:2152–2160 (1991); Datta, R. et al., *Proc. Natl. Acad. Sci. USA* 89:10149–10153 (1992); Weichselbaum, R. R. et al., *Int. J. Radiation Oncol. Biol. Phys.* 24:565–567 (1992); Hallahan, D. E. et al. *J. Biol. Chem.* 268:4903–4907 (1993); Weichselbaum, R. R. et al., *Intl. J. Radiation Oncology Biol. Phys.* 30:229–234 (1994); Hallahan, D. E. et al. *Nature Med.* 1:786–791 (1995), which references are hereby incorporated by reference in their entirety. Thus, the present invention provides methods for the spatial and temporal control of gene therapy using IpaB or a functional derivative based on gene therapy with such radiation-inducible promoters to activate IpaB and thereby induce apoptosis. This method for treating neoplastic disease also takes advantage of the direct ant-tumor effects of the radiation itself, resulting in a additive or synergistic interaction between the cytotoxic action of IpaB and radiation. For treating tumor metastases, it is possible to "cone down" to metastases in one site or in multiple organs such that radiation will preferentially activate IpaB production in the irradiated volume. This approach is also applicable to local disease where radiosensitizers can be used in combination with irradiation for direct cytotoxicity and/or activation of transcription of IpaB with subsequent apoptotic tumor cell death. The present invention has advantages over the system using TNF described by Hallahan, Weichselbaum and colleagues for sparing surrounding tissue because IpaB activation intracellular. Only cells carrying the gene will be killed whereas TNFα is activated, diffuses out and acts regionally (and may even reach more distant sites where it could exert undesired toxic effects).

The ipab gene is placed in a vector under control of a radiation-inducible promoter. In one embodiment, a genetic construct with a VP-16 DNA sequence that encodes a known powerful transactivating protein attached to the DNA coding sequence derived from the DNA binding domain or the Lac repressor is inserted downstream of Cis-acting elements which bind radiation-inducible proteins. These constructs are useful in amplifying radiation-induced signals. This construct would be cotransfected with the plasmid containing multiple DNA binding sites for the Lac repressor protein cloned upstream of genes which when activated alter the phenotypic response of tumors to radiation.

In a preferred embodiment, ipaB or an active polynucleotide fragment thereof is recombined with a replication-deficient adenovirus type 5 (McGrory, et al. *Virology* 163:614–617 (1988)) to yield a vector designated Ad.Egr-ipaB (similar to the Ad.Egr-TNF vector made by GenVec, Rockville, Md, and described in Hallahan, D. E. et al., 1995, supra). This vector employs the CCA(A+T rich)$_6$GG elements (known as "CArG" elements) within the 5'-untranslated region of the early growth response (Egr-1) promoter 425 bp upstream from the transcription start site (Datta et al., supra). A control region containing the 6 CArG elements of the promoter/enhancer region of the Egr-1 gene is ligated upstream of the IpaB-encoding DNA. These control elements are known to be inducible in several types of human tumor cells. Other DNA sequences that activate transcription after X-irradiation and which may be used in the present method include AP-1 (Hallahan et al., 1993, supra) and the NKRB binding sequence (Brach, M. et al., *J. Clin. Invest.* 88:691–695 (1991)).

Tumor cells (or other cells to be treated according to the invention) are injected with or otherwise administered, on one or on multiple occasions, about $2 \times 10^8$ PFU of AD5.Egr-ipaB. At an appropriate time thereafter, ranging from several hours to several days, or even weeks, the target tissue, typically tumor, is irradiated with an effective dose of X-irradiation. The preferred radiation regimen can be determined readily by the skilled artisan using conventional clinical judgment. The dose and time course are a function of the nature and extent of disease, the particular promoter used and its responsiveness, and the treatment approach (e.g., whether the radiation is being relied upon to kill cells directly, to induce apoptosis through IpaB activation or both). In one embodiment, 5 Gy X-irradiation are given four times per week for a total of 50 Gy, for example from a Maxitron generator (1.88 Gy/min).

An advantage of the foregoing method is that transcriptional activation of a promoter is controlled by ionizing radiation within a specific body volume and for a chosen period of time. This achieves both spatial and temporal regulation of ipaB transcription allowing apoptosis to be induced at a desired time and in a desired volume of cells or tissue. Such regional radiation exposure avoids the possibility of a broader or systemic apoptosis-inducing effect. Thus, cells which have incorporated and are capable of expressing the ipaB gene but are not the intended targets of apoptosis induction are spared by excluding them from the volume being irradiated. In this manner, the radiation can be used for spatial control IpaB-mediated cell killing.

Another generally applicable method is used in conjunction with gene therapy/gene delivery methods described below, for inducing activation of a gene of interest, in particular ipaB. This method is disclosed in detail in PCT publications WO94/18317, WO95/02684 and WO95/05389; Spencer, D. M. et al., *Science* 262:1019–1024 (1993); Travis, *Science* 262:989 (1993); and *Chem. & Eng. News*, Nov. 15, 1993, pp. 55–57, which references are hereby incorporated by reference in their entirety. This approach uses intracellular protein homodimerization, heterodimerization and oligomerization in living cells into which the ipaB gene has been transfected. Chimeric responder proteins are intracellularly expressed as fusion proteins with a specific receptor domain. Treatment of the cells with a cell-permeable multivalent ligand reagent which binds to the receptor domain leads to dimerization or oligomerization of the chimeric receptor. In analogy to other chimeric receptors (see e.g. Weiss, *Cell* (1993) 73, 209), the chimeric proteins are designed such that oligomerization triggers the desired subsequent events, e.g. the propagation of an intracellular signal via subsequent protein-protein interactions and thereby the activation of a specific subset of transcription factors. The initiation of transcription can be detected using a reporter gene assay. Intracellular crosslinking of chimeric proteins by synthetic ligands allows regulation of the synthesis of IpaB and, thereby, selective induction of apoptosis.

The chimeric proteins are recombinant in that the various domains are heterologous to one another (derived from different sources not found together in nature). Recombinant DNA constructs which comprise heterologous components, e.g., encoding a particular domain or expression control sequence, which are not found directly linked to one another in nature, are used to genetically engineering target host cells in vitro or in vivo. Cells thus engineered contain at least one such chimeric protein or a first series of genetic constructs encoding the chimeric protein(s). One such DNA construct encodes a chimeric protein comprising (a) at least one receptor domain (capable of binding to a selected ligand) fused to (b) a heterologous additional ("action") protein domain. The ligand is capable of binding to two (or more) receptor domains within the chimeric proteins preferably with a Kd value ranging from $<10^{-6}$ to $<10^{-9}$ and is preferably a non-protein compound having a molecular weight $<5$ kDa. The receptor domains of the chimeric proteins so oligomerized may be the same or different. Upon exposure to the ligand and receptor oligomerization, the chimeric proteins initiate a biological process. The encoded chimeric protein may further comprises an intracellular targeting domain capable of directing the chimeric protein to a desired cellular compartment, e.g., a sequence directing the protein to associate with the nucleus.

The action domains of the chimeric proteins may be selected from a broad variety of protein domains capable of effecting a desired biological result upon oligomerization of the chimeric protein(s). For instance, the action domain may comprise a protein domain such as a CD3 ζ subunit capable, upon exposure to the ligand and subsequent oligomerization, of initiating a detectable intracellular signal; a DNA-binding protein such as Gal4; or a transcriptional activation domain such as VP16. In a preferred embodiment, the intracellular signal activates the transcription of a gene under the transcriptional control of a transcriptional control element (e.g. enhancer/promoter elements and the like) which is responsive to the oligomerization and activates expression of IpaB, leading to apoptosis. Examples of the types of ligands to which the chimeric proteins may bind include an FK506-type ligand, a cyclosporin A-type ligand, tetracycline or a steroid ligand. Such binding causes oligomerization of homotypic (the same) or heterotypic (different) chimeric protein molecules.

Optionally the same or additional recombinant DNA constructs (or a second series of such construct(s), contain the target gene (preferably ipaB) under the transcriptional control of a transcriptional control element (e.g. promoter/enhancer) responsive to a signal triggered by ligand-mediated oligomerization of the chimeric proteins after exposure to the ligand. In such constructs, the target gene, preferably of Shigella or other bacterial origin, is under control of heterologous transcriptional control elements.

In one embodiment, the DNA construct contains (a) a transcriptional control element responsive to the oligomerization of a chimeric protein as described above, (b) an ipaB gene or fragment thereof, and (c) flanking DNA from a gene present in the target cell or sufficiently similar thereto to permit homologous recombination of the transcriptional control element and ipaB gene into the host cell. Choice of the flanking DNA allows targeted homologous recombination of the ipaB gene into a desired locus of the cellular DNA. In another embodiment, the above construct may lack the responsive transcriptional control element but rather exploits the responsive element in the genetic locus of the target cell into which it is placed. For ex vivo transfection, the constructs of may also contain a selectable marker permitting selection of transfectants containing the construct. The constructs preferably comprise DNA vectors whether for episomal transfection or for integration into the host cell chromosomes. Preferred vectors may be viral vectors, including for example an adenovirus, adeno-associated-virus (AAV) or retroviral vectors, as described in more detail below.

Thus, utilizing the above approach, target cells, preferably human cells, are caused to contain a first DNA construct encoding a chimeric protein comprising (i) at least one receptor domain capable of binding to a selected oligomerizing ligand and (ii) another protein domain, heterologous to the receptor domain, but capable, upon oligomerization with one or more other like domains, of triggering the activation of transcription of a target gene, preferably ipaB, under the transcriptional control of a transcriptional control element responsive to the oligomerization. The cells further contain the target ipaB gene which is under the expression control of a transcriptional control element responsive to the oligomerization ligand. Hence, following exposure to the selected ligand, the cells express the ipaB gene, activating the apoptosis program and killing the cells.

A chimeric protein receptor can contain a cytoplasmic domain from one of the various cell surface membrane receptors, including muteins thereof, where the recognition sequence involved in initiating transcription associated with the cytoplasmic domain is known or a gene responsive to such sequence is known. The receptor-associated cytoplasmic domains of particular interest will have the following characteristics: receptor activation leads to initiation of transcription for relatively few (desirably fewer than 100) and generally innocuous genes in the host cells; the other factors necessary for transcription initiated by receptor activation are present in the host cells; genes which are activated other than the target genes will not interfere in the action of ipaB once expressed or other aspects of the cellular apoptotic machinery; oligomerization of the cytoplasmic domain results in signal initiation; and joining of the cytoplasmic domain to a desired ligand-binding domain will not interfere with signalling. A number of different cytoplasmic domains are known. Many of these domains are tyrosine kinases or are complexed with tyrosine kinases, e.g., CD34, IL-2R, IL-3R, etc. For a review see Cantley, et al., *Cell* (1991) 64:281. Tyrosine kinase receptors which are activated by cross-linking, e.g. dimerization (based on nomenclature first proposed by Yarden et al., *Annu. Rev. Biochem.* (1988) 57:443) include subclass I: EGF-R, ATR2/neu, HER2/neu, HER3/c-erbB-3, Xmrk; subclass II: insulin-R, IGF-1-R (insulin-like growth factor receptor], IRR; subclass III: PDGF-R-A, PDGF-R-B, CSF-1-R (M-CSF/c-Fms), c-kit, STK1/Flk-2; and subclass IV: FGF-R, flg [acidic FGF], bek [basic FGF]); neurotrophic tyrosine kinases: Trk family, includes NGF-R, Ror1,2. Receptors which associate with tyrosine kinases upon cross-linking include the CD3 ζ family: CD3 ζ and CD3 η (found primarily in T cells, associates with Fyn); β and γ chains of FcγRI (found primarily in mast cells and basophils); γ chain of FcγRIII/CD16 (found primarily in macrophages, neutrophils and natural killer cells); CD3 γ, δ0 and ε (found primarily in T cells); Ig-α/MB-1 and Ig-β/B29 (found primarily in B cells). Many cytokine and growth factor receptors associate with common β subunits which interact with tyrosine kinases and /or other signalling molecules and which can be used as cytoplasmic domains in chimeric proteins of this invention. These include (1) the common β subunit shared by the GM-CSF, IL-3 and IL-5 receptors; (2) the β chain gp130 associated with the IL-6, leukemia inhibitory factor (LIF), ciliary neurotrophic factor (CNTF), oncostatin M, and IL-11 receptors; (3) the IL-2 receptor γ subunit associated also with receptors for IL-4, IL-7 and IL-13 (and possibly IL9); and (4) the β chain of the IL-2 receptor which is homologous to the cytoplasmic domain of the G-CSF receptor.

The family of interferon receptors which include receptors for interferons α/β and γ (which can activate one or more members of the JAK, Tyk family of tyrosine kinases) as well as the receptors for growth hormone, erythropoietin and prolactin (which also can activate JAK2) can also be used as sources for cytoplasmic domains. Other sources of cytoplasmic domains include the TGF-β family of cell surface receptors (reviewed by Kingsley, D., *Genes and Develop.,* 1994, 8:133).

The tyrosine kinases associated with activation and inactivation of transcription factors are of interest in providing specific pathways which can be controlled and can be used to initiate or inhibit expression of an exogenously introduced ipaB gene.

The cytoplasmic domain, as it exists naturally or as it may be truncated, modified or mutated, will be at least about 10, usually at least about 30 amino acids, more usually at least about 50 amino acids, and generally not more than about 400 amino acids (Romeo et al., *Cell* (1992) 68:889–893). While any species can be employed, the species endogenous to the host cell, particularly human, is preferred. However, in many cases, the cytoplasmic domain from a different species can be used effectively. Any of the above indicated cytoplasmic domains may be used, as well as others which are presently known or may subsequently be discovered.

For the most part, the other chimeric proteins associated with transcription factors, will differ primarily in having a cellular targeting sequence which directs the chimeric protein to the internal side of the nuclear membrane and having transcription factors or portions thereof as the action domains. Usually, the transcription factor action domains can be divided into "DNA binding domains" and "activation domains." Also contemplated is a DNA binding domain with one or more ligand binding domains and an activation domain with one or more ligand binding domains. This allows coupling of the DNA binding domain can be to a plurality of binding domains and/or activation domains.

Cellular targeting domains include a signal peptide or sequence which transports the chimeric protein to the cell surface membrane, where the same or other sequences can encode portions which bind the chimeric protein to the cell surface membrane. The choice of membrane retention domain, which fall into two categories, is not critical: A transmembrane retention domain (an amino acid sequence which extends across the membrane) and a lipid membrane retention domain (which lipid associates with membrane lipids). Generally, the transmembrane domain will have from about 18–30 amino acids, more usually about 20–30 amino acids, where the central portion is primarily neutral, non-polar amino acids, and the termini are polar amino acids, frequently charged amino acids, generally having about 1–2 charged, primarily basic amino acids at the termini of the transmembrane domain followed by a helical break residue, e.g. pro- or gly-.

The ligand binding ("dimerization") domain of a chimeric protein can be any convenient domain which will allow for induction using a natural or unnatural ligand, preferably an unnatural synthetic ligand. The binding domain can be internal or external to the cellular membrane, depending upon the nature of the construct and the choice of ligand. A wide variety of binding proteins, including receptors, are known, including binding proteins associated with the cytoplasmic regions indicated above. Of particular interest are binding proteins for which ligands (preferably small organic ligands) are known or may be readily produced. These receptors or ligand binding domains include the FKBPs and cyclophilin receptors, the steroid receptors, the tetracycline receptor, other receptors discussed above, as well as "unnatural" receptors, which can be obtained from antibodies, particularly the heavy or light chain subunit, mutated sequences thereof, random amino acid sequences obtained by stochastic procedures, combinatorial syntheses, and the like. For the most part, the receptor domains will be at least about 50 amino acids, and fewer than about 350 amino acids. The binding domain is preferably small (<25 kDa), to allow efficient transfection in viral vectors, monomeric and nonimmunogenic. The binding domain is selected such that there are synthetically accessible, cell permeable, nontoxic ligands that can be configured for inducing dimerization.

The receptor domain can be intracellular or extracellular depending upon the design of the construct encoding the chimeric protein and the availability of an appropriate ligand. For use with hydrophobic ligands, the binding domain can be on either side of the membrane. For use with hydrophilic ligands, particularly protein ligands, the binding domain will usually be external to the cell membrane (unless there is a transport system exists for internalizing the ligand in a form available for binding.

For multimerizing the receptor, the ligand for the receptor domains of the chimeric surface membrane proteins will usually have at least two binding sites, each of which can bind to the receptor domain. Desirably, the subject ligands are dimers or higher order oligomers of small synthetic organic molecules, the individual molecules typically being at least about 150 Da and no larger than 5 kDa. Synthetic ligands and receptors can be employed. Examples of synthetic ligand:natural receptor pairs are as follows: dimeric FK506:FKBP receptor, dimerized cyclosporin A:cyclophilin, dimerized estrogen:estrogen receptor, dimerized glucocorticoid:glucocorticoid receptor, dimerized tetracycline:tetracycline receptor, dimerized vitamin D:vitamin D receptor, and the like. "Higher order" ligands, e.g., trimers, can be used. Unnatural receptors may include antibody subunits, modified antibody subunits or chemically modified receptors and the like. These ligand-binding units should bind with high affinity (preferably Kd<$10^{-8}$M) and should be capable of being chemically dimerized.

The dimeric (or higher order) ligands may be covalently attached through a common linker moiety. Mixed dimer ligands are useful for mediating heterooligomerization of two dissimilar chimeric proteins having dissimilar receptor domains.

When using biologically active ligands, such as steroids, the molecules can be oligomerized so that their natural biological activity is substantially diminished without loss of their ability to bind the chimeric protein which contains one or more steroid receptor domains. As a non-limiting example, glucocorticoids and estrogens can be so used. Various drugs can also be which are known to bind to a particular receptor with high affinity. Where such binding domains are known, the binding domain and not the complete native receptor is preferably used to construct the chimeric protein.

For linking groups in the construction of a ligand, various functionalities can be used, such as amide groups, including carbonic acid derivatives, ethers, esters, including organic and inorganic esters, amino, or the like. The monomers to be linked can be modified by oxidation, hydroxylation, substitution, reduction, etc., to provide a site for coupling. Those skilled in the art will know how to select an appropriate site on a give monomer for coupling. An oligomeric or multimeric ligand can be synthesized by any convenient means such that the linking group is at a site which does not interfere with the binding of ligand to its receptor domain on the chimeric protein. Where a biologically active site receptor-binding site of a ligand differ, it is preferable to link the ligand at the active site to cause inactivation of the bioactivity. Various linking groups can be employed, generally having from about 1–30 atoms (other than hydrogen), primarily composed of carbon, hydrogen, nitrogen, oxygen, sulphur and phosphorous. The linking groups can involve a wide variety of functionalities, such as amides and esters, both organic and inorganic, amines, ethers, thioethers, disulfides, quaternary ammonium salts, hydrazines, etc. The chain can include aliphatic, alicyclic, aromatic or heterocyclic groups. The chain will be selected based on ease of synthesis and the stability of the multimeric ligand. Thus, for long-term activity, a relatively inert chain is preferred such that the link will not be cleaved. Alternatively, for a short circulating half-life in vivo, readily cleavable groups are employed, such as esters and amides, particularly peptides.

For use with intracellular binding domains, the ligand is selected for its ability to cross the membrane in a bioactive form. Various ligands are hydrophobic or can be made so by appropriate modification with lipophilic groups. The linking bridge can serve to enhance the lipophilicity of the ligand by providing aliphatic side chains of from about 12 to 24 carbon atoms. Alternatively, one or more groups can be provided which will enhance transport across the membrane, desirably without endosome formation.

If necessary, ligand antagonists generally in the form of monomers can be used to reverse or inhibit the effect of the multimeric ligand. Thus, to limit the effect of ipaB activation or to "turn off the switch," such that some cells in the targeted population are spared, a monomeric ligand for the same receptor domain is used. Conveniently, the parent ligand moiety can be modified at the same site as the multimer, using the same procedure, except substituting a monofunctional compound for the polyfunctional compound. Instead of the polyamines, monoamines, particularly of from 2 to 20 (although they can be longer), and usually 2 to 12, carbon atoms can be used, such as ethylamine, hexylamine, benzylamine, etc. Alternatively, the monovalent form of the parent ligand compound can be used if it does not have undue non-desired activity (e.g. immunosuppression, mitogenesis, toxicity, etc.).

Transcription Initiation Region

A second construct or series of constructs has a responsive element in the 5' region, which responds to ligand-mediated oligomerization of the chimeric receptor protein, presumably via the generation and transduction of a transcription initiation signal. At least one transcription initiation system (factor) must be known which is activated either directly or indirectly by the cytoplasmic domain or by association of two domains. At least one promoter region must be known which is responsive to the transcription initiation system, whether it be a heterologous promoter or the native promoter of the ipaB gene or homologue thereof. An action domain is selected for the chimeric proteins (see above) based on the role of that action domain in initiating transcription via a given promoter or responsive element.

Where the responsive element is known, it is included in the target gene construct to provide an expression cassette for integration into the genome (whether episomally or chromosomal). It is not necessary to have isolated the particular sequence of the responsive element, so long as a gene is known which is transcriptionally activated by the cytoplasmic domain upon natural ligand binding to the protein comprising the cytoplasmic domain. Homologous recombination can be used for inserting the ipaB gene downstream from the promoter region to be under the transcriptional regulation of the endogenous promoter region.

The responsive element can be a single sequence or can be oligomerized, usually having not more than about 5 repeats, usually having about 3 repeats.

The expression construct preferably has at its 5' end in the direction of transcription, the responsive element and the promoter sequence which allows for induced transcription initiation of an ipaB gene to which they are operatively linked. The transcriptional termination region is not as important, and can be used to enhance the lifetime of or make short half-lived, mRNA by inserting AU sequences which reduce stability of the mRNA. Any region known to those skilled in the art can be employed which provides for the necessary transcriptional termination, and as appropriate, translational termination.

Introduction of Constructs into Cells

The constructs can be introduced as one or more DNA molecules or constructs. The constructs are prepared in conventional ways, where the genes and regulatory regions may be isolated, as appropriate, ligated, cloned in an appropriate cloning host, analyzed by restriction or sequencing, or other convenient means. Using PCR, individual fragments including all or portions of a functional unit may be isolated, where one or more mutations may be introduced using "primer repair", ligation, in vitro mutagenesis, etc. as appropriate. The construct(s) once completed and demonstrated to have the appropriate sequences may then be introduced into host cells by any convenient means, as discussed in more detail below.

The constructs may be introduced as a single DNA molecule encoding all of the genes, or different DNA molecules having one or more genes. The constructs may be introduced simultaneously or consecutively, each with the same or different markers. In an illustrative example, one construct would contain ipaB under the control of a specific responsive element (e.g. NFAT), another encoding the receptor fusion protein comprising the signaling region fused to the ligand receptor domain.

Vectors containing useful elements such as selectable and/or amplifiable markers, promoter/enhancer elements for expression in mammalian, particularly human, cells, and which may be used to prepare stocks of construct DNAs and for carrying out transfections are well known in the art. Many are commercially available.

Various techniques have been developed for modification of target tissue and cells in vivo. A number of virus vectors, discussed below, are known which allow transfection and random integration of the virus into the host. See, for example, Dubensky et al. (1984) *Proc. Natl. Acad. Sci. USA* 81:7529–7533; Kaneda et al., (1989) *Science* 243:375–378; Hiebert et al. (1989) *Proc. Natl. Acad. Sci. USA* 86:3594–3598; Hatzoglu et al., (1990) *J. Biol. Chem.* 265:17285–17293; Ferry et al. (1991) *Proc. Natl. Acad. Sci. USA* 88:8377–8381. Routes and modes of administering the vector include injection, e.g intravascularly or intramuscularly, inhalation, or other parenteral administration.

The manner of modification will depend on the nature of the tissue, the efficiency of cellular modification required, the number of opportunities to modify the particular cells, the accessibility of the tissue to the DNA composition being be introduced, and the like.

The DNA introduced need not be integrated in every case. In some situations, transient maintenance of the DNA introduced may be sufficient to activate the apoptotic program.

Administration of the Ligand

Once the constructs have been provided to the target cells to be killed, the ligand which produces activation of the cytoplasmic domain leading to expression of ipaB and induction of apoptosis may then be administered as desired. Depending upon the binding affinity of the ligand, the response desired, the manner of administration, the half-life, the number of cells present, any of a number of protocols may be employed. The ligand may be administered parenterally or orally. The number of administrations will depend upon the factors described above. The ligand may be taken orally as a pill, powder, or dispersion; bucally; sublingually; injected intravascularly, intraperitoneally, subcutaneously; by inhalation, or the like. The ligand (and monomeric compound) may be formulated using conventional methods and materials well known in the art for the various routes of administration. The precise dose and particular method of administration will depend upon the above factors and be determined by the attending physician or human or animal healthcare provider. For the most part, the manner of administration will be determined empirically.

In the event that the activation by the ligand is to be reversed, terminated or limited, the monomeric ligand or other single binding site competitor is administered. in any convenient way, particularly intravenously if a rapid reversal is desired.

The particular dosage of the ligand for any application may be determined in accordance with the procedures used for therapeutic dosage monitoring, where a particular level of expression is desired either in a short duration or over an extended period of time, or where repetitive activation of apoptosis is desired. In the latter case, individual or repeated doses of ligand are administered over short periods of time, with extended intervals, for example, two weeks or more. A dose of the ligand within a predetermined range would be given and monitored for response, so as to define the relation between duration of ligand administration and ipaB expression level or therapeutic effect.

Gene Therapy and Delivery Methods

Two broad categories of gene transfer methods are utilized in the present invention: in vivo and ex vivo methods.

In the latter, DNA transfer is performed ex vivo and the transfected cells are introduced into the subject animal.

Gene therapy involves introduction of a "foreign" gene into a cell and ultimately, into a live animal. Several general strategies for gene therapy have been studied and have been reviewed extensively (Yang, N-S., *Crit. Rev. Biotechnol.* 12:335–356 (1992); Anderson, W. F., *Science* 256:808–813 (1992); Miller, A. S., *Nature* 357:455–460 (1992); Crystal, R. G., *Amer. J. Med.* 92(suppl 6A):44S-52S (1992); Zwiebel, J. A. et al., *Ann. N.Y. Acad. Sci.* 618:394–404 (1991); McLachlin, J. R. et al., *Prog. Nucl. Acid Res. Molec. Biol.* 38:91–135 (1990); Kohn, D. B. et al., *Cancer Invest.* 7:179–192 (1989), which references are herein incorporated by reference in their entirety).

For accomplishing the objectives of the present invention, gene therapy would be accomplished by direct transfer of a the functionally active IpaB DNA into mammalian somatic tissue or organ in vivo, and more preferably, into cells which are to be killed. DNA transfer can be achieved using a number of approaches described below. As is known in the art an optimal gene delivery system should bind the DNA and make it soluble, effectively transfer the DNA into the cell, protect it from nucleases, release the DNA for efficient activity, and be targetable to specific cells. The optimal system may differ according to the particular gene transfer application, e.g., systemic versus local delivery, target cell type, etc.

In general, for transfer of DNA according to the present invention to achieve cell death by apoptosis, use of viral vectors is preferable to the use of plasmid DNA.

Examples of successful transfer of genes known in the art include: (a) direct injection of plasmid DNA into mouse muscle tissues leading to indefinite expression of marker genes (Wolff, J. A. et al., *Science* 247:1465 (1990); Acsadi, G. et al., *The New Biologist* 3:71 (1991)); (b) retroviral vectors effective for in vivo and in situ infection of blood vessel tissues; (c) portal vein injection and direct injection of retrovirus preparations into liver to effect gene transfer and expression in vivo (Horzaglou, M. et al., *J. Biol. Chem.* 265:17285 (1990); Koleko, M. et al., *Human Gene Therapy* 2:27 (1991); Ferry, N. et al., *Proc. Natl. Acad. Sci. USA* 88:8387 (1991)); (d) intratracheal infusion of recombinant adenovirus into lung tissues effective for in vivo transfer and prolonged expression of foreign genes in lung respiratory epithelium (Rosenfeld, M. A. et al., *Science* 252:431 (1991); (e) Herpes simplex virus vectors for in vivo gene transfer into brain tissue (Ahmad, F. et al., eds, *Miami Short Reports—Advances in Gene Technology: The Molecular Biology of Human Genetic Disease*, Vol 1, Boehringer Mannheim Biochemicals, USA, 1991).

Retroviral Vectors

Retroviral-mediated human gene therapy utilizes amphotrophic, replication-deficient retrovirus systems (Temin, H. M., *Human Gene Therapy* 1:111 (1990); Temin et al., U.S. Pat. No. 4,980,289; Temin et al., U.S. Pat. No. 4,650,764; Temin et al., U.S. Pat. No. 5,124,263; Wills, J. W. U.S. Pat. No. 5,175,099; Miller, A. D., U.S. Pat. No. 4,861,719; Miller, A. D., *Curr. Top. Microbiol. Immunol.* 158:1–24 (1989)). Such vectors have been used to introduce functional DNA into human cells or tissues, for example, the adenosine deaminase gene into lymphocytes, the NPT-II gene and the TNF gene into tumor infiltrating lymphocytes. Retrovirus-mediated gene delivery generally requires target cell proliferation for gene transfer (Miller, D. G. et al., *Mol. Cell. Biol.* 10:4239 (1990). This condition is met by the preferred target cells for the present invention, i.e., growing tumor cells or activated lymphocytes in the case of autoimmunity. Gene therapy of cystic fibrosis using transfection by plasmids using any of a number of methods and by retroviral vectors has been described by Collins et al., U.S. Pat. No. 5,240,846.

For use in the present methods, DNA encoding IpaB is packaged into retrovirus vectors using one of several known packaging cell line that produce replication-defective retroviruses (see, for example, Cone, R. D. et al., *Proc. Natl. Acad. Sci. USA* 81:6349–6353 (1984); Mann, R. F. et al., *Cell* 33:153–159 (1983); Miller, A. D. et al., *Molec. Cell. Biol.* 5:431–437 (1985),; Sorge, J., et al., *Molec. Cell. Biol.* 4:1730–1737 (1984); Hock, R. A. et al., *Nature* 320:257 (1986); Miller, A. D. et al., *Molec. Cell. Biol.* 6:2895–2902 (1986). Newer packaging cell lines which are efficient an safe for gene transfer have been described more recently (Bank et al., U.S. Pat. No. 5,278,056).

The gene therapy approach can be utilized in a site specific manner to deliver a retroviral vector to the tissue or organ of choice. Thus, for example, a catheter delivery system can be used (Nabel, E. G. et al., *Science* 244:1342 (1989)). Such methods, using either a retroviral vector or a liposome vector, is particularly useful to deliver the gene to a blood vessel wall, or into the blood circulation of a tumor.

Other Viral Vectors

Other virus vectors may also be used, in particular for human gene therapy, including recombinant adenovirus vectors (Horowitz, M. S., In: *VIROLOGY*, Fields, B. N. et al., eds, Raven Press, New York, 1990, p. 1679; Berkner, K. L., *Biotechniques* 6:616–629 (1988), Strauss, S. E., In: *THE ADENOVIRUSES*, Ginsberg, H. S., ed., Plenum Press, New York, 1984, chapter 11) or adeno-associated virus (AAV) (Ohi, S. et al., *Gene* 89:279–282 (1990); Dixit, M. et al., *Gene* 104:253–257 (1991); Samulski, R. J. et al., *EMBO J.* 10:3941 (1991)). Herpes simplex virus (HSV) is well-adapted for neuron-specific delivery (Geller, A. I. et al., *Science* 241:1667–1669 (1988)). Advantages of adenovirus vectors for human gene therapy include the fact that recombination is rare, no human malignancies are known to be associated with such viruses, the adenovirus genome is double stranded DNA which can be manipulated to accept foreign genes of up to 7.5 kb in size, and live adenovirus is a safe human vaccine organisms.

Another vector which can express the ipaB DNA molecule of the present invention, and is useful in gene therapy, particularly in humans, is vaccinia virus, which can be rendered non-replicating (U.S. Pat. Nos. 5,225,336; 5,204,243; 5,155,020; 4,769,330). To avoid inhibition of ICE by viral genes, such as crmA, vaccinia mutants defective in crmA must be utilized. Descriptions of recombinant vaccinia viruses containing heterologous DNA and its uses in immunization and gene therapy are reviewed in: Moss, B., *Curr. Opin. Genet. Dev.* (1993) 3:86–90; Moss, B. *Biotechnology* (1992) 20:345–362; Moss, B., *Curr Top Microbiol Immunol* (1992) 158:25–38; Moss, B., *Science* (1991) 252:1662–1667; Piccini, A et al., *Adv. Virus Res.* (1 988) 34:43–64; Moss, B. et al., *Gene Amplif Anal* (1983) 3:201–213.

A nontoxic and efficient method has recently been reported based on the Sendai virus, also known as hemagglutinating virus of Japan (HVJ). HVJ-liposome-mediated gene transfer is performed Morishita R et al., *Hypertension* (1993) 21:894–89. This method was used to transfect vascular smooth muscle cells and COS cells with human angiotensin converting enzyme (ACE). The method was more efficient than lipofection. Tomita N et al., *Biochem Biophys Res Commun* (1992) 186:129–34 developed a method in which plasmid DNA and high mobility group 1 protein (a nuclear protein) are co-encapsulated in liposomes and co-introduced into target cells by HVJ-mediated membrane fusion. This is a general method in which foreign genes and nuclear proteins are encapsulated into the same liposomes, which are then treated with inactivated HVJ. In this method, HVJ enables foreign genes to be introduced directly into the cytoplasm by membrane fusion and the nuclear proteins transport the foreign genes rapidly into the nuclei. In this study, a reporter gene, was introduced into the kidney of intact rats through a cannula in the renal artery. Tomita N et al., *Cancer Detect Prev* (1994) 18:485–491 shows the successful introduction and expression of a human insulin gene in the mouse, with presence of human insulin in the mouse plasma and its reduction of plasma glucose levels. The human renin gene was similarly introduced into adult rat liver resulting in significant elevation of blood pressure for 6 days compared with controls (Tomita, N. et al., *Circ Res* (1993) 73:898–905)

Artificial Viral Envelopes

Based on the concept of viral mimicry, artificial viral envelopes (AVE) are designed based on the structure and composition of a viral membrane, such as HIV-1 or RSV and used to deliver genes into cells in vitro and in vivo. See, for example, U.S. Pat. No. 5,252,348, Schreier H. et al., *J. Mol. Recognit.*, 1995, 8:59–62; Schreier H et al., *J. Biol. Chem.*, 1994, 269:9090–9098; Schreier, H., *Pharm. Acta Helv.* 1994, 68:145–159; Chander, R et al. *Life Sci.*, 1992, 50:481–489, which references are hereby incorporated by reference in their entirety. The envelope is preferably produced in a two-step dialysis procedure where the "naked" envelope is formed initially, followed by unidirectional insertion of the viral surface glycoprotein of interest. This process and the physical characteristics of the resulting AVE are described in detail by Chander et al., (supra). Examples of AVE systems are (a) an AVE containing the HIV-1 surface glycoprotein gp160 (Chander et al., supra; Schreier et al., 1995, supra) or glycosyl phosphatidylinositol (GPI)-linked gp120 (Schreier et al., 1994, supra), respectively, and (b) an AVE containing the respiratory syncytial virus (RSV) attachment (G) and fusion (F) glycoproteins (Stecenko, A. A. et al., *Pharm. Pharmacol. Lett.* 1:127–129 (1992)). The "viral" functions of surface insertion and conformational integrity of the gp160 has been confirmed by sandwich immunolabelling with anti-gp 160 mAb and colloidal gold carrying mouse anti-IgG. Selective delivery of contents to CD4$^+$-cells has been demonstrated. AVEs may be tested by loading with FITC-dextran and incubating with a population of target cells. For example, using the HIV gp160-containing AVE cells that are predominantly CD4$^+$ (REX-1B), flow cytometric analysis demonstrated incorporation of the label (77% of REX-1B cells after 60 minutes) whereas, in a population largely lacking the viral receptor (KG-1; about 18% CD4$^+$), only 25% of cells take up label. icin A at concentrations as low as 2 ng/ml arrested cell growth of CD4-positive MOLT-4 cells, whereas 8 ng/ml Ricin A in solution had no effect on cell growth. The arrest of cell growth was reverted in the presence of excess anti-gp120 monoclonal antibody. "Naked" envelopes (without HIV-1 rgp160 inserted) show background levels of interaction with target cells, transferring material less efficiently and non-specifically. For a detailed description, see also Schreier, 1995 (supra) and a report showing inhibitable binding of GPI-anchored gp120 AVE to CHO cells and 293 cells transfected with human CD4 or CD4-DAF, respectively (Schreier et al., 1994, supra). Thus, vesicles are constructed which mimic the natural membranes of enveloped viruses in their ability to bind to and deliver materials to cells bearing corresponding surface receptors.

AVEs are used to deliver genes both by intravenous injection and by instillation in the lungs. For example, AVEs are manufactured to mimic RSV, exhibiting the RSV F surface glycoprotein which provides selective entry into epithelial cells. F-AVE are loaded with a plasmid coding for the gene of interest, preferably ipB (or a reporter gene such as CAT not present in mammalian tissue). Recipient animals, preferably humans have an effective dose of the gene instilled into their lungs via a syringe connected to a thin endotracheal tube or, more preferably by inhalation. When carried out in rats using CAT as a reporter gene, animals sacrificed 48 hr after instillation, lungs showed significant activity of CAT above background. Though there was practically no expression in the liver, transfection and expression occurred in the kidney, most likely due to lymphatic delivery of the gene product to the blood and then to the kidney. In a similar study, rats were injected intravenously with AVEs carrying on their surface a specific lung targeting molecule (which has a high binding affininty to the surface of lung endothelial cells) and carrying a payload of a plasmid encoding (heat-resistant) placental alkaline phosphatase (PAP). Anesthetized rats were injected with 600 $\mu$l L-AVE containing 100 $\mu$g of the gene product via a tail vein. Organs were analyzed after 60 hours for the presence of the PAP gene using a histochemical method which resulted in red precipitate in transfected cells. Extensive staining of lung tissue occurred, indicating efficient delivery to the targeted endothelial cells. Thus, both target selectivity as well as high efficiency of gene delivery have been unequivocally demonstrated in vivo using AVE.

The AVE system described herein in physically and chemically essentially identical to the natural virus yet is entirely "artificial", as it is constructed from phospholipids, choloesterol, and recombinant viral surface glycoproteins. Hence, there is no carry-over of viral genetic information and no danger of inadvertant viral infection. Construction of the AVEs in two independent steps allows for bulk production of the plain lipid envelopes which, in a separate second step, can then be marked with the desired viral glycoprotein, also allowing for the preparation of protein cocktail formulations if desired.

Bacterial Delivery

A preferred delivery vehicle for use in the present invention are based on the recent description of attenuated Shigella as a DNA delivery system (Sizemore, D. R. et al., *Science* 270:299–302 (1995), which reference is incorporated by reference in its entirety). This approach exploits the ability of Shigellae to enter epithelial cells and escape the phagocytic vacuole as a method for delivering the IpaB construct into the cytoplasm of the target cell. Invasion with as few as one to five bacteria can result in expression of the foreign plasmid DNA delivered by these bacteria. As little as $4–20\times10^9$ $\mu$g DNA by Shigella was shown to be sufficient for expression of a transfected marker. Such Shigella-mediated delivery of plasmid DNA can be achieved in various cell types which can be infected by Shigella, and has been shown in kidney cells, mastocytoma cells. Plasmid DNA has been successfully delivered to animals in vivo, including keratoconjunctival delivery in guinea pig and intranasal delivery in mice. It is important that the delivery be done using highly attenuated bacteria for reasons of safety in human subjects. Importantly, this approach is not restricted to Shigella. Shigella invasion genes can be transferred to other bacterial genera such as *E. coli*. Other bacteria such as Listeria can invade cells and break out of phagocytic vacuoles and enter the cytoplasm. An important advantage of this approach for gene therapy is the ease an acceptability of oral and other forms of mucosal delivery.

Non-Viral and Liposome Mediated Delivery

In addition to virus-mediated or bacterially-mediated gene transfer in vivo, physical means well-known in the art can be used for direct gene transfer, including administration of plasmid DNA (Wolff et al., 1990, supra) and particle-bombardment mediated gene transfer (Yang, N.-S., et al., *Proc. Natl. Acad. Sci. USA* 87:9568 (1990); Williams, R. S. et al., *Proc. Natl. Acad. Sci. USA* 88:2726 (1991); Zelenin, A. V. et al., *FEBS Lett.* 280:94 (1991); Zelenin, A. V. et al., *FEBS Lett.* 244:65 (1989); Johnston, S. A. et al., *In Vitro Cell. Dev. Biol.* 27:11 (1991)). Furthermore, electroporation, a well-known means to transfer genes into cell in vitro, can be used to transfer DNA molecules according to the present invention to tissues in vivo (Titomirov, A. V. et al., *Biochim. Biophys. Acta* 1088:131 ((1991)). In order to overcome therapy-limiting toxicity, antigenicity and lack of expression of transgenes in nonreplicating cells, non-viral vectors may be used. Such methods of gene transfer is also known as "carrier mediated gene transfer" (Wu, C. H. et al., *J. Biol. Chem.* 264:16985 (1989); Wu, G. Y. et al., *J. Biol. Chem.* 263:14621 (1988); Soriano, P. et al., *Proc. Natl. Acad. Sci. USA* 80:7128 (1983); Wang, C-Y. et al., *Proc. Natl. Acad. Sci. USA* 84:7851 (1982); Wilson, J. M. et al., *J. Biol. Chem.* 267:963 (1992)).

Cationic Lipids

A preferred type of mediator of nonviral transfection in vitro and in vivo is cationic (ammonium derivatized) lipids. These positively charged lipids form complexes with negatively charged DNA, resulting in DNA charged neutralization and compaction. The complexes endocytosed upon association with the cell membrane, and the DNA somehow escapes the endosome, gaining access to the cytoplasm. Cationic lipid:DNA complexes appear highly stable under normal conditions. Studies of the cationic lipid DOTAP suggest the complex dissociates when the inner layer of the cell membrane is destabilized and anionic lipids from the inner layer displace DNA from the cationic lipid. Several cationic lipids are available commercially. Two of these, DMRI and DC-cholesterol, have been used in human clinical trials. First generation cationic lipids are less efficient than viral vectors. A few cationic lipid compounds (*Genetic Engineering News*, Nov. 15, 1995, pg. 1) are up to two logs more active in their ability to express a reporter gene (CAT) in mouse lung than the compounds used in earlier gene transfer trials for cystic fibrosis. Although such lipids are still relatively inefficient compared to adenovirus (two logs more DNA molecules are required to achieve an equivalent level of expression), DNA is easier to make than virus. The novel cationic lipid:DNA complexes are 500-fold more active than naked DNA. For delivery to lung, any inflammatory responses accompanying the liposome administration are reduced by changing the delivery mode to aerosol administration which distributes the dose more evenly.

One well-known method for effecting efficient DNA transfection is termed lipofection (Felgner, P L et al., *Proc. Natl. Acad. Sci. USA* (1987) 84:7413–7417). Cationic liposomes have been successfully employed to express the CFTR protein in rats and to correct the chloride ion transport defect both in transgenic mice, and in human patients. In one embodiment, this method utilizes a synthetic cationic lipid, N-[1-(2,3-dioleyloxy)propyl]-N,N,N-trimethylammonium chloride (DOTMA). Small unilamellar liposomes containing DOTMA interact spontaneously with DNA to form lipid-DNA complexes with 100% entrapment of the DNA. DOTMA facilitated fusion of the complex with the membrane of cultured cells resulting in both uptake and expression of the DNA. The technique is considered simple, highly reproducible, and effective for both transient and stable expression of transfected DNA.

A method employing cationic liposomes is useful for direct gene transfer in the therapy of cancer and other diseases as discussed by Farhood, H. et al., *Ann N Y Acad Sci* (1994) 716:23–35). Cationic liposomes mediate efficient delivery of DNA and DNA/protein complex to mammalian cells in vitro and in vivo. Cationic cholesterol derivatives mixed with phosphatidylethanolamine and sonicated to form small unilamellar vesicles complex with DNA and mediate the entry into the cytosol from the endosome compartment. One of the liposome formulations, DC-Chol liposomes, has been used in a gene therapy clinical trial for melanoma. Such cationic liposomes were used for the delivery of trans-activating protein factors to regulate and control the expression of delivered transgenes in a protein dose-dependent manner. Human tumor cells selected for cis-platin resistance or isolated from patients who have failed cis-platin therapy are highly transfectable with cationic liposomes. Thus the present method of introducing IpaB into a tumor cells will permit serial therapy with cis-platin (or another conventional cancer chemotherapeutic agent) and the ipaB gene therapy to eradicate malignancy.

The use of cationic liposomes may be combined with Adeno-associated (AAV)-based plasmids to introduce IpaB into cancer cells. This method has been used to transfer the IL-2 gene in human prostate cancer (Vieweg, J et al. *Cancer Res* (1995) 55:2366–2372). Liposomes allowed introduction and expression of the IL-2 gene in a rat tumor cell line and in primary human prostatic tumor cells. Liposome-DNA complexes containing the AAV inverted terminal repeats exhibited high levels of gene transfer and IL-2 expression in primary human prostatic tumor cells comparable to or exceeding the IL-2 secretion from retrovirally transduced prostate cancer cells.

A method for transient expression of genes in normal colonic epithelium involves liposomal gene delivery by rectal catheter infusion. This approach has been used to express a reporter gene and the human APC tumor suppressor gene under control of a constitutive promoter in a rodent model (Westbrook C A et al., *Hum Mol Genet* (1994) 3:2005–2010). High efficiency transfection was achieved (close to 100% of epithelial cells expressing the introduced gene). Expression in this system was transient, not persisting beyond 4 days (consistent with the normal turnover time of gut epithelium). However, repeated treatments could maintain expression. Importantly, for the purposes of inducing apoptosis as described herein, such transient expression of the ipaB gene may be sufficient to achieve the desired cytotoxic effect.

In another embodiment of this invention, ipab DNA or protein are introduced into cells by using targeted liposomes (Nicolau, C. et al., *Proc. Natl. Acad. Sci. USA* 80:1068 (1983), Soriano et al., supra) such as immunoliposomes, which can incorporate acylated monoclonal antibodies into the lipid bilayer (Wang et al., supra). Polyclonal antibodies and mAbs specific for various types of tumors, viral antigens or cell surface markers of various normal cell types are well-known in the art. Thus, the IpaB protein, a functional derivative thereof, or DNA encoding the protein or derivative, is specifically introduced into a selected type of target cell by means of an antibody selective for that cell type. Thus, for example, an antibody specific for a class or subclass of lymphocytes, or for a particular T cell receptor variable region, can be used to target the IpaB protein or DNA to a particular lymphocyte population in the treatment of autoimmunity. An antibody specific for a tumor associated antigen is used to target the therapeutic composition to cells of a tumor.

It is now possible to deliver purified proteins, such as IpaB or a derivative thereof, into a variety of types of cells using a new polycationic lipid preparation, LipofectAMINE® (Sells, M A et al., Biotechniques (1995) 19:72–76, 78). Several different proteins, with diverse physical properties were shown to be delivered into cells by this method. Compared with commercially available monocationic lipids, protein delivery using LipofectAMINE is more efficient. Unlike other methods for protein delivery, the lipofection procedure is simple, inexpensive and effective. Proteins introduced into cells using this method are biochemically and biologically active.

Cochleates

Proteoliposome delivery vesicles can be prepared by the protein-cochleate method. Self-assembling lipid-based complexes termed cochleate are used for in vivo DNA transfer (Gould-Fogerite, S. et al., 1985, Anal. Biochem. 148:15–25; Mannino, R. J. et al., 1988, Biotechniques 6:682–690; Papahadjopoulos, D. et al., Biochim. Biophys. Acta, 1975, 394:483–491). Cochleates are prepared by calcium-induced fusion of phosphatidyl serine-cholesterol liposomes (anionic) resulting in an insoluble "jellyroll-like" structure. The layers of the jellyroll are composed of alternating sheets of negatively charged phospholipid and calcium. Gould-Fogerite, S. et al., Gene, 1989, 84:429–438, discloses a system in which proteins mediating the entry of enveloped viruses into cells are integrated in the lipid bilayer, and materials are encapsulated at high efficiency within the aqueous interior of these vesicles. Proteoliposome-mediated delivery of proteins and drugs into entire populations of cells can be achieved in culture with this approach. Material can be delivered gradually by Sendai virus glycoprotein-containing proteoliposomes or synchronous delivery can be achieved by exposing cell-bound influenza glycoprotein vesicles briefly to low pH buffer. When DNA is encapsulated, chimeric proteoliposome gene-transfer vesicles (chimerasomes), which mediate high-efficiency gene transfer in vitro and in vivo, are produced. Stable expression of a bovine papilloma virus-based plasmid in tissue-cultured cells, at 100,000 times greater efficiency than calcium phosphate precipitation of DNA, has been achieved. Stable gene transfer and expression in mice has been obtained by subcutaneous injection of chimerasomes containing a plasmid. In contrast to liposomes, cochleates are solid, multilayered, lyophilizable precipitates containing no internal aqueous space. A cochleate may be considered a fusion intermediate frozen in time. Benefits of this structure include its ability to provide protection from degradation for associated or "encochleated" molecules, the nontoxic, nonimmunogenic nature of its components, and its stability. (It can be lyophilized.) Animal studies show that oral delivery of DNA wrapped in cochleates can result in systemic responses. This was demonstrated using an 11 kb DNA plasmid encoding the env, tat, and rev genes of $HIV1_{MB}$ driven by a CMV promoter. Both oral and intramuscular administration of the DNA cochleates induced antigen-specific T helper cell responses and cytotoxic lymphocyte activity in mice.

Also useful are polycations such as asialoglycoprotein/polylysine (Wu et al., 1989, supra) wherein the conjugate includes (a) a molecule recognizing the target tissue and (b) a DNA binding compound to bind to the IpaB DNA being transfected. Polylysine is an example of a DNA binding molecule which binds DNA without damaging it. This conjugate is then complexed with plasmid DNA using known methods for transfer.

To facilitate direct delivery of genes to muscle polyvinyl-based polymer (PVP) formulation are used (Genetic Engineering News, Nov. 15, 1995, pg. 1). PVP is already used in FDA-approved injectable pharmaceutical formulations. The rationale is to enhance expression by protecting the DNA from degradation while retaining the flexibility to promote good dispersion throughout the muscle. Another desired property is interaction with DNA without condensing it into small particles, based on the expectation that condensation decreases the expression level compared to naked DNA. With a PVP formulation, a 5-to-10-fold increase was observed compared to naked DNA in the level of expression of a β-galactosidase reporter gene on direct administration to rat muscle, as well as improved DNA dispersion throughout the muscle. When a muscle-specific human growth hormone gene construct was administered to rats using the PVP formulation a significant biological effect over time was observed compared to controls.

For endothelial cell delivery, cationic lipid/colipid delivery systems may be used. For gene delivery to hepatocytes a key concern is to protect DNA in the circulation after systemic delivery before it reaches the liver. A glycopeptide delivery system has been used that incorporates a proprietary small condensing peptide (developed as an alternative to polylysine to condense and protect DNA and allow extravasation of the particles through the liver (Genetic Engineering News, Nov. 15, 1995, pg. 1). The peptide is galactosylated to target the asialoglycoprotein receptor in order to promote high affinity and specificity of gene delivery to the hepatocytes. The prototype system incorporates an endosomal release agent (lytic peptide) an hepatocyte-specific promoter. With this approach the efficiency of transfection in vitro approaches that achieved with adenovirus.

Dendrimers

Dendrimers, a macromolecular architecture, have become recognized as useful vectors for gene transfection (Haensler, J. et al., Bioconjug. Chem. 4:372–379 (1993); Tomalia, D. A., Sci. Amer. 272:62–66 (1995); Bielinska, A. et al., J. Invest. Med. 43 (Suppl. 2):330A (1995); Kukowska-Latallo, J. et al., FASEB J. 9:A409 (1995); Bielinska, A. et al., FASEB J. 9:A312 (1995)). Dendrimers are made up of precise three-dimensional branches called dendrons, with a structure that mimics the bifurcation of tree branches. For gene transfer research the focus has been on the star-burst PAMAM (polyamidoamine) family of dendrimers. These are spherical polymers (polycationic) built up like layers of an onion (each layer being referred to as a "generation"), with an outside surface of primary amines. The similar dimensions of dendrimers of seven to eight generations to histones (about 80–90 Å) led to macromolecular structures for which size, shape, surface chemistry, flexibility and topology can be controlled. They are composed of nanoscopic building blocks or modules, either passive or reactive, and they constitute a fourth new major class of macromolecular architecture (after linear, cross-linked and branched structures). Dendrimers are nonimmunogenic and appear to protect DNA against nucleases. To enhance transfection ability, an excess of dendrimer to DNA is preferred.

Proteins, Peptides and Their Functional Derivatives

The present invention is directed to compositions and methods for inducing apoptosis in a cell using IpaB as well as peptides or other functional derivatives of IpaB which have the functional activity of binding to and activating ICE or inducing apoptosis in a cell.

It will be understood that the protein useful in the methods and compositions of the present invention can be biochemically purified from a cellular source. For preparation of naturally occurring IpaB, cell cultures of Shigella possessing the plasmid which encodes IpaB or cell cultures of another microorganism transformed with this plasmid or otherwise expressing the IpaB gene, can be used. Methods for purifying proteins such as IpaB are wellknown in the art. Affinity purification methods employing ligands which bind IpaB are used, for example, immobilized antibodies specific for IpaB or immobilized ICE or an immobilized ICE homologue.

The amino acid sequence of full length IpaB protein from *S. flexneri* is presented as SEQ ID NO:2. The amino acid sequences of homologues of IpaB (SipB, YopB) from other bacterial genera are SEQ ID NO:4 (*Yersinia enterocolitica* YopB), SEQ ID NO:6 (*Yersinia pseudotuberculosis* YopB), SEQ ID NO:8 (*Salmonella typhimurium* SipB) and SEQ ID NO:10 (*Salmonella typhi* SipB).

Alternatively, because the gene encoding IpaB is known (Baudry et al., 1987, supra; Baudry et al., 1988, supra) and can be isolated or synthesized, the polypeptide can be synthesized substantially free of other proteins or glycoproteins with which it is natively associated in a heterologous prokaryotic host. IpaB can also be made in eukaryotic cells which are insensitive to the apoptotic effects of ICE activation, for example, HeLa cells.

The full length sequence of the ipaB gene is shown as SEQ ID NO:1

Alternatively, methods are well known for the synthesis of polypeptides of desired sequence on solid phase supports and their subsequent separation from the support.

Preparation of IpaB

Ipab proteins, fragments thereof and fusion proteins thereof are purified by conventional affinity chromatography using antibodies, preferably mAbs, that recognize an appropriate epitope of Ipab or other binding partners for IpaB. For example, affinity chromatography using immobilized ICE or an IpaB-binding fragment of ICE may be employed. In the case of an IpaB fusion protein, the antibody used for purification may be one which recognizes an epitope of the fusion protein partner.

Functional Derivatives

In a further embodiment, the invention provides "functional derivatives" of a IpaB. The term "functional derivative" is intended to include meant a "fragment," "variant," "analogue" "homologue" or "chemical derivative" of IpaB. A functional derivative retains at least a portion of the function of IpaB, such as (a) the activity of inducing apoptosis in a cell, (b) binding to ICE, to a fragment of ICE or to a homologue of ICE, or (c) binding to a specific anti-IpaB antibody, any of which properties permits its utility in accordance with the present invention.

A "fragment" of Ipab refers to any subset of the molecule, that is, a shorter peptide.

A "variant" of IpaB refers to a molecule substantially similar to either the entire protein or a fragment thereof. Variant peptides may be conveniently prepared by direct chemical synthesis using methods well-known in the art.

Alternatively, amino acid sequence variants of the protein or peptide can be prepared by mutations in the DNA which encodes the protein or peptide. Such variants include, for example, deletions from, or insertions or substitutions of, residues within the amino acid sequence. Any combination of deletion, insertion, and substitution may also be made to arrive at the final construct, provided that the final construct possesses the desired functional activity as defined above. Obviously, the mutations that will be made in the DNA encoding the variant peptide must not alter the reading frame and preferably will not create complementary regions that could produce secondary mRNA structure (see European Patent Publication No. EP 75,444).

At the genetic level, these variants ordinarily are prepared by site-directed mutagenesis (as exemplified by Adelman et al., *DNA* 2:183 (1983)) of nucleotides in the DNA encoding the IpaB protein or encoding a peptide fragment thereof, thereby producing DNA encoding the variant. Thereafter, the DNA is expressed in recombinant cell culture (see below). The variants typically exhibit the same qualitative biological activity as the nonvariant peptide.

A preferred group of variants of IpaB are those in which at least one amino acid residue in the protein or in a peptide fragment thereof, and preferably, only one, has been removed and a different residue inserted in its place. For a detailed description of protein chemistry and structure, see Schulz, G. E. et al., *PRINCIPLES Of PROTEIN STRUCTURE*, Springer-Verlag, New York, 1978, and Creighton, T. E., *PROTEINS. STRUCTURE AND MOLECULAR PROPERTIES*, W. H. Freeman & Co., San Francisco, 1983, which are hereby incorporated by reference. The types of substitutions which may be made in the protein or peptide molecule of the present invention may be based on analysis of the frequencies of amino acid changes between a homologous protein of different species, such as those presented in Table 1–2 of Schulz et al. (supra) and FIG. 3–9 of Creighton (supra). Based on such an analysis, conservative substitutions are defined herein as exchanges within one of the following five groups:

1. Small aliphatic, nonpolar or slightly polar residues:
   Ala, Ser, Thr (Pro, Gly);
2. Polar, negatively charged residues and their amides:
   Asp, Asn, Glu, Gln;
3. Polar, positively charged residues:
   His, Arg, Lys;
4. Large aliphatic, nonpolar residues:
   Met, Leu, Ile, Val (Cys); and
5. Large aromatic residues: Phe, Tyr, Trp.

The three amino acid residues in parentheses above have special roles in protein architecture. Gly is the only residue lacking any side chain and thus imparts flexibility to the chain. Pro, because of its unusual geometry, tightly constrains the chain. Cys can participate in disulfide bond formation which is important in protein folding. Tyr, because of its hydrogen bonding potential, has some kinship with Ser, Thr, etc.

Substantial changes in functional or immunological properties are made by selecting substitutions that are less conservative, such as between, rather than within, the above five groups, which will differ more significantly in their effect on maintaining (a) the structure of the peptide backbone in the area of the substitution, for example, as a sheet or helical conformation, (b) the charge or hydrophobicity of the molecule at the target site, or (c) the bulk of the side chain. Examples of such substitutions are (a) substitution of gly and/or pro by another amino acid or deletion or insertion of gly or pro; (b) substitution of a hydrophilic residue, such as ser or thr, for (or by) a hydrophobic residue, such as leu, ile, phe, val or ala; (c) substitution of a cys residue for (or by) any other residue; (d) substitution of a residue having an electropositive side chain, such as lys, arg or his, for (or by) a residue having an electronegative charge, such as glu or asp; or (e) substitution of a residue having a bulky side chain, such as phe, for (or by) a residue not having such a side chain, such as gly.

Preferred deletions and insertions, and substitutions, according to the present invention, are those which do not produce radical changes in the characteristics of the IpaB protein or peptide molecule. However, when it is difficult to predict the exact effect of the substitution, deletion, or insertion in advance of doing so, one skilled in the art will appreciate that the effect will be evaluated by routine screening assays which are described in more detail below. For example, a change in the immunological character of the protein or peptide molecule, such as binding to a given antibody, is measured by a competitive type immunoassay. For determining whether a particular functional derivative has the requisite biological activity, an appropriate bioassay is used to test such derivative. A preferred assay for apoptosis utilizes terminal deoxynucleotidyl transferase-mediated dUTP nick end labeling ("TUNEL") (Gavrieli, Y. et al., *J. Cell Biol.* 119:493–501 (1992)). In this method, the dUTP is labeled with, for example, biotin or digoxigenin. This technique specifically detects apoptotic cells by utilizing the transferase enzyme to incorporated labeled, e.g., biotinylated, nucleotides into the fragmented DNA or apoptotic cells. The labeled cells are visualized by reaction with the appropriate binding partner for the label. In the case of biotin, avidin peroxidase may be used with a suitable substrate for peroxidase. This method can be used with cells in culture or tissues from an animal. See, for example, Smale, G. et al., *Exp. Neurol.* 133:225–230 (1995); Geng Y. J. et al., *Amer. J. Pathol.* 147:251–266 (1995); Strater, J. et al., *Histochem. Cell Biol.* 103:157–160 (1995)). Furthermore, the functional derivative can be tested for its ability to compete.

A "homologue" of IpaB refers to a protein which occurs naturally in a genus other than Shigella, which includes other bacterial genera as well as animal genera including mammals. Homologues, as used herein typically share about 50% sequence similarity at the DNA level or about 18% sequence similarity in the amino acid sequence. Preferred homologues are YopB and SipB from Yersinia and Salmonella species as described above. The term "homologue" is not intended to be limited to structural homologues as discussed above, but also includes a functional homologue which is a molecule which, while not sharing formal structural homology with IpaB nevertheless has the capacity to bind to ICE or an ICE isoform (α, β, γ, δ or ε; Alnemri et al, *J. Biol. Chem* 270:4312–4317 (1995)) or to an ICE homologue and, thereby, to stimulate apoptosis in a cell. Examples of such ICE homologues to which IpaB (or a functional derivative thereof) can bind include, but are not limited to, Mch2, Mch3, TX protease, ICErel-II, Ich-1, Ich-2 and Ced3 (which are referenced in Example VII, below).

An "analogue" of IpaB refers to a non-natural molecule substantially similar to either the entire molecule or a fragment thereof.

A "chemical derivative" of IpaB contains additional chemical moieties not normally a part of the peptide. Covalent modifications of the peptide are included within the scope of this invention. Such modifications may be introduced into the molecule by reacting targeted amino acid residues of the peptide with an organic derivatizing agent that is capable of reacting with selected side chains or terminal residues. Additionally, modified amino acids or chemical derivatives of amino acids of IpaB or fragments thereof, according to the present invention may be provided, which polypeptides contain additional chemical moieties or modified amino acids not normally a part of the protein. Such derivatized moieties may improve the solubility, absorption, biological half life, and the like. Moieties capable of mediating such effects are disclosed, for example, in *Remington's Pharmaceutical Sciences,* 16th ed., Mack Publishing Co., Easton, Pa. (1980).

A preferred type of chemical derivative is a peptidomimetic agent which may be an unnatural peptide or a non-peptide agent which has the stereochemical properties of an IpaB peptide such that it has the binding activity or biological activity of IpaB. Peptidomimetic compounds, either agonists, substrates or inhibitors, have been described for a number of bioactive peptides such as opioid peptides, VIP, thrombin, HIV protease, etc. Methods for designing and preparing peptidomimetic compounds are known in the art (Kempf D J, *Methods Enzymol* 241:334–354 (1994); Hruby, V. J., *Biopolymers* 33:1073–82 (1993); Wiley, R. A. et al., *Med. Res. Rev.* 13:327–384 (1993); Claeson, G., *Blood Coagul. Fibrinolysis* 5:411–436 (1994), which references are incorporated by reference in their entirety). These methods are used to prepare IpaB or ICE peptidomimetic which possess at least the binding capacity and specificity of the protein and preferably also possess the biological activity, either bind to or bind to and compounds, using knowledge of peptide chemistry and general organic chemistry available to those skilled in the art.

Production of IpaB and Fusion Proteins that Induce Apoptosis

IpaB may be purified from prokaryotic host cells using conventional biochemical techniques, or produced recombinantly in either prokaryotic or genetically modified eukaryotic cells using methods well-known in the art (Sambrook, J. et al., *MOLECULAR CLONING: A LABORATORY MANUAL,* 2nd Edition, Cold Spring Harbor Press, Cold Spring Harbor, N.Y., 1989, which reference is hereby incorporated by reference in its entirety).

Fusion proteins representing different polypeptide regions in IpaB may be used to identify regions of the protein that have the desired functional activity (binding to ICE, inducing apoptosis, etc.). When combined with the polymerase chain reaction (PCR) method, it is possible and expedient to express in bacteria nearly any selected region of the protein.

To facilitate unidirectional subcloning of the PCR products, sense and antisense oligonucleotides have been designed to include BamH1 recognition sequences at the 5' end and EcoR1 recognition sequences at the 3' end, respectively; appropriately digested PCR products are then be ligated directly into a vector (such as the pGEX-2T vector).

The pGEX vector is preferred because the glutathione-S-transferase (GST) fusion proteins can be purified rapidly by binding to glutathione-agarose beads. In addition, the portion of the fusion protein representing the GST can be cleaved with thrombin and the engineered polypeptide can generally be recovered free of the GST protein which can be removed using glutathione-agarose beads (Ausubel, F. M., et al., 1990, *CURRENT PROTOCOLS IN MOLECULAR BIOLOGY,* John Wiley & Sons, New York.

A GST-IpaB fusion protein is preferably prepared as described in the Examples, below. In this embodiment, ipaB is preferably amplified by PCR from p179 (Maurelli, A. T. et al., *Infect. Immun.* 49:164–171 (1985)) and ligated into the expression vector pGEX-KG (Guan, K. L. et al., *Anal Biochem* 192:262–267 (1991)) EcoRI site to generate a GST-IpaB fusion product. The product can be expressed in an appropriate host cell, for example a bacterial host, by use of an inducer which activates the promoter of the fusion protein construct, in the present case, IPTG. Bacterial cultures are then lysed by sonication and the fusion protein obtained from the lysates either by affinity chromatography using immobilized glutathione or immobilized anti-IpaB antibody.

Having now generally described the invention, the same will be more readily understood through reference to the following examples which are provided by way of illustration, and are not intended to be limiting of the present invention, unless specified.

EXAMPLE I

In Vivo Apoptosis in *Shigella flexneri* Infections

Since apoptosis appears to play an essential role in the pathogenesis of dysentery, the present inventors and their colleagues tested whether Shigella induces apoptosis in vivo. *S. flexneri* invasiveness and virulence are encoded in a plasmid. Strains cured of this plasmid are completely non-invasive and avirulent (Sansonetti, P. J. et al., *Infect. Immun.* 35:852–860 (1982).)

Methods

The histopathology of shigellosis can be faithfully reproduced in the rabbit ligated ileal loop model (Sansonetti, P. J. et al., *Vaccine* 9:416–422 (1991); Sansonetti, P. J. et al. *Vaccine* 7:443–450 (1989)). To evaluate the extent of apoptosis induction in vivo, rabbits were injected intraluminally with either saline solution or one of three different Shigella strains: (1) the wild type strain M90T, (2) the avirulent derivative BS 176 and (3) BS 15, a transformant of BS176 expressing the *E. coli* adhesin AFR-1. This strain carried a plasmid that encodes the AFR1 (Cantey, J. R. et al.,*J. Infect. Dis.* 135:454–462 (1977)) adherence pilus of the rabbit-specific enteropathogenic *E. coil* strain RDEC-1 (Cheney, C. P. et al.,*J. Infect. Dis.* 147:711–723 (1983)). The AFR1 pilus allows infection of the follicle-associated epithelium and the colonization of the follicular tissue (Inman, L. R. et al., *J. Clin. Invest.* 74:90–95 (1984)). Therefore, BS15 serves as a control for a Shigella that can colonize Peyer's patches but does not harbor the virulence plasmid. Histological sections from these rabbits were labeled using TdT dUTP nick end labeling (TUNEL; Gavrieli et al., supra). This technique labels cells with fragmented DNA, a unique feature of apoptosis.

Results

There were striking differences in the number of apoptotic cells in loops infected with the virulent or avirulent strains of Shigella. Four hours after infection with M90T there were numerous labeled cells in lymphoid follicles. In contrast, there were very few labeled cells in lymphoid follicles infected with BS176. The DNA fragmentation label was restricted to the nuclei. Similarly, 8 hrs after infection, large numbers of apoptotic cells were seen in lymphoid follicles infected with M90T, but only a few cells underwent programmed cell death in lymphoid follicles infected with BS176. At both 4 and 8 hours after infection, apoptotic cells were evenly distributed throughout the lymphoid follicle.

DNA fragmentation was restricted to Peyer's patches after infection with Shigella, as very few labeled cells were observed in the villous intestine of loops infected with either the BS176 or M90T strains.

Infections with BS 15 or M90T result in comparable bacterial invasion of lymphoid follicles. There were $9 \times 10^5$ ($\pm 0.7 \times 10^5$) colony forming units (CFU) per $cm^2$ in BS15-infected Peyer's patches and $15 \times 10^5$ ($\pm 2 \times 10^5$) $CFU/cm^2$ in M90T infected tissue compared with only $0.2 \times 10^5$ ($\pm 1 \times 10^5$) $CFU/cm^2$ in BS176 infections. BS15 did not induce cells to undergo apoptosis, demonstrating that programmed cell death activation is specific to Shigella pathogenesis and that the presence of a large number of gram negative bacteria in the Peyer's patch does not by itself induce apoptosis.

The number of cells undergoing programmed cell death were counted using a computer interfaced mapping microscope. There were 30-fold more cells with fragmented DNA in the Peyer's patches infected with M90T, 1205±432.5 (standard deviation) $cells/mm^2$ compared to loops injected with saline (35±8 $cells/mm^2$) at 8 hours. The number of apoptotic cells in loops infected with either BS176 or BS15, were statistically indistinguishable from loops injected with saline. Four hours after infection, there were 1035±466 apoptotic $cells/mm^2$ cells in lymphoid follicles infected with M90T and only 361±96 apoptotic $cells/mm^2$ in lymphoid follicles infected with BS176. Between 200 and 300 cells/mm were observed in Peyer's patches of animals that were sacrificed 2 hours after infection irrespective of whether the loops were infected with M90T or BS176.

To assess the statistical significance of the number of labeled cells in infections with the different strains, three lymphoid follicles were counted in 7 independently infected loops (total: 21 follicles) with M90T and three lymphoid follicles in 5 infected loops (total: 15 follicles) with BS176 8 hrs after infection. The mean number of apoptotic cells in loops infected with M90T was 847 $cells/mm^2$, whereas the mean number of labeled cells in follicles infected with BS176 was 189 $cells/mm^2$. The difference between these numbers is statistically significant (p=0.0027; Mann-Whitney U test)

EXAMPLE II

Identification of Apoptotic Cells In Vivo

In vitro, Shigella-induced apoptosis was first identified in macrophages (Zychlinsky, A. et al., *Nature* 358:167–168 (1992)). In view of the large amount of apoptotic cells in M90T infections, studies were done to identify the type of cells that undergo apoptosis in tissue sections employing double-labeling with rabbit-specific cell markers and the DNA binding dye PI. PI permits visualization of typical apoptotic nuclear morphology which consists of shrinkage, chromatin condensation, and marginalization of the DNA.

Tissue sections were labeled with the antibody RAM-11 (Tsukada, T. et al., *Arteriosclerosis* 6:601–613 (1986)), anti-CD4 and anti-immunoglobulin A (IgA) to identify macrophages, helper T lymphocytes and B lymphocytes, respectively. Cells labeled with RAM-11 presented normal nuclear morphology in Peyer's patches infected with BS176. In follicles of loops infected with M90T, there were many RAM-11$^{30}$ cells that contained multiple apoptotic nuclei. These cells were thought to be macrophages that had phagocytized other apoptotic cells making it is difficult to determine whether the macrophages themselves are undergoing apoptosis. Other microscopic fields contained RAM-111$^{30}$ cells having only one apoptotic nucleus. These cells were likely macrophages undergoing apoptosis. In the same section, some cells having apoptotic morphology were not labeled by this antibody, indicating that other cell types were also susceptible to Shigella cytotoxicity.

Both helper T cells and B cells appeared normal in follicles infected with BS176. Apoptotic nuclei in cells labeled by anti-CD4 or anti-IgA were identified in follicles infected with M90T.

It is not known whether the induction of apoptosis in B cells and T cells in the course of Shigella infection is directly caused by bacterial invasion or pathogenicity is secondary to factors released by other cells such as macrophages. The deletion of these cells from the mucosal immune system could contribute to difficulties in immunizing against shigellosis with live attenuated vaccine strains.

The results show that virulent Shigella strains induce apoptosis in vivo. It was previously found that, during the apoptotic process, activated macrophages release IL-1, but not IL-6 or tumor necrosis factor (Zychlinsky, A. et al., *J. Clin.Invest.*, supra). Blocking the effects of IL-1 abrogates the inflammatory response during Shigella infection (Sansonetti el al., 1995, supra).

Based on the results presented herein, it was concluded that induction of macrophage apoptosis by Shigella was an important contributing factor in the initiating pathogenesis of dysentery in vivo. A proposed sequence of events in the initial stages of shigellosis is as follows.

a. translocation of Shigella from the lumen to the lamina propria of the colon by M-cells, b. infection of macrophages, T cells and B cells in the lymphoid nodules, and c. induction of macrophage apoptosis, with concomitant release of IL-1, which in turn initiates the acute inflammatory response.

EXAMPLE III

IpaB Localizes in the Cytoplasm

To determine the cellular localization of secreted IpaB in macrophages, the inventors infected cells with either the wild type strain of *S. flexneri* M90T (Sansonetti, P. J. et al., *Infect. Immun.* 35:852–860 (1982)) or BS176, an isogenic stain that lacks the pathogenicity plasmid. IpaB was localized by indirect immunofluorescence using an anti-IpaB antibody.

A. Methods

J774 cells were seeded on coverslips and infected with *S. flexneri* strains as described (Clerc, P. L. et al., *Infect. Immun.* 55:521–527 (1987)). Twenty min after infection, the cells were washed of extracellular bacteria and fixed in paraformaldehyde. The cells were permeabilized with cold acetone, then blocked and incubated first with an anti-IpaB rabbit polyclonal antibody (provided by Dr. A. Phalipon, Institute Pasteur), and then with a secondary fluoresceinated goat anti-rabbit immunoglobulin (Ig) antibody.

The slides were then stained with the DNA-binding dye propidium iodide (PI) or incubated with anti-LAMP-1 rat monoclonal antibody (mAb) which detects lysosomes and late endosomes (Developmental Studies Hybridoma Bank, NIH) (Chen, J. W. et al., *Arch. Biochem. Biophys.* 239:574–586) followed by a Texas Red-labeled anti-rat Ig antibody. Slides were analyzed using a Molecular Dynamics laser scanning microscope. The optical sections were filtered with an alpha filter, and reconstructed in 3-D projections. IpaB was visualized by indirect immunofluorescence as green color (fluorescein). Lysosomes and late endosomes were detected with indirect immunofluorescence as red color (Texas red).

In J774 cells infected with the non-pathogenic, plasmid-cured strain BS176, ipaB deletion mutant ($\Delta$ipaB) or wild type strain M90T D) both macrophage nuclei and the bacteria were stained with PI.

Using double labeling with anti-IpaB and the anti-LAMP-1 antibodies, IpaB was detected in M90T infected cells both in close association with bacteria as well as free in the cytoplasm. Most of the IpaB was free in the cytoplasm, as evidenced by little colocalization with the lysosomal marker LAMP-1. It was concluded that IpaB is mostly excluded from the late endosomal and lysosomal compartments.

Ipab was not detectable in cells infected with either the plasmid-cured BS176 strain (which lacks the pathogenicity plasmid) or $\Delta$ipaB, the deletion mutant for IpaB (Menard, R. et al., surpra). In cells infected with the $\Delta$ipaB strain the late endosome and lysosome compartments were clearly labeled but no IpaB immunoreactivity was detected.

EXAMPLE IV

IpaB Provokes Apoptosis

To investigate whether IpaB is sufficient to provoke programmed cell death, the inventors microinjected a purified fusion protein comprising glutathione S-transferase (GST) fused to IpaB (GST-IpaB) into peritoneal macrophages. This fusion protein complements the $\Delta$ipaB mutant for cell invasion and cytotoxicity (see Example VIII), demonstrating that GST-IpaB is a functional protein. After microinjection, the induction of apoptosis was assayed by PI uptake.

A. Methods

To produce GST-IpaB, ipaB was amplified by PCR from p179 (Maurelli, A. T. et al., *Infect. Immun.* 49:164–171 (1985)) and ligated into the expression vector pGEX-KG (Guan, K. L. et al., *Anal Biochem* 192:262–267 (1991)) EcoRI site to generate glutathione S-transferase (GST)-IpaB fusion. This plasmid contains the inducible $\beta$-gal promoter. The $\Delta$ipaB strain containing either pGEX-KG-ipaB or, as a control, the plasmid pGEX-KG, was induced with IPTG for 3 hours. Bacterial cultures were then lysed by sonication, and the lysates were incubated with glutathione-Sepharose beads. The beads were washed several times with phosphate buffered saline (PBS), and GST-IpaB or GST bound to the beads was eluted by glutathione.

Macrophages were isolated from a population of peritoneal cells from Balb/c mice by adherence to glass coverslips. The samples were loaded into glass capillary micropipets made with an automatic P80/PC micropipet puller (Sutter Instruments Co.). The monolayer of macrophages was microinjected, in a volume of $0.5$–$1\times 10^{-11}$ ml) with coded test samples (200–350 $\mu$/ml) using an Eppendorf microinjection system. After microinjection, cells were incubated at 37° C. for 4–6 hours and stained with PI in PBS without fixation. For quantification, the results were the average of at least 4 separate experiments consisting of at least 600 microinjections.

Macrophages were microinjected with bovine serum albumin (BSA) as one control, GST as a second control, or GST-IpaB. Only apoptotic cells take up PI. Apoptotic cells were scored and photographed by UV microscopy to observe PI staining and by phase contrast microscopy to observe cellular morphology.

Similar experiments were conducted with cells of two murine cell lines, NIH3T3 cells and L929 fibroblasts.

Results

Evaluation of the uptake of PI and the cellular morphology, indicated that, in general, many more macrophages injected with GST-IpaB underwent apoptosis than cells injected with GST or BSA.

GST-IpaB killed macrophages efficiently (71.8%±7.2 dead PI$^+$ cells) accompanied by morphological changes typical of apoptosis. In contrast, GST (at the same concentration were not cytotoxic. (17.5%±6.5 and 8.8%±1.3 dead cells, respectively).

The ability of IpaB to produce apoptosis upon microinjection into cells was evaluated in two murine cells lines in culture, NIH3T3 and L929. Apoptosis was assessed as nuclear degeneration measured by PI uptake. Control microinjections included BSA and GST. The results are shown below. Numbers in parentheses indicate standard errors of the mean of 3 replicate determinations.

| Cell line | Test Material | % PI+ Cells |
|---|---|---|
| NIH-3T3 | BSA | 4.8 (3.2) |
| | GST | 10.0 (4.9) |
| | IpaB | 61.2 (11.0) |
| L929 | BSA | 3.4 (0.5) |
| | GST | 7.6 (1.6) |
| | IpaB | 58.5 (13.7) |

EXAMPLE V

IpaB is Sufficient to Induce Apoptosis

The inability to obtain macrophages that express IpaB is further evidence supporting a direct role for IpaB in macrophage apoptosis. The inventors attempted to express IpaB in macrophages by infecting murine J774 cells with a retroviral vector (pSRIMSVTKneo) (Sawyers, C. L. et al, Cell 77:121–131 (1994); Muller, A. J. et al., Molec. Cell. Biol. 11:1785–1792 (1991)) carrying ipaB. This retrovirus is appropriately trophic for these target cells. In repeated experiments, the inventors were unable to obtain geneticin-resistant colonies such J774 cells infected with the retroviral vector encoding ipaB, whereas geneticin-resistant colonies were observed when J774 cells were infected with the vector alone.

As an additional control, HeLa cells, which are insensitive to Shigella cytotoxicity, were infected with the above retroviral vector with and without the ipaB gene. As expected, geneticin-resistant colonies were obtained in both types of virus-infected HeLa cells. Taken together, these results indicate that IpaB is sufficient to induce apoptosis.

EXAMPLE VI

IpaB interacts with Interleukin-1-Converting Enzyme

The inventors tested whether IpaB interacts with macrophage proteins.
Methods

Figure 2:
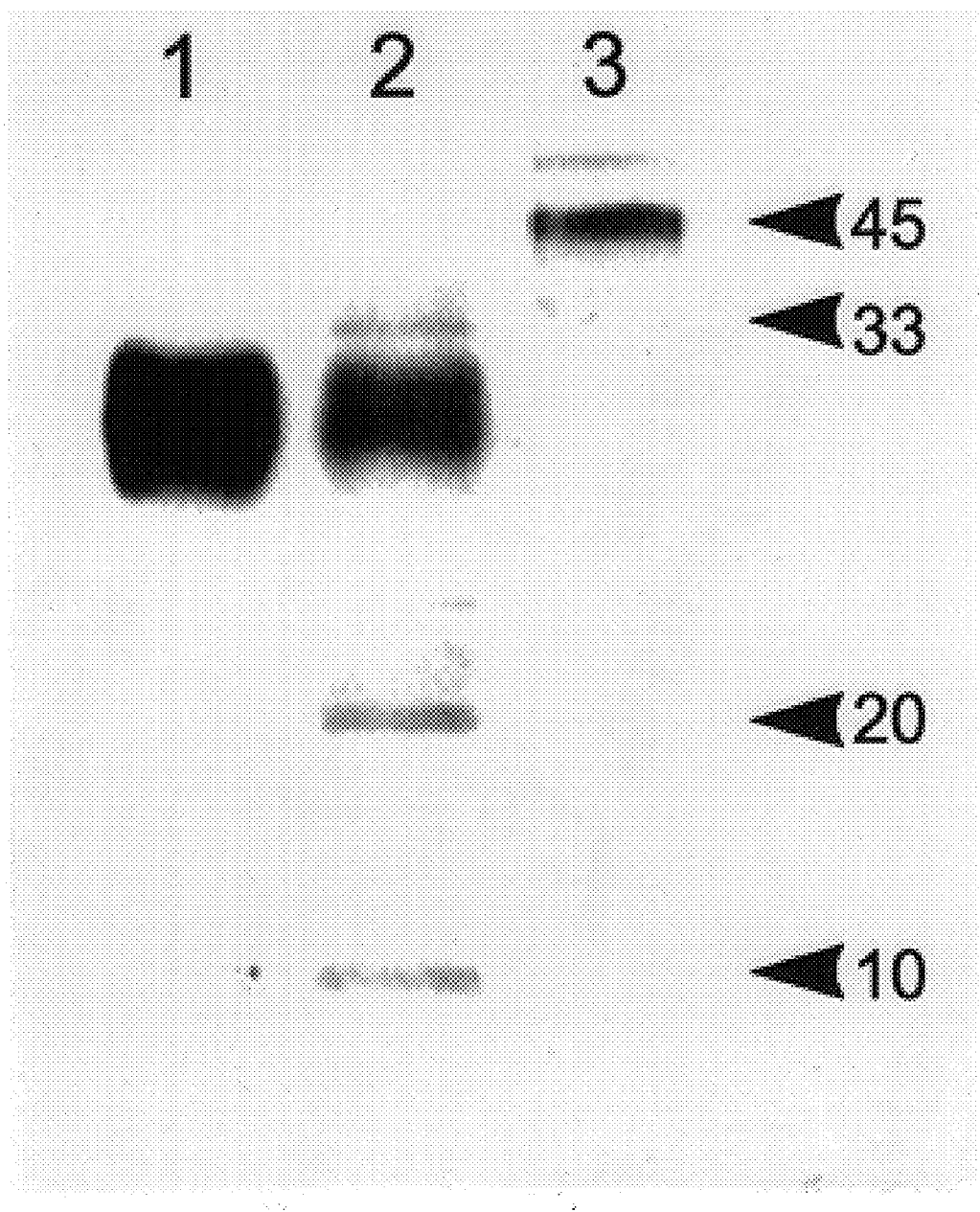

For experiments the results of which are summarized in FIGS. 1 and 2. J774 cells were first starved of methionine (met) and then labeled for 3 hrs with $^{35}$S-met in met-free RPMI medium containing 5% FCS and 30 µg/ml gentamicin. Thereafter, the cells were washed and lysed in lysis buffer (PBS with 1% Triton X-100 and 1 mM phenylmethyl sulfonyl fluoride (PMSF; a proteinase inhibitor), 10 µg/ml aprotinin, 10 µg/ml pepstatin A and 5 mM EDTA). Supernatant free of nuclei supernatant was used for the assay.

GST- or GST-IpaB-coupled beads were prepared as described above (but without glutathione elution). Beads were incubated with the $^{35}$S-labeled J774 lysate at 4° C. for 2 hours and washed with RIPA buffer (1% Triton X-100, 0.5% deoxycholic acid, 0.1% SDS, 50 mM Tris, pH 7.5, 0.15M NaCl). The proteins bound to the beads were resolved in 5–15% SDS-PAGE gradient gel and exposed to a Phosphorimager.

Figure 3:
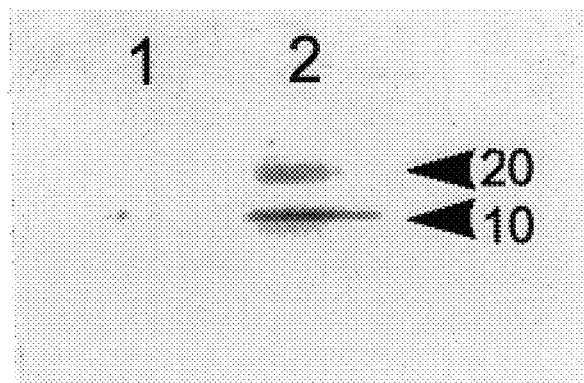

For experiments the results of which are shown in FIG. 3, $10^8$ J774 cells were infected with M90T or BS176 as described (Clerc, P. L. et al., supra) and lysed 40 min after infection. The lysate was precleaned using IgG-agarose beads at 4° C. overnight before incubation with IgG-agarose beads crosslinked with the anti-IpaB mAb H16 (Barzu, S. et al., Infect. Immun. 61:3825–3831 (1993)). The beads were then washed with RIPA buffer several times and assayed by Western blot. Five mg of the mAb were crosslinked to 1 ml of IgG-agarose for 30 min at room temperature using 5 µg/ml dimethyl pimelimidate+2HCl in a sodium borate solution as a linker .

Figure 4:
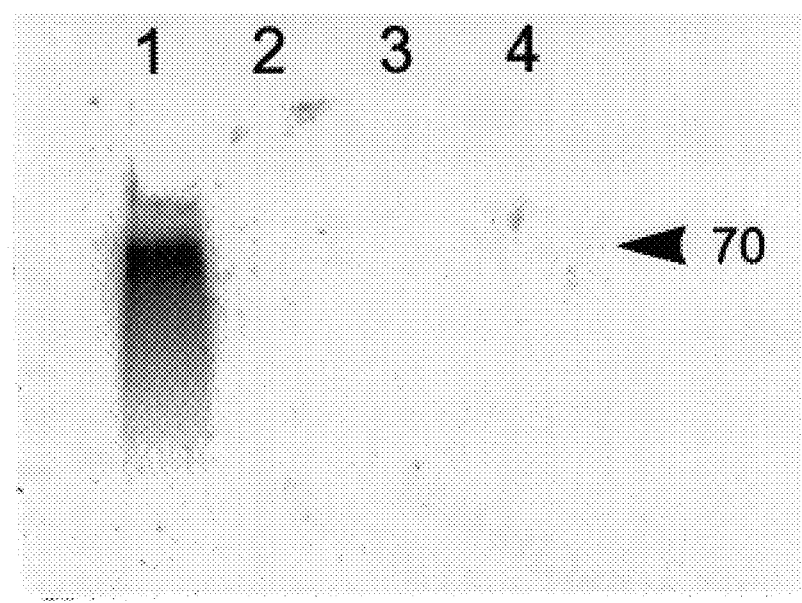
FIG. 4 shows results of ligand blotting of ICE with $^{32}$P-labeled IpaB. Equal amounts of purified GST-ICE (lane 1 and 3) and GST (lane 2 and 4) were resolved by SDS-PAGE and transferred onto nitrocellulose. After blocking, the filters were probed with 1 1 g/ml $^{32}$P-Tag-GST-IpaB (lane 1 and 2) or $^{32}$P-Tag-GST (lane 3 and 4). $^{32}$P-Tag-GST-IpaB bound to GST-ICE (MW, 70 kDa) but not GST.

For experiments the results of which are shown in FIG. 4, IpaB was inserted into EcoRI site of pGSTag (Ron, D. et al., supra) (provided by Dr. D. Ron, New York University Medical Center) which contains a high affinity phosphorylation site of protein kinase A (PK-A). The fusion protein products of these plasmids, GST-IpaB-Tag and GST-Tag, were labeled by phosphorylation catalyzed by PK-A (Promega) using $\gamma^{32}$P-ATP in a buffer of 2 mM DTT, 50 mM potassium phosphate (pH 7.15), 10 mM MgCl$_2$, 5 mM NaF. This labeling was carried out for 30 min at 30° C.

Labeled proteins were purified through an NAP-25 column. Proteins on the SDS-PAGE were transferred to nitrocellulose and blocked in 20 mM Tris, 100 mM NaCl, 1 mM EDTA, 1 mM DTT, 0.5% Triton X-100 and 5% milk. The blocked nitrocellulose membranes were probed with the $^{32}$P-labeled protein described above for 1 hour at room temperature and were washed with blocking buffer which included 300 mM NaCl (no milk present).

The full length ICE cDNA (provided by Dr. Yuan, Harvard University) was first cloned into pUC19 into the BamHI and SalI site by blunt end ligation and shuttled to the pGEX-KG SmaI site. A GST-ICE fusion protein was purified as described for GST-IpaB.
Results Proteins from macrophage lysates were purified using GST-IpaB as a ligand. Four peptides with molecular weights of 45, 33, 20 and 10 kDa, respectively, were identified when radiolabeled J774 lysates were passed through a GST-IpaB column. These peptides could not be detected when the lysates were passed through a GST column (FIG. 1). The molecular weights of these four peptides are the same as those of the known forms of ICE. The ICE precursor is a 45 kDa peptide that is first cleaved to a p32 intermediate and finally cleaved into p20 and p10 which form the mature protein (Thornberry, N. A. et al., Nature 356:768–774 (1992)).

To establish whether any or all of these proteins were ICE, immunoblotting was performed with an anti-ICE antibody. Anti-ICE antibodies recognized three of the four IpaB binding proteins P33, P20 and P10 (FIG. 2). P45 was not detected in immunoblots, possibly because this peptide has lower affinity to IpaB than do the other ICE peptides, or because P45 is degraded during the purification process.

To test whether Ipab binds to ICE subunits in vivo, the inventors immunoprecipitated IpaB from M90T infected J774 cells and found that ICE P10 and P20 molecules were coprecipitated with IpaB (FIG. 3).

These results indicated that IpaB complexes with mature ICE in vivo.

To determine whether IpaB bound directly to ICE or whether the binding required other factors, ligand blot assays were performed. The GST-IpaB protein was tagged with a phosphorylation site (Ron, D. et al., Biotechniques 13:866–869 (1992)) and was labeled with $^{32}$P as described above. A GST-ICE fusion protein was purified. $^{32}$P-GST-IpaB-Tag bound to GST-ICE but not to GST while $^{32}$P-GST-Tag bound neither GST-ICE nor GST (FIG. 4), demonstrating direct binding of IpaB to ICE.

EXAMPLE VII

ICE Activity is Required for Shigella Induced Apoptosis

ICE triggers apoptosis when overproduced in transfected cell lines (Miura, M. et al., *Cell* 75:653–660 (1993)), a process which requires its protease activity (Wang, L. et al., *Cell* 78:739–750 (1994); Enari, M. et al., *Nature* 375:78–81 (1995)). The present inventors found that ICE activity was necessary for *S. flexneri* induced apoptosis in macrophages.

Methods

Figure 5:
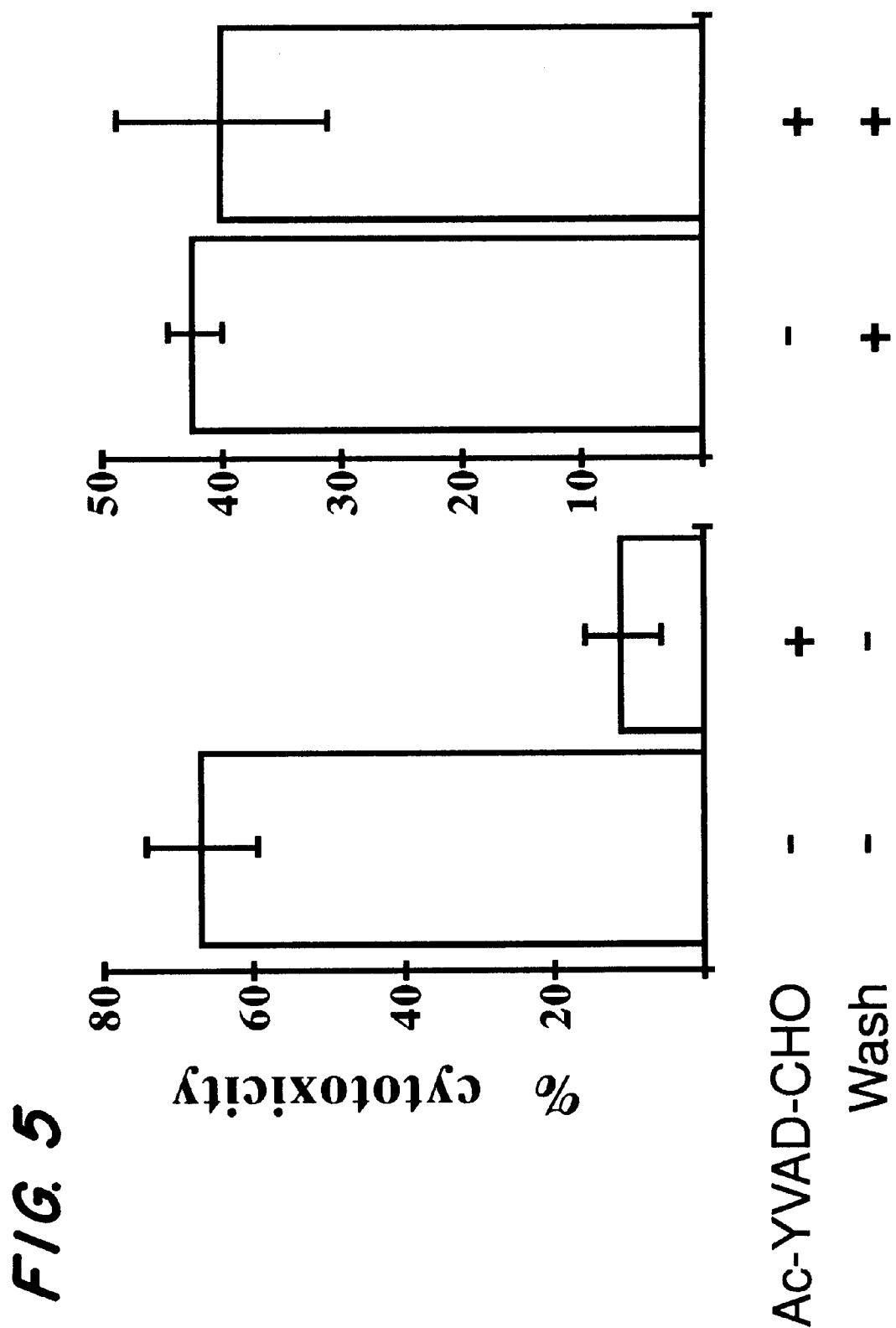
FIGS. 5 and 6 show the inhibition of apoptosis and ICE activity in macrophages with an ICE specific inhibitor.

In the studies the results of which are shown in FIG. 5, $2 \times 10^4$ J774 or peritoneal macrophage cells were seeded onto 96-well plates 18 hours before infection with M90T at a multiplicity of infection of 25 bacteria per cell (Clerc, P. L. et al., supra). Two hours after infection, supernatants of the infected macrophages were assayed for LDH using the Cytotox96® kit (Promega) according to the manufacture's instructions. The percent cytotoxicity was calculated as:

$$100 \times \frac{(\text{experimental release} - \text{spontaneous release})}{(\text{total release} - \text{spontaneous release})}$$

where spontaneous release is the amount of LDH activity in supernatants of cells not infected and total release is the LDH activity in macrophage lysates. ICE inhibitor was added 1 h before infection at a concentration of 25 µg/ml.

Figure 6:
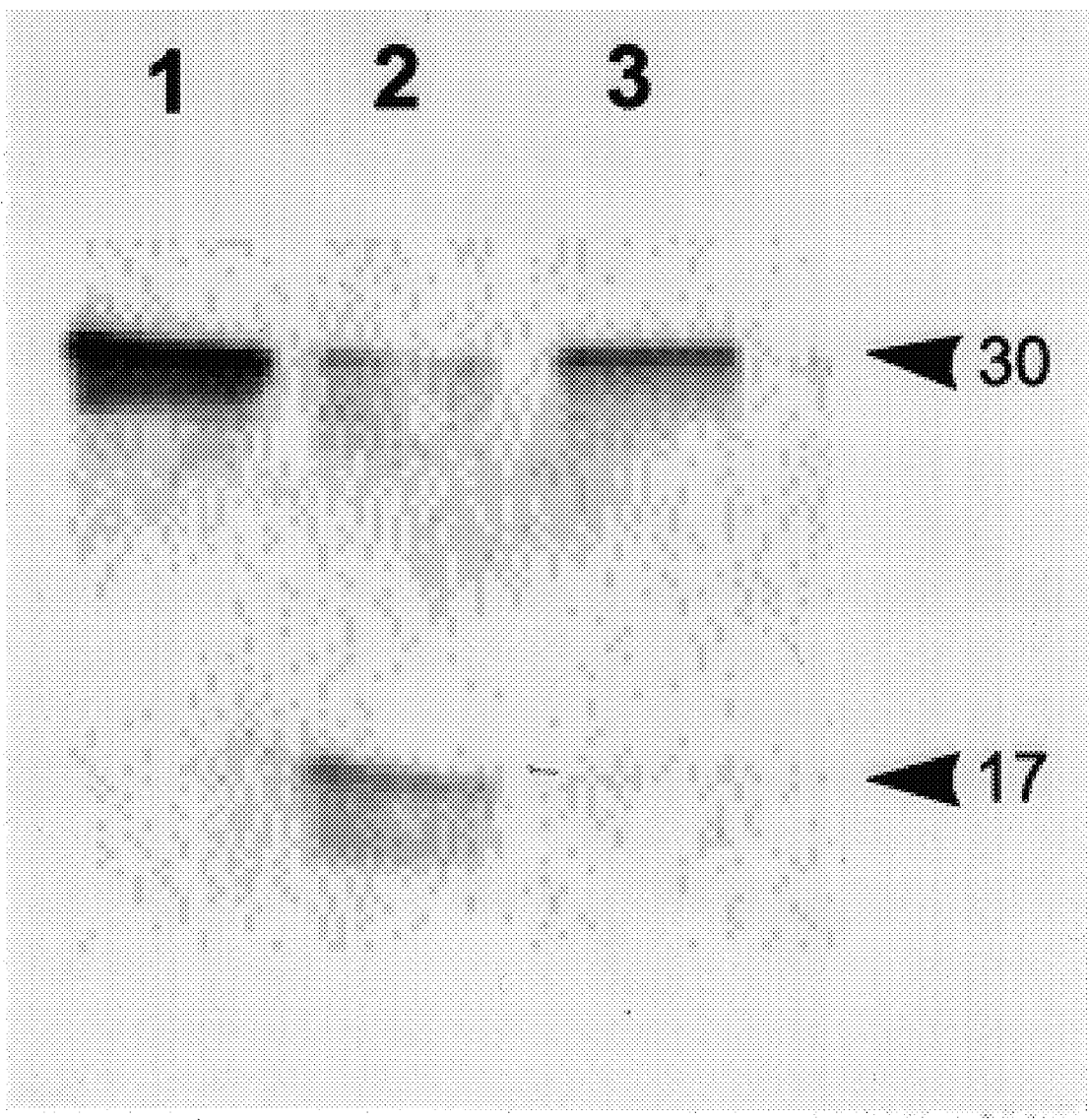

In the studies the results of which are shown in FIG. 6, peritoneal macrophages were infected with different strains of *S. flexneri* (Clerc, P. L. et al., supra) and supernatants of the infected macrophages were resolved on SDS-PAGE and analyzed by Western blotting. The competitive inhibitor of ICE was Ac-YVAD-CHO (Bachem Bioscience)

Results

In the presence of the ICE-specific inhibitor Ac-YVAD-CHO (Nicholson, D. W. et al., *Nature* 376:37–43 (1995)), *S. flexneri*-induced cell death of J774 cells was inhibited by 81.5%. This inhibition was reversed by washing away the inhibitor (FIG. 5). Similar results were obtained using peritoneal macrophages.

The inhibition of ICE was confirmed by IL-1β cleavage analysis in peritoneal macrophages (FIG. 6). The specific substrate of ICE, the 31 kDa IL-1β, was cleaved to the 17 kDa mature form in control macrophages infected with wild type *S. flexneri* strain M90T but not with macrophages pre-treated with Ac-YVAD-CHO before infection.

Studies were done to determine whether the ICE homologue CPP32 (Nicholson, D. W. et al., supra; Fernandes-Alnemri, T. et al., *J. Biol. Chem.* 269:30761–30764 (1994); Tewari, M. et al., *Cell* 81:801–809 (1995)) was also involved in Shigella-induced apoptosis. The inventors tested whether the CPP32- specific substrate, Poly(ADP-ribose) polymerase (PARP) (Tewari, M. et al, supra) was cleaved during infection. Anti-PARP antibody was provided by G. Poirer, University of Laval, Canada). No cleavage of PARP was detected at any of several time points after infection with Shigella.

The results indicate that IpaB binds to ICE rather than to this particular ICE homologue. This is supported by the apparent molecular weight of the precursor, the cleavage of IL-1β and the absence of PARP cleavage (Tewari, M. et al., supra) and, most importantly, the inhibition of *S. flexneri*-induced apoptosis with a specific inhibitor of ICE enzymatic activity.

However, Ipab may bind to ICE isoforms (α, β, γ, δ or ε; Alnemri et al., *J. Biol. Chem* 270:4312–4317 (1995)) or to ICE homologues known in the art or yet to be discovered. Such ICE homologues include the mammalian homologues Mch2 (Fernandes-Alnemri, T. et al., *Cancer Res.* 55:2737–2742 (1995)), Mch3 (Fernandes-Alnemri et al., *Cancer Res.* 55:6045–6052 (1995)), TX protease (Faucheu, C. et al., *EMBO* 14:1914–1922 (1995)), ICErel-II (Munday, N. A. et al., *J. Biol. Chem.* 270:15870–15876 (1995)), Ich-1 or Nedd2 (Wang, L. et al, supra; Kumar, S. et al., *Genes Dev.* 8:1613–1626 (1994)), Ich-2 (Kamens, *J. Biol. Chem,* 1996, in press) and the non-mammalian homologue Ced3 (Yuan, *Cell* 75:641–652 (1993)).

EXAMPLE VIII

IpaB Function in Mutants is Complemented by IpaB-GST Fusion Protein and by Salmonella SipB, an IpaB Homologue Studies were done which showed that the IpaB-GST fusion protein and (in a separate study) the Salmonella homologue of IpaB, SipB, complemented invasion and cytotoxicity of ΔipaB mutants.

For the invasion assay, HeLa cells were infected with different strains of *S. flexneri* for 1 hr, washed and incubated in the presence of gentamicin for 2 hr. The cells were then lysed in Triton buffer. Intracellular bacteria were plated on agar medium, grown overnight and the colonies were counted.

For determination of cytotoxicity, macrophages were infected with different strains of *S. flexneri* at a multiplicity of infection (moi) as shown (either 100, 50 or 25 bacteria/cell. LDH release was monitored after 3 hr of infection. The results are shown below.

| Strain | moi | Invasion (# colonies) | Cytotoxicity (% LDH released) |
|---|---|---|---|
| M90T | 100 | 7200 | 76 |
| ΔipaB | 100 | 600 | 0 |
| ΔipaB/pGST-IpaB | 100 | 5700 | 67 |
| M90T | 50 | | 64 |
|  | 25 | | 72 |
| ΔipaB/SipB | 50 | | 63 |
|  | 25 | | 57 |

These results indicate that the IpaB-GST fusion protein construct as well as the Salmonella sipB gene complemented the loss of invasiveness and cytotoxicity.

The references cited above are all incorporated by reference herein, whether specifically incorporated or not.

Having now fully described this invention, it will be appreciated by those skilled in the art that the same can be performed within a wide range of equivalent parameters, concentrations, and conditions without departing from the spirit and scope of the invention and without undue experimentation.

While this invention has been described in connection with specific embodiments thereof, it will be understood that it is capable of further modifications. This application is intended to cover any variations, uses, or adaptations of the invention following, in general, the principles of the invention and including such departures from the present disclosure as come within known or customary practice within the art to which the invention pertains and as may be applied to the essential features hereinbefore set forth as follows in the scope of the appended claims.

What is claimed is:

1. A method of inducing apoptosis in a mammalian cell, thereby killing the cell, comprising:

delivering in vitro or delivering site-specifically in vivo, to a cell to be killed, a DNA molecule which, under control of a promoter expresses Shigella IpaB protein, a homologue of said protein from a different bacterial genus or species, a fusion protein comprising said IpaB protein or IpaB homologue, a continuous peptide fragment of said protein or homologue, or a variant of said protein or homologue differing by a single conservative amino acid substitution, wherein said protein, homologue, fusion protein, peptide fragment or variant
   (i) induces apoptosis, and
   (ii) binds to interleukin-1-β converting enzyme or another caspase, and wherein,
   when said DNA molecule encodes said native IpaB or said homologue, it is free of DNA sequences encoding other proteins with which IpaB or said homologue are natively associated; and wherein said DNA molecule is expressed in said cell to produce said Ipab protein, homologue, fusion protein, peptide fragment or variant, thereby inducing apoptosis and killing said cell.

2. The method according to claim 1 wherein said DNA molecule encodes the IpaB protein.

3. The method according to claim 1 wherein said DNA comprises the nucleotide sequence of SEQ ID NO:1.

4. The method according to claim 1 wherein said homologue is from a genus of bacteria other than Shigella.

5. The method according to claim 4 wherein said homologue is *Salmonella typhimurium* sipB protein or *Salmonella typhi* sipB protein.

6. The method according to claim 1 wherein said DNA molecule encodes a fusion protein of IpaB or a fusion protein of an apoptosis-inducing fragment of IpaB.

7. The method according to claim 1 wherein, in step (a), said DNA is delivered to said cell in a live mammal.

8. The method according to claim 1 wherein said DNA molecule is a vector.

9. The method according to claim 8 wherein said DNA molecule is an expression plasmid encoding a fusion protein between IpaB and glutathione-S-transferase.

10. The method according to claim 8 wherein said vector is a viral vector.

11. The method according to claim 10 wherein said viral vector is a retroviral vector, an adenoviral vector, an adeno-associated viral vector, a herpes viral vector or a vaccinia viral vector.

12. The method according to claim 7 wherein said DNA is delivered by liposome-mediated DNA transfer or lipofection.

13. The method according to claim 1 wherein said cell is a tumor cell, a virus-infected cell or a cell undergoing unwanted proliferation.

14. A method for removing undesired cells from a mammal having undesired cells localized in a confined area or a focus, said method comprising inducing apoptosis in said undesired cells in accordance with claim 1, thereby removing said cells.

15. The method according to claim 14 wherein said localized undesired cells are cancer cells, benign hyperplastic cells, or cells associated with vascular restenosis or chronic focal infection.

16. The method according to claim 1, wherein said DNA encodes said peptide fragment.

17. The method according to claim 1, wherein said delivering step (a) is performed in vitro.

18. The method according to claim 17 wherein said cell is a macrophage, a tumor cell, an activated lymphocyte involved in an autoimmune response, a virus infected cell, or a cell undergoing unwanted proliferation.

19. The method of claim 1 wherein said promoter is an inducible promoter and said method further comprises inducing expression of said DNA molecule with an inducer of said inducible promoter.

20. The method according to claim 1 wherein said cell is a macrophage, a tumor cell, an activated lymphocyte involved in an autoimmune response, a virus infected cell, or a cell undergoing unwanted proliferation.

* * * * *

SEQUENCE LISTING (1) GENERAL INFORMATION:

(iii) NUMBER OF SEQUENCES: 10

(2) INFORMATION FOR SEQ ID NO:1:

(i) SEQUENCE CHARACTERISTICS:
(A) LENGTH: 1743 base pairs
(B) TYPE: nucleic acid
(C) STRANDEDNESS: single
(D) TOPOLOGY: linear (ix) FEATURE:
(A) NAME/KEY: CDS
(B) LOCATION: 1..1743

(ix) FEATURE:
(A) NAME/KEY: misc_feature
(B) LOCATION: 1..1743
(D) OTHER INFORMATION: /note= "Shigella flexneri ipaB"

(xi) SEQUENCE DESCRIPTION: SEQ ID NO:1:

```
ATG CAT AAT GTA AGC ACC ACA ACC ACT GGT TTT CCT CTT GCC AAA ATA         48
Met His Asn Val Ser Thr Thr Thr Thr Gly Phe Pro Leu Ala Lys Ile
 1               5                  10                  15

TTG ACT TCC ACT GAG CTT GGA GAC AAT ACT ATC CAA GCT GCA AAT GAT         96
Leu Thr Ser Thr Glu Leu Gly Asp Asn Thr Ile Gln Ala Ala Asn Asp
                20                  25                  30

GCA GCT AAC AAA TTA TTT TCT CTT ACA ATT GCT GAT CTT ACT GCT AAC        144
Ala Ala Asn Lys Leu Phe Ser Leu Thr Ile Ala Asp Leu Thr Ala Asn
             35                  40                  45

CAA AAT ATT AAT ACA ACT AAT GCA CAC TCA ACT TCA AAT ATA TTA ATC        192
Gln Asn Ile Asn Thr Thr Asn Ala His Ser Thr Ser Asn Ile Leu Ile
 50                  55                  60

CCT GAA CTT AAA GCA CCA AAG TCA TTA AAT GCA AGT TCC CAA CTA ACG        240
Pro Glu Leu Lys Ala Pro Lys Ser Leu Asn Ala Ser Ser Gln Leu Thr
 65                  70                  75                  80

CTT TTA ATT GGA AAC CTT ATT CAA ATA CTC GGT GAA AAA TCT TTA ACT        288
Leu Leu Ile Gly Asn Leu Ile Gln Ile Leu Gly Glu Lys Ser Leu Thr
                85                  90                  95

GCA TTA ACA AAT AAA ATT ACT GCT TGG AAG TCC CAG CAA CAG GCA AGA        336
Ala Leu Thr Asn Lys Ile Thr Ala Trp Lys Ser Gln Gln Gln Ala Arg
                100                 105                 110

CAG CAA AAA AAC CTA GAA TTC TCC GAT AAA ATT AAC ACT CTT CTA TCT        384
Gln Gln Lys Asn Leu Glu Phe Ser Asp Lys Ile Asn Thr Leu Leu Ser
            115                 120                 125

GAA ACT GAA GGA CTA ACC AGA GAC TAT GAA AAA CAA ATT AAT AAA CTA        432
Glu Thr Glu Gly Leu Thr Arg Asp Tyr Glu Lys Gln Ile Asn Lys Leu
130                 135                 140

AAA AAC GCA GAT TCT AAA ATA AAA GAC CTA GAA AAT AAA ATT AAC CAA        480
Lys Asn Ala Asp Ser Lys Ile Lys Asp Leu Glu Asn Lys Ile Asn Gln
145                 150                 155                 160

ATT CAA ACA AGA TTA TCG AAC CTC GAT CCA GAG TCA CCA GAA AAG AAA        528
Ile Gln Thr Arg Leu Ser Asn Leu Asp Pro Glu Ser Pro Glu Lys Lys
                165                 170                 175

AAA TTA AGC CGG GAA GAA ATA CAA CTC ACT ATC AAA AAA GAC GCA GCA        576
Lys Leu Ser Arg Glu Glu Ile Gln Leu Thr Ile Lys Lys Asp Ala Ala
            180                 185                 190

GTT AAA GAC AGG ACA TTG ATT GAG CAG AAA ACC CTG TCA ATT CAT AGC        624
Val Lys Asp Arg Thr Leu Ile Glu Gln Lys Thr Leu Ser Ile His Ser
        195                 200                 205

AAA CTT ACA GAT AAA TCA ATG CAA CTC GAA AAA GAA ATA GAC TCT TTT        672
```

-continued

| | | | | | | | | | | | | | | |
|---|---|---|---|---|---|---|---|---|---|---|---|---|---|---|
|Lys|Leu|Thr|Asp|Lys|Ser|Met|Gln|Leu|Glu|Lys|Glu|Ile|Asp|Ser|Phe|
| |210| | | |215| | | |220| | | | | | |

```
TCT GCA TTT TCA AAC ACA GCT GCT GAA CAG CTA TCA ACC CAG CAG        720
Ser Ala Phe Ser Asn Thr Ala Ser Ala Glu Gln Leu Ser Thr Gln Gln
225             230              235             240

AAA TCA TTA ACC GGA CTT GCC AGT GTT ACT CAA TTG ATG GCA ACC TTT    768
Lys Ser Leu Thr Gly Leu Ala Ser Val Thr Gln Leu Met Ala Thr Phe
            245              250             255

ATT CAA CTA GTT GGA AAA AAT AAT GAA GAA TCT TTA AAA AAT GAT CTG    816
Ile Gln Leu Val Gly Lys Asn Asn Glu Glu Ser Leu Lys Asn Asp Leu
            260              265             270

GCT CTA TTC CAG TCT CTC CAA GAA TCA AGA AAA ACT GAA ATG GAG AGA    864
Ala Leu Phe Gln Ser Leu Gln Glu Ser Arg Lys Thr Glu Met Glu Arg
            275              280             285

AAA TCT GAT GAG TAT GCT GCT GAA GTA CGT AAA GCA GAA GAA CTC AAC    912
Lys Ser Asp Glu Tyr Ala Ala Glu Val Arg Lys Ala Glu Glu Leu Asn
290             295              300

AGA GTA ATG GGT TGT GTT GGG AAA ATA CTT GGG GCA CTT TTA ACT ATC    960
Arg Val Met Gly Cys Val Gly Lys Ile Leu Gly Ala Leu Leu Thr Ile
305             310              315             320

GTT AGT GTT GTT GCA GCA GCT TTT TCT GGA GGA GCC TCT CTA GCA CTG   1008
Val Ser Val Val Ala Ala Ala Phe Ser Gly Gly Ala Ser Leu Ala Leu
                325              330             335

GCA GCT GTT GGT TTA GCT CTT ATG GTT ACG GAT GCT ATA GTA CAA GCA   1056
Ala Ala Val Gly Leu Ala Leu Met Val Thr Asp Ala Ile Val Gln Ala
            340              345             350

GCG ACC GGC AAT TCC TTC ATG GAA CAA GCC CTG AAT CCG ATC ATG AAA   1104
Ala Thr Gly Asn Ser Phe Met Glu Gln Ala Leu Asn Pro Ile Met Lys
            355              360             365

GCA GTC ATT GAA CCC TTA ATC AAA CTC CTT TCA GAT GCA TTT ACA AAA   1152
Ala Val Ile Glu Pro Leu Ile Lys Leu Leu Ser Asp Ala Phe Thr Lys
370             375              380

ATG CTC GAA GGC TTG GGC GTC GAC TCG AAA AAA GCC AAA ATG ATT GGC   1200
Met Leu Glu Gly Leu Gly Val Asp Ser Lys Lys Ala Lys Met Ile Gly
385             390              395             400

TCT ATT CTG GGG GCA ATC GCA GGC GCT CTT GTC CTA GTT GCA GCA GTC   1248
Ser Ile Leu Gly Ala Ile Ala Gly Ala Leu Val Leu Val Ala Ala Val
                405              410             415

GTT CTC GTA GCC ACT GTT GGT AAA CAG GCA GCA GCA AAA CTT GCA GAA   1296
Val Leu Val Ala Thr Val Gly Lys Gln Ala Ala Ala Lys Leu Ala Glu
            420              425             430

AAT ATT GGC AAA ATA ATA GGT AAA ACC CTC ACA GAC CTT ATA CCA AAG   1344
Asn Ile Gly Lys Ile Ile Gly Lys Thr Leu Thr Asp Leu Ile Pro Lys
            435              440             445

TTT CTC AAG AAT TTT TCT TCT CAA CTG GAC GAT TTA ATC ACT AAT GCT   1392
Phe Leu Lys Asn Phe Ser Ser Gln Leu Asp Asp Leu Ile Thr Asn Ala
            450              455             460

GTT GCC AGA TTA AAT AAA TTT CTT GGT GCA GCG GGT GAT GAA GTA ATA   1440
Val Ala Arg Leu Asn Lys Phe Leu Gly Ala Ala Gly Asp Glu Val Ile
465             470              475             480

TCC AAA CAA ATT ATT TCC ACC CAT TTA AAC CAA GCA GTT TTA TTA GGA   1488
Ser Lys Gln Ile Ile Ser Thr His Leu Asn Gln Ala Val Leu Leu Gly
            485              490             495

GAA AGT GTT AAC TCT GCC ACA CAA GCG GGA GGA AGT GTC GCT TCT GCT   1536
Glu Ser Val Asn Ser Ala Thr Gln Ala Gly Gly Ser Val Ala Ser Ala
            500              505             510

GTT TTC CAG AAC AGC GCG TCG ACA AAT CTA GCA GAC CTG ACA TTA TCG   1584
Val Phe Gln Asn Ser Ala Ser Thr Asn Leu Ala Asp Leu Thr Leu Ser
            515              520             525

AAA TAT CAA GTT GAA CAA CTG TCA AAA TAT ATC AGT GAA GCA ATA GAA   1632
```

```
Lys Tyr Gln Val Glu Gln Leu Ser Lys Tyr Ile Ser Glu Ala Ile Glu
    530                 535                 540

AAA TTC GGC CAA TTG CAG GAA GTA ATT GCA GAT CTA TTA GCC TCA ATG    1680
Lys Phe Gly Gln Leu Gln Glu Val Ile Ala Asp Leu Leu Ala Ser Met
545                 550                 555                 560

TCC AAC TCT CAG GCT AAT AGA ACT GAT GTT GCA AAA GCA ATT TTG CAA    1728
Ser Asn Ser Gln Ala Asn Arg Thr Asp Val Ala Lys Ala Ile Leu Gln
                565                 570                 575

CAA ACT ACT GCT TGA                                                 1743
Gln Thr Thr Ala  *
            580
```

(2) INFORMATION FOR SEQ ID NO:2:

(i) SEQUENCE CHARACTERISTICS:
        (A) LENGTH: 580 amino acids
        (B) TYPE: amino acid
        (D) TOPOLOGY: linear (ii) MOLECULE TYPE: protein (xi) SEQUENCE DESCRIPTION: SEQ ID NO:2:

```
Met His Asn Val Ser Thr Thr Thr Gly Phe Pro Leu Ala Lys Ile
1               5                   10                  15

Leu Thr Ser Thr Glu Leu Gly Asp Asn Thr Ile Gln Ala Ala Asn Asp
                20                  25                  30

Ala Ala Asn Lys Leu Phe Ser Leu Thr Ile Ala Asp Leu Thr Ala Asn
            35                  40                  45

Gln Asn Ile Asn Thr Thr Asn Ala His Ser Thr Ser Asn Ile Leu Ile
50                  55                  60

Pro Glu Leu Lys Ala Pro Lys Ser Leu Asn Ala Ser Ser Gln Leu Thr
65                  70                  75                  80

Leu Leu Ile Gly Asn Leu Ile Gln Ile Leu Gly Glu Lys Ser Leu Thr
                85                  90                  95

Ala Leu Thr Asn Lys Ile Thr Ala Trp Lys Ser Gln Gln Gln Ala Arg
            100                 105                 110

Gln Gln Lys Asn Leu Glu Phe Ser Asp Lys Ile Asn Thr Leu Leu Ser
        115                 120                 125

Glu Thr Glu Gly Leu Thr Arg Asp Tyr Glu Lys Gln Ile Asn Lys Leu
130                 135                 140

Lys Asn Ala Asp Ser Lys Ile Lys Asp Leu Glu Asn Lys Ile Asn Gln
145                 150                 155                 160

Ile Gln Thr Arg Leu Ser Asn Leu Asp Pro Glu Ser Pro Glu Lys Lys
                165                 170                 175

Lys Leu Ser Arg Glu Glu Ile Gln Leu Thr Ile Lys Lys Asp Ala Ala
            180                 185                 190

Val Lys Asp Arg Thr Leu Ile Glu Gln Lys Thr Leu Ser Ile His Ser
195                 200                 205

Lys Leu Thr Asp Lys Ser Met Gln Leu Glu Lys Glu Ile Asp Ser Phe
210                 215                 220

Ser Ala Phe Ser Asn Thr Ala Ser Ala Glu Gln Leu Ser Thr Gln Gln
225                 230                 235                 240

Lys Ser Leu Thr Gly Leu Ala Ser Val Thr Gln Leu Met Ala Thr Phe
                245                 250                 255

Ile Gln Leu Val Gly Lys Asn Asn Glu Glu Ser Leu Lys Asn Asp Leu
            260                 265                 270

Ala Leu Phe Gln Ser Leu Gln Glu Ser Arg Lys Thr Glu Met Glu Arg
        275                 280                 285
```

```
Lys Ser Asp Glu Tyr Ala Ala Glu Val Arg Lys Ala Glu Glu Leu Asn
    290                 295                 300

Arg Val Met Gly Cys Val Gly Lys Ile Leu Gly Ala Leu Leu Thr Ile
305                 310                 315                 320

Val Ser Val Val Ala Ala Ala Phe Ser Gly Gly Ala Ser Leu Ala Leu
                325                 330                 335

Ala Ala Val Gly Leu Ala Leu Met Val Thr Asp Ala Ile Val Gln Ala
            340                 345                 350

Ala Thr Gly Asn Ser Phe Met Glu Gln Ala Leu Asn Pro Ile Met Lys
        355                 360                 365

Ala Val Ile Glu Pro Leu Ile Lys Leu Leu Ser Asp Ala Phe Thr Lys
    370                 375                 380

Met Leu Glu Gly Leu Gly Val Asp Ser Lys Lys Ala Lys Met Ile Gly
385                 390                 395                 400

Ser Ile Leu Gly Ala Ile Ala Gly Ala Leu Val Leu Val Ala Ala Val
                405                 410                 415

Val Leu Val Ala Thr Val Gly Lys Gln Ala Ala Ala Lys Leu Ala Glu
            420                 425                 430

Asn Ile Gly Lys Ile Ile Gly Lys Thr Leu Thr Asp Leu Ile Pro Lys
        435                 440                 445

Phe Leu Lys Asn Phe Ser Ser Gln Leu Asp Asp Leu Ile Thr Asn Ala
    450                 455                 460

Val Ala Arg Leu Asn Lys Phe Leu Gly Ala Ala Gly Asp Glu Val Ile
465                 470                 475                 480

Ser Lys Gln Ile Ile Ser Thr His Leu Asn Gln Ala Val Leu Leu Gly
                485                 490                 495

Glu Ser Val Asn Ser Ala Thr Gln Ala Gly Gly Ser Val Ala Ser Ala
            500                 505                 510

Val Phe Gln Asn Ser Ala Ser Thr Asn Leu Ala Asp Leu Thr Leu Ser
        515                 520                 525

Lys Tyr Gln Val Glu Gln Leu Ser Lys Tyr Ile Ser Glu Ala Ile Glu
    530                 535                 540

Lys Phe Gly Gln Leu Gln Glu Val Ile Ala Asp Leu Leu Ala Ser Met
545                 550                 555                 560

Ser Asn Ser Gln Ala Asn Arg Thr Asp Val Ala Lys Ala Ile Leu Gln
                565                 570                 575

Gln Thr Thr Ala
            580

(2) INFORMATION FOR SEQ ID NO:3:

(i) SEQUENCE CHARACTERISTICS:
(A) LENGTH: 2512 base pairs
(B) TYPE: nucleic acid
(C) STRANDEDNESS: single
(D) TOPOLOGY: linear (ii) MOLECULE TYPE: DNA (genomic)

(vi) ORIGINAL SOURCE:
(A) ORGANISM: Yersinia enterocolitica
(B) STRAIN: W22703(pYVe227)

(ix) FEATURE:
(A) NAME/KEY: CDS
(B) LOCATION: 12..1217

(xi) SEQUENCE DESCRIPTION: SEQ ID NO:3:

```
GGAGATGAAA C ATG AGT GCG TTG ATA ACC CAT GAT CGC TCA ACG CCA GTA      50
```

```
                Met Ser Ala Leu Ile Thr His Asp Arg Ser Thr Pro Val
                                585                 590
ACT GGA AGT CTA GTT CCC TAC ATC GAG ACA CCA GCG CCC GCC CCC CTT         98
Thr Gly Ser Leu Val Pro Tyr Ile Glu Thr Pro Ala Pro Ala Pro Leu
595                 600                 605                 610

CAG ACC CAA CAA GTC GCG GGA GAA CTG AAG GAT AAA AAT GGC GGG GTG         146
Gln Thr Gln Gln Val Ala Gly Glu Leu Lys Asp Lys Asn Gly Gly Val
                615                 620                 625

AGT TCT CAG GGC GTG CAG CTC CCT GCA CCA CTA GCA GTG GTT GCC AGC         194
Ser Ser Gln Gly Val Gln Leu Pro Ala Pro Leu Ala Val Val Ala Ser
            630                 635                 640

CAA GTC ACT GAA GGA CAA CAG CAA GAA ATC ACT AAA TTA TTG GAG TCG         242
Gln Val Thr Glu Gly Gln Gln Gln Glu Ile Thr Lys Leu Leu Glu Ser
        645                 650                 655

GTC ACC CGC GGC ACG GCA GGA TCT CAA CTG ATA TCA AAT TAT GTT TCA         290
Val Thr Arg Gly Thr Ala Gly Ser Gln Leu Ile Ser Asn Tyr Val Ser
    660                 665                 670

GTG CTA ACG AAT TTT ACG CTC GCT TCA CCT GAT ACA TTT GAG ATT GAG         338
Val Leu Thr Asn Phe Thr Leu Ala Ser Pro Asp Thr Phe Glu Ile Glu
675                 680                 685                 690

TTA GGT AAG CTA GTT TCT AAT TTA GAA GAA GTA CGC AAA GAC ATA AAA         386
Leu Gly Lys Leu Val Ser Asn Leu Glu Glu Val Arg Lys Asp Ile Lys
                695                 700                 705

ATC GCT GAT ATT CAG CGT CTT CAT GAA CAA AAC ATG AAG AAA ATT GAA         434
Ile Ala Asp Ile Gln Arg Leu His Glu Gln Asn Met Lys Lys Ile Glu
            710                 715                 720

GAG AAT CAA GAG AAA ATC AAA GAA ACA GAA GAG AAT GCC AAG CAA GTC         482
Glu Asn Gln Glu Lys Ile Lys Glu Thr Glu Glu Asn Ala Lys Gln Val
        725                 730                 735

AAG AAA TCC GGC ATG GCA TCA AAG ATT TTT GGC TGG CTC ATC GCC ATA         530
Lys Lys Ser Gly Met Ala Ser Lys Ile Phe Gly Trp Leu Ile Ala Ile
    740                 745                 750

GCC TCA GTG GTT ATC GGT GCC ATC ATG GTG GCC TCA GGG GTA GGA GCC         578
Ala Ser Val Val Ile Gly Ala Ile Met Val Ala Ser Gly Val Gly Ala
755                 760                 765                 770

GTT GCC GGT GCA ATG ATG ATT GCC TCA GGC GTA ATT GGG ATG GCG AAT         626
Val Ala Gly Ala Met Met Ile Ala Ser Gly Val Ile Gly Met Ala Asn
                775                 780                 785

ATG GCT GTG AAA CAA GCG GCG GAA GAT GGC CTG ATA TCC CAA GAG GCA         674
Met Ala Val Lys Gln Ala Ala Glu Asp Gly Leu Ile Ser Gln Glu Ala
            790                 795                 800

ATG CAA GTA TTA GGG CCG ATA CTC ACT GCG ATT GAA GTC GCA TTG ACT         722
Met Gln Val Leu Gly Pro Ile Leu Thr Ala Ile Glu Val Ala Leu Thr
        805                 810                 815

GTA GTT TCA ACC GTA ATG ACC TTT GGC GGT TCG GCA CTA AAA TGC CTG         770
Val Val Ser Thr Val Met Thr Phe Gly Gly Ser Ala Leu Lys Cys Leu
    820                 825                 830

GCT GAT ATT GGC GCA AAA CTC GGT GCT AAC ACC GCA AGT CTT GCT GCT         818
Ala Asp Ile Gly Ala Lys Leu Gly Ala Asn Thr Ala Ser Leu Ala Ala
835                 840                 845                 850

AAA GGA GCC GAG TTT TCA GCC AAA GTT GCC CAA ATT TCG ACA GGC ATA         866
Lys Gly Ala Glu Phe Ser Ala Lys Val Ala Gln Ile Ser Thr Gly Ile
                855                 860                 865

TCA AAC ACT GTC GGG AGT GCG GTG ACT AAA TTA GGG GGC AGT TTT GGT         914
Ser Asn Thr Val Gly Ser Ala Val Thr Lys Leu Gly Gly Ser Phe Gly
            870                 875                 880

AGT TTA ACA ATG AGC CAT GTA ATC CGT ACA GGA TCA CAG GCA ACA CAA         962
Ser Leu Thr Met Ser His Val Ile Arg Thr Gly Ser Gln Ala Thr Gln
        885                 890                 895

GTC GCC GTT GGT GTG GGC AGC GGA ATA ACT CAG ACC ATC AAT AAT AAA         1010
```

-continued

```
Val Ala Val Gly Val Gly Ser Gly Ile Thr Gln Thr Ile Asn Asn Lys
    900                 905                 910

AAG CAA GCT GAT TTA CAA CAT AAT AAC GCT GAT TTG GCC TTG AAC AAG      1058
Lys Gln Ala Asp Leu Gln His Asn Asn Ala Asp Leu Ala Leu Asn Lys
915                 920                 925                 930

GCA GAC ATG GCA GCG TTA CAA AGT ATT ATT GAC CGA CTC AAA GAA GAG      1106
Ala Asp Met Ala Ala Leu Gln Ser Ile Ile Asp Arg Leu Lys Glu Glu
                935                 940                 945

TTA TCC CAT TTG TCA GAG TCA CAT CGA CAA GTG ATG GAA CTG ATT TTC      1154
Leu Ser His Leu Ser Glu Ser His Arg Gln Val Met Glu Leu Ile Phe
            950                 955                 960

CAG ATG ATT AAT GCA AAA GGT GAC ATG CTG CAT AAT TTG GCC GGC AGA      1202
Gln Met Ile Asn Ala Lys Gly Asp Met Leu His Asn Leu Ala Gly Arg
        965                 970                 975

CCC CAT ACT GTT TAA GTTTAAGGAG GAATAACAAT GACAATAAAT ATCAAGACAG      1257
Pro His Thr Val *
    980

ACAGCCCAAT TATCACGACC GGTTCACAGC TTGATGCCAT CACTACAGAG ACAGTCGGGC    1317

AAAGCGGTGA GGTTAAAAAA ACAGAAGACA CCCGTCATGA AGCACAAGCA ATAAAGAGTA    1377

GCGAGGCAAG CTTATCTCGG TCACAGGTGC CTGAATTGAT CAAACCGAGT CAGGGAATCA    1437

ATGTTGCATT ACTGAGTAAA AGCCAGGGAG ATCTTAATGG TACTTTAAGT ATCTTGTTGT    1497

TGCTGTTGGA ACTGGCACGT AAAGCGCGAG AAATGGGTTT GCAACAAAGG GATATAGAAA    1557

ATAAAGCTAC TATTTCTGCC CAAAAGGAGC AGGTAGCGGA GATGGTCAGC GGTGCAAAAC    1617

TGATGATCGC CATGGCGGTG GTGTCTGGCA TCATGGCTGC TACTTCTACG GTTGCTAGTG    1677

CTTTTTCTAT AGCGAAAGAG GTGAAAATAG TTAAACAGGA ACAAATTCTA AACAGTAACA    1737

TTGCCGGCCG TGATCAACTT ATTGATACAA AAATGCAGCA AATGAGTAAC GCTGGTGATA    1797

AAGCGGTAAG CAGAGAGGAT ATCGGGAGAA TATGGAAACC AGAGCAGGTA GCGGATCAAA    1857

ATAAGCTGGC ATTATTGGAT AAAGAATTCA GAATGACCGA CTCAAAAGCC AATGCGTTTA    1917

ATGCCGCAAC GCAGCCGTTA GGACAAATGG CAAACAGTGC GATTCAAGTT CATCAAGGGT    1977

ATTCTCAAGC CGAGGTCAAA GAAAAAGAAG TCAATGCAAG TATTGCTGCC AACGAGAAGC    2037

AAAAAGCCGA AGAGGCGATG AACTATAATG ATAACTTTAT GAAAGATGTC CTGCGCTTGA    2097

TTGAACAATA TGTTAGCAGT CATACTCACG CCATGAAAGC CGCTTTTGGT GTTGTCTGAC    2157

CATTTATGAC CTTGGTTAGT TAATTAACCG AAAGTTTTAT TTTACCTTAC GCCTTATGGT    2217

GATAGAACTT ATCTATATAA GGTAAAGGTG CTGAAAAGCC CTGGATTAAT ATTAGTTAAT    2277

CCAGGGCTTT GATTATTAAC TTAAAAATAA TAAGTTATGA TCATATGACA ATTAAAATAA    2337

AAGATTATTT ACATGTAGTA GCTCAAGACC TGAGCTGACA GTTATCTTAA TGCCATTAAT    2397

CAAACAGTTA ACCAAAGTCA CACTGACTGC CGAACTCGAC TCATACCTGG CTCTGGACAT    2457

CGAAGCCAAT CGCAAAAATG GTTCGTCCAG AAAAACGGTC AAAACTCCCA CTGGT         2512
```

(2) INFORMATION FOR SEQ ID NO:4:

(i) SEQUENCE CHARACTERISTICS:
       (A) LENGTH: 401 amino acids
       (B) TYPE: amino acid
       (D) TOPOLOGY: linear (ii) MOLECULE TYPE: protein (xi) SEQUENCE DESCRIPTION: SEQ ID NO:4:

```
Met Ser Ala Leu Ile Thr His Asp Arg Ser Thr Pro Val Thr Gly Ser
1               5                   10                  15
```

```
Leu Val Pro Tyr Ile Glu Thr Pro Ala Pro Ala Pro Leu Gln Thr Gln
            20                  25                  30

Gln Val Ala Gly Glu Leu Lys Asp Lys Asn Gly Gly Val Ser Ser Gln
            35                  40                  45

Gly Val Gln Leu Pro Ala Pro Leu Ala Val Val Ala Ser Gln Val Thr
            50                  55                  60

Glu Gly Gln Gln Gln Glu Ile Thr Lys Leu Leu Glu Ser Val Thr Arg
 65                  70                  75                  80

Gly Thr Ala Gly Ser Gln Leu Ile Ser Asn Tyr Val Ser Val Leu Thr
            85                  90                  95

Asn Phe Thr Leu Ala Ser Pro Asp Thr Phe Glu Ile Glu Leu Gly Lys
            100                 105                 110

Leu Val Ser Asn Leu Glu Glu Val Arg Lys Asp Ile Lys Ile Ala Asp
            115                 120                 125

Ile Gln Arg Leu His Glu Gln Asn Met Lys Lys Ile Glu Glu Asn Gln
            130                 135                 140

Glu Lys Ile Lys Glu Thr Glu Asn Ala Lys Gln Val Lys Lys Ser
145                 150                 155                 160

Gly Met Ala Ser Lys Ile Phe Gly Trp Leu Ile Ala Ile Ala Ser Val
                    165                 170                 175

Val Ile Gly Ala Ile Met Val Ala Ser Gly Val Gly Ala Val Ala Gly
            180                 185                 190

Ala Met Met Ile Ala Ser Gly Val Ile Gly Met Ala Asn Met Ala Val
            195                 200                 205

Lys Gln Ala Ala Glu Asp Gly Leu Ile Ser Gln Glu Ala Met Gln Val
            210                 215                 220

Leu Gly Pro Ile Leu Thr Ala Ile Glu Val Ala Leu Thr Val Val Ser
225                 230                 235                 240

Thr Val Met Thr Phe Gly Gly Ser Ala Leu Lys Cys Leu Ala Asp Ile
                    245                 250                 255

Gly Ala Lys Leu Gly Ala Asn Thr Ala Ser Leu Ala Ala Lys Gly Ala
            260                 265                 270

Glu Phe Ser Ala Lys Val Ala Gln Ile Ser Thr Gly Ile Ser Asn Thr
            275                 280                 285

Val Gly Ser Ala Val Thr Lys Leu Gly Gly Ser Phe Gly Ser Leu Thr
            290                 295                 300

Met Ser His Val Ile Arg Thr Gly Ser Gln Ala Thr Gln Val Ala Val
305                 310                 315                 320

Gly Val Gly Ser Gly Ile Thr Gln Thr Ile Asn Asn Lys Lys Gln Ala
                    325                 330                 335

Asp Leu Gln His Asn Asn Ala Asp Leu Ala Leu Asn Lys Ala Asp Met
            340                 345                 350

Ala Ala Leu Gln Ser Ile Ile Asp Arg Leu Lys Glu Glu Leu Ser His
            355                 360                 365

Leu Ser Glu Ser His Arg Gln Val Met Glu Leu Ile Phe Gln Met Ile
            370                 375                 380

Asn Ala Lys Gly Asp Met Leu His Asn Leu Ala Gly Arg Pro His Thr
385                 390                 395                 400

Val (2) INFORMATION FOR SEQ ID NO:5:

(i) SEQUENCE CHARACTERISTICS:
        (A) LENGTH: 3106 base pairs
        (B) TYPE: nucleic acid
```

```
        (C) STRANDEDNESS: single
        (D) TOPOLOGY: linear (ii) MOLECULE TYPE: DNA (genomic)

(vi) ORIGINAL SOURCE:
         (A) ORGANISM: Yersinia pseudotuberculosis
         (B) STRAIN: YPIII(pIB1)

(ix) FEATURE:
         (A) NAME/

```
GCT AAT ATT GGC GCA AAA CTC GGT GCT AAC ACC GCA AGT CTT GCG GCT     818
Ala Asn Ile Gly Ala Lys Leu Gly Ala Asn Thr Ala Ser Leu Ala Ala
            660                 665                 670

AAA GGA GCC GAG TTT TCG GCC AAA GTT GCC CAA ATT TCG ACA GGC ATA     866
Lys Gly Ala Glu Phe Ser Ala Lys Val Ala Gln Ile Ser Thr Gly Ile
            675                 680                 685

TCA AAC ACT GTC GGG AGT GCA GTG ACT AAA TTA GGG GGC AGT TTT GCT     914
Ser Asn Thr Val Gly Ser Ala Val Thr Lys Leu Gly Gly Ser Phe Ala
            690                 695                 700

GGT TTA ACA ATG AGC CAT GCA ATC CGT ACA GGA TCA CAG GCA ACA CAA     962
Gly Leu Thr Met Ser His Ala Ile Arg Thr Gly Ser Gln Ala Thr Gln
    705                 710                 715

GTC GCC GTT GGT GTG GGC AGC GGA ATA ACT CAG ACC ATC AAT AAT AAA    1010
Val Ala Val Gly Val Gly Ser Gly Ile Thr Gln Thr Ile Asn Asn Lys
720                 725                 730                 735

AAG CAA GCT GAT TTA CAA CAT AAT AAC GCT GAT TTG GCC TTG AAC AAG    1058
Lys Gln Ala Asp Leu Gln His Asn Asn Ala Asp Leu Ala Leu Asn Lys
                740                 745                 750

GCA GAC ATG GCA GCG TTA CAA AGT ATT ATT GAC CGA CTC AAA GAA GAG    1106
Ala Asp Met Ala Ala Leu Gln Ser Ile Ile Asp Arg Leu Lys Glu Glu
                755                 760                 765

TTA TCC CAT TTG TCA GAG TCA CAT CAA CAA GTG ATG GAA CTG ATT TTC    1154
Leu Ser His Leu Ser Glu Ser His Gln Gln Val Met Glu Leu Ile Phe
            770                 775                 780

CAG ATG ATT AAT GCA AAA GGT GAC ATG CTG CAT AAT TTG GCC GGC AGA    1202
Gln Met Ile Asn Ala Lys Gly Asp Met Leu His Asn Leu Ala Gly Arg
            785                 790                 795

CCC CAT ACT GTT TAA GTTTAAGGAG GAATAACCAT GACAATAAAT ATCAAGACAG    1257
Pro His Thr Val *
800

ACAGCCCAAT TATCACGACC GGTTCACAGC TTGATGCCAT CACTACAGAG ACAGTCAAGC  1317

AAAGCGGTGA GATTAAAAAA ACAGAAGACA CCCGTCATGA AGCACAAGCA ATAAAGAGTA  1377

GCGAGGCAAG CTTATCTCGG TCACAGGTGC CAGAATTGAT CAAACCGAGC CAGGGAATCA  1437

ATGTTGCATT ACTGAGTAAA AGCCAGGGTG ATCTTAATGG TACTTTAAGT ATCTTGTTGT  1497

TGCTGTTGGA ACTGGCACGT AAAGCGCGAG AAATGGGTTT GCAACAAAGG GATATAGAAA  1557

ATAAAGCTAC TATTACTGCC CAAAAGGAGC AGGTAGCGGA GATGGTCAGC GGTGCAAAAC  1617

TGATGATCGC CATGGCGGTG GTGTCTGGCA TCATGGCTGC TACTTCTACG GTTGCTAGTG  1677

CTTTTTCTAT AGCGAAAGAG GTGAAAATAG TTAAACAGGA ACAAATTCTA AACAGTAATA  1737

TTGCTGGCCG CGAACAACTT ATTGATACAA AAATGCAGCA AATGGGTAAC ATTGGTGATA  1797

AAGCGGTAAG CAGAGAGGAT ATCGGGAGAA TATGGAAACC AGAGCAGGTA GCGGATCAAA  1857

ATAAGCTGGC ATTATTGGAT AAAGAATTCA GAATGACCGA CTCAAAAGCC AATGCGTTTA  1917

ATGCCGCAAC GCAGCCGTTA GGACAAATGG CAAACAGTGC GATTCAAGTT CATCAAGGGT  1977

ATTCTCAAGC CGAGGTCAAA GAGAAAGAAG TCAATGCAAG TATTGCTGCC AACGAGAAGC  2037

AAAAAGCCGA AGAGGCGATG AACTATAATG ATAACTTTAT GAAAGATGTC CTGCGCTTGA  2097

TTGAACAATA TGTTAGCAGT CATACTCACG CCATGAAAGC CGCTTTTGGT GTTGTCTGAC  2157

CATTGATGAC CTTGGTTAGT TAATTAACCG AAAGTTTTAT TTTACCTTAC CCCTTATGGT  2217

GATAGAACTT ATCTATATAA GGTATAAGGT GCTGAAAAGC CCTGGATTAA TATTAGTTAA  2277

TCCAGGGTTG TGATTATTAA ATTAAAAATA ATAAGTTAGG ATCATATGAC AATTAAAATA  2337

AAAGATTATT TACATGTAGT AGCTCAAGAC CTGAGCTGAC AGTTACCGGT TGTTGAACGG  2397

CAATACGCGG TCATTGAGCA CGTCAGCGGC TGTGATCGGC ATTTTGCTCG TATACAGCGA  2457
```

```
GAGTGTTAGA AATGCTGTGC TATTCCAGTA ATATGCAATC AAAAAAGAAT GACACATATC    2517

CCAATAATGA GAGTCGGTGA TTTTACTCAT TGATGGGGGG GAATAATTAG GCTAAAACAA    2577

CCTCAATGTT AAAGAGCCGA CTCATAAAGG TAGATCCTTC CCGCACTCAA TATTCAGGTT    2637

CGTCACGGCG TAACCAAATA TAAAATTGAC CTTTATTCAG TCGTTGCAAT GTTTCAAATC    2697

CCTGAAGCGT TGACCAGGCA CGGTTTGGCC GTTTGAAATC CCCGGCCGCG TTTACCAATT    2757

TTTTGATGGG GGCATGGTCA GACTCGATAC GATTATTCAG GTATTTGACT TGCCGCTGCT    2817

TTGCAGCATC CCGTATCTTT TCCTTCTTTC ATCAAACGAG TGATAGCGTA ACCGTATGAC    2877

GAATGTTTAT CGGTATTGAG TATTTTAGGC TGTCTTTCAA CAGAATAGGG TTTTAACACC    2937

CGTTTAATGA ATGGATAGGC GGTATTTTTA TTTCGTTTAG GCGAAAAATA AAAATCTAAT    2997

GTAGTGCCGT GCTTATTGAT GGCGCGATAG AGATAAAACC ATTTTCCGTT GACCCTGATA    3057

TAGATTTCAT CGAGTTGCCA TGAGGAGTCG GCATCCGTAA ATTGATATC              3106
```

(2) INFORMATION FOR SEQ ID NO:6:

(i) SEQUENCE CHARACTERISTICS:
        (A) LENGTH: 401 amino acids
        (B) TYPE: amino acid
        (D) TOPOLOGY: linear (ii) MOLECULE TYPE: protein (xi) SEQUENCE DESCRIPTION: SEQ ID NO:6:

```
Met Ser Ala Leu Ile Thr His Asp Arg Ser Thr Pro Val Thr Gly Ser
 1               5                  10                  15

Leu Leu Pro Tyr Val Glu Thr Pro Ala Pro Ala Pro Leu Gln Thr Gln
             20                  25                  30

Gln Val Ala Gly Glu Leu Lys Asp Lys Asn Gly Gly Val Ser Ser Gln
         35                  40                  45

Gly Val Gln Leu Pro Ala Pro Leu Ala Val Val Ala Ser Gln Val Thr
     50                  55                  60

Glu Gly Gln Gln Gln Glu Val Thr Lys Leu Leu Glu Ser Val Thr Arg
 65                  70                  75                  80

Gly Ala Ala Gly Ser Gln Leu Ile Ser Asn Tyr Val Ser Val Leu Thr
                 85                  90                  95

Lys Phe Thr Leu Ala Ser Pro Asp Thr Phe Glu Ile Glu Leu Gly Lys
            100                 105                 110

Leu Val Ser Asn Leu Glu Glu Val Arg Lys Asp Ile Lys Ile Ala Asp
        115                 120                 125

Ile Gln Arg Leu His Glu Gln Asn Met Lys Lys Ile Glu Glu Asn Gln
    130                 135                 140

Glu Lys Ile Lys Glu Thr Glu Glu Asn Ala Lys Gln Val Lys Lys Ser
145                 150                 155                 160

Gly Ile Ala Ser Lys Ile Phe Gly Trp Leu Ser Ala Ile Ala Ser Val
                165                 170                 175

Ile Val Gly Ala Ile Met Val Ala Ser Gly Val Gly Met Ala Val Ala Gly
            180                 185                 190

Ala Met Met Val Ala Ser Gly Val Ile Gly Met Ala Asn Met Ala Val
        195                 200                 205

Lys Gln Ala Ala Glu Asp Gly Leu Ile Ser Gln Glu Ala Met Lys Ile
    210                 215                 220

Leu Gly Pro Ile Leu Thr Ala Ile Glu Val Ala Leu Thr Val Val Ser
225                 230                 235                 240

Thr Val Met Thr Phe Gly Gly Ser Ala Leu Lys Cys Leu Ala Asn Ile
```

|                 | 245             |                 | 250             |                 | 255             |                 |
|---|---|---|---|---|---|---|

Gly Ala Lys Leu Gly Ala Asn Thr Ala Ser Leu Ala Ala Lys Gly Ala
              260                 265                 270

Glu Phe Ser Ala Lys Val Ala Gln Ile Ser Thr Gly Ile Ser Asn Thr
              275                 280                 285

Val Gly Ser Ala Val Thr Lys Leu Gly Gly Ser Phe Ala Gly Leu Thr
              290                 295                 300

Met Ser His Ala Ile Arg Thr Gly Ser Gln Ala Thr Gln Val Ala Val
305                 310                 315                 320

Gly Val Gly Ser Gly Ile Thr Gln Thr Ile Asn Asn Lys Lys Gln Ala
              325                 330                 335

Asp Leu Gln His Asn Asn Ala Asp Leu Ala Leu Asn Lys Ala Asp Met
              340                 345                 350

Ala Ala Leu Gln Ser Ile Ile Asp Arg Leu Lys Glu Glu Leu Ser His
              355                 360                 365

Leu Ser Glu Ser His Gln Gln Val Met Glu Leu Ile Phe Gln Met Ile
              370                 375                 380

Asn Ala Lys Gly Asp Met Leu His Asn Leu Ala Gly Arg Pro His Thr
385                 390                 395                 400

Val (2) INFORMATION FOR SEQ ID NO:7:

(i) SEQUENCE CHARACTERISTICS:
        (A) LENGTH: 3622 base pairs
        (B) TYPE: nucleic acid
        (C) STRANDEDNESS: single
        (D) TOPOLOGY: linear (vi) ORIGINAL SOURCE:
        (A) ORGANISM: Salmonella typhimurium
        (B) STRAIN: sibB (ix) FEATURE:
        (A) NAME/KEY: CDS
        (B) LOCATION: 575..2356
        (D) OTHER INFORMATION: /product= "SipB"
            /gene= "sipB"

(xi) SEQUENCE DESCRIPTION: SEQ ID NO:7:

```
GGGTTTAATA ACTGCATCAG ATAAACGCAG TCGTTAAGTT CTACAAAGTC GGTGACAGAT      60

AACAGGAGTA AGTAATGGAT TATCAAAATA ATGTCAGCGA AGAACGTGTT GCGGAAATGA     120

TTTGGGATGC CGTTAGTGAA GGCGCCACGC TAAAAGACGT TCATGGGATC CCTCAAGATA     180

TGATGGACGG TTTATATGCT CATGCTTATG AGTTTTATAA CCAGGGACGA CTGGATGAAG     240

CTGAGACGTT CTTTCGTTTC TTATGCATTT ATGATTTTTA CAATCCCGAT TACACCATGG     300

GACTGGCGGC AGTATGCCAA CTGAAAAAAC AATTTCAGAA AGCATGTGAC CTTTATGCAG     360

TAGCGTTTAC GTTACTTAAA AATGATTATC GCCCCGTTTT TTTTACCGGG CAGTGTCAAT     420

TATTAATGCG TAAGGCAGCA AAAGCCGACA GTGTTTTGA ACTTGTCAAT GAACGTACTG      480

AAGATGAGTC TCTGCGGGCA AAAGCGTTGG TCTATCTGGA GGCGCTAAAA ACGGCGGAGA     540

CAGAGCAGCA CAGTGAACAA GAAAAGGAAT AATT ATG GTA AAT GAC GCA AGT        592
                                     Met Val Asn Asp Ala Ser
                                                         405

AGC ATT AGC CGT AGC GGA TAT ACC CAA AAT CCG CGC CTC GCT GAG GCG      640
Ser Ile Ser Arg Ser Gly Tyr Thr Gln Asn Pro Arg Leu Ala Glu Ala
        410                 415                 420

GCT TTT GAA GGC GTT CGT AAG AAC ACG GAC TTT TTA AAA GCG GCG GAT      688
Ala Phe Glu Gly Val Arg Lys Asn Thr Asp Phe Leu Lys Ala Ala Asp
```

-continued

```
     425             430             435             440

AAA GCT TTT AAA GAT GTG GTG GCA ACG AAA GCG GGC GAC CTT AAA GCC     736
Lys Ala Phe Lys Asp Val Val Ala Thr Lys Ala Gly Asp Leu Lys Ala
            445             450             455

GGA ACA AAG TCC GGC GAG AGC GCT ATT AAT ACG GTG GGT CTA AAG CCG     784
Gly Thr Lys Ser Gly Glu Ser Ala Ile Asn Thr Val Gly Leu Lys Pro
        460             465             470

CCT ACG GAC GCC GCC CGG GAA AAA CTC TCC AGC GAA GGG CAA TTG ACA     832
Pro Thr Asp Ala Ala Arg Glu Lys Leu Ser Ser Glu Gly Gln Leu Thr
        475             480             485

TTA CTG CTT GGC AAG TTA ATG ACC CTA CTG GGC GAT GTT TCG CTG TCT     880
Leu Leu Leu Gly Lys Leu Met Thr Leu Leu Gly Asp Val Ser Leu Ser
        490             495             500

CAA CTG GAG TCT CGT CTG GCG GTA TGG CAG GCG ATG ATT GAG TCA CAA     928
Gln Leu Glu Ser Arg Leu Ala Val Trp Gln Ala Met Ile Glu Ser Gln
505             510             515             520

AAA GAG ATG GGG ATT CAG GTA TCG AAA GAA TTC CAG ACG GCT CTG GGA     976
Lys Glu Met Gly Ile Gln Val Ser Lys Glu Phe Gln Thr Ala Leu Gly
            525             530             535

GAG GCT CAG GAG GCG ACG GAT CTC TAT GAA GCC AGT ATC AAA AAG ACG    1024
Glu Ala Gln Glu Ala Thr Asp Leu Tyr Glu Ala Ser Ile Lys Lys Thr
        540             545             550

GAT ACC GCC AAG AGT GTT TAT GAC GCT GCG ACC AAA AAA CTG ACG CAG    1072
Asp Thr Ala Lys Ser Val Tyr Asp Ala Ala Thr Lys Lys Leu Thr Gln
        555             560             565

GCG CAA AAT AAA TTG CAA TCG CTG GAC CCG GCT GAC CCC GGC TAT GCA    1120
Ala Gln Asn Lys Leu Gln Ser Leu Asp Pro Ala Asp Pro Gly Tyr Ala
        570             575             580

CAA GCT GAA GCC GCG GTA GAA CAG GCC GGA AAA GAA GCG ACA GAG GCG    1168
Gln Ala Glu Ala Ala Val Glu Gln Ala Gly Lys Glu Ala Thr Glu Ala
585             590             595             600

AAA GAG GCC TTA GAT AAG GCC ACG GAT GCG ACG GTT AAA GCA GGC ACA    1216
Lys Glu Ala Leu Asp Lys Ala Thr Asp Ala Thr Val Lys Ala Gly Thr
            605             610             615

GAC GCC AAA GCG AAA GCC GAG AAA GCG GAT AAC ATT CTG ACC AAA TTC    1264
Asp Ala Lys Ala Lys Ala Glu Lys Ala Asp Asn Ile Leu Thr Lys Phe
        620             625             630

CAG GGA ACG GCT AAT GCC GCC TCT CAG AAT CAG GTT TCC CAG GGT GAG    1312
Gln Gly Thr Ala Asn Ala Ala Ser Gln Asn Gln Val Ser Gln Gly Glu
        635             640             645

CAG GAT AAT CTG TCA AAT GTC GCC CGC CTC ACT ATG CTC ATG GCC ATG    1360
Gln Asp Asn Leu Ser Asn Val Ala Arg Leu Thr Met Leu Met Ala Met
        650             655             660

TTT ATT GAG ATT GTG GGC AAA AAT ACG GAA GAA AGC CTG CAA AAC GAT    1408
Phe Ile Glu Ile Val Gly Lys Asn Thr Glu Glu Ser Leu Gln Asn Asp
665             670             675             680

CTT GCG CTT TTC AAC GCC TTG CAG GAA GGG CGT CAG GCG GAG ATG GAA    1456
Leu Ala Leu Phe Asn Ala Leu Gln Glu Gly Arg Gln Ala Glu Met Glu
            685             690             695

AAG AAA TCG GCT GAA TTC CAG GAA GAG ACG CGC AAA GCC GAG GAA ACG    1504
Lys Lys Ser Ala Glu Phe Gln Glu Glu Thr Arg Lys Ala Glu Glu Thr
        700             705             710

AAC CGC ATT ATG GGA TGT ATC GGG AAA GTC CTC GGC GCG CTG CTA ACC    1552
Asn Arg Ile Met Gly Cys Ile Gly Lys Val Leu Gly Ala Leu Leu Thr
        715             720             725

ATT GTC AGC GTT GTG GCC GCT GTT TTT ACC GGT GGG GCG AGT CTG GCG    1600
Ile Val Ser Val Val Ala Ala Val Phe Thr Gly Gly Ala Ser Leu Ala
        730             735             740

CTG GCT GCG GTG GGA CTT GCG GTA ATG GTG GCC GAT GAA ATT GTG AAG    1648
Leu Ala Ala Val Gly Leu Ala Val Met Val Ala Asp Glu Ile Val Lys
```

-continued

| | | | |
|---|---|---|---|
| 745 | 750 | 755 | 760 |

| | |
|---|---|
| GCG GCG ACG GGA GTG TCG TTT ATT CAG CAG GCG CTA AAC CCG ATT ATG<br>Ala Ala Thr Gly Val Ser Phe Ile Gln Gln Ala Leu Asn Pro Ile Met<br>  765              770              775 | 1696 |
| GAG CAT GTG CTG AAG CCG TTA ATG GAG CTG ATT GGC AAG GCG ATT ACC<br>Glu His Val Leu Lys Pro Leu Met Glu Leu Ile Gly Lys Ala Ile Thr<br>           780              785              790 | 1744 |
| AAA GCG CTG GAA GGA TTA GGC GTC GAT AAG AAA ACG GCA GAG ATG GCC<br>Lys Ala Leu Glu Gly Leu Gly Val Asp Lys Lys Thr Ala Glu Met Ala<br>      795              800              805 | 1792 |
| GGC AGC ATT GTT GGT GCG ATT GTC GCC GCT ATT GCC ATG GTG GCG GTC<br>Gly Ser Ile Val Gly Ala Ile Val Ala Ala Ile Ala Met Val Ala Val<br>  810              815              820 | 1840 |
| ATT GTG GTG GTC GCA GTT GTC GGG AAA GGC GCG GCG GCG AAA CTG GGT<br>Ile Val Val Val Ala Val Val Gly Lys Gly Ala Ala Lys Leu Gly<br>825              830              835              840 | 1888 |
| AAC GCG CTG AGC AAA ATG ATG GGC GAA ACG ATT AAG AAG TTG GTG CCT<br>Asn Ala Leu Ser Lys Met Met Gly Glu Thr Ile Lys Lys Leu Val Pro<br>           845              850              855 | 1936 |
| AAC GTG CTG AAA CAG TTG GCG CAA AAC GGC AGC AAA CTC TTT ACC CAG<br>Asn Val Leu Lys Gln Leu Ala Gln Asn Gly Ser Lys Leu Phe Thr Gln<br>      860              865              870 | 1984 |
| GGG ATG CAA CGT ATT ACT AGC GGT CTG GGT AAT GTG GGT AGC AAG ATG<br>Gly Met Gln Arg Ile Thr Ser Gly Leu Gly Asn Val Gly Ser Lys Met<br>  875              880              885 | 2032 |
| GGC CTG CAA ACG AAT GCC TTA AGT AAA GAG CTG GTA GGT AAT ACC CTA<br>Gly Leu Gln Thr Asn Ala Leu Ser Lys Glu Leu Val Gly Asn Thr Leu<br>           890              895              900 | 2080 |
| AAT AAA GTG GCG TTG GGC ATG GAA GTC ACG AAT ACC GCA GCC CAG TCA<br>Asn Lys Val Ala Leu Gly Met Glu Val Thr Asn Thr Ala Ala Gln Ser<br>905              910              915              920 | 2128 |
| GCC GGT GGT GTT GCC GAG GGC GTA TTT ATT AAA AAT GCC AGC GAG GCG<br>Ala Gly Gly Val Ala Glu Gly Val Phe Ile Lys Asn Ala Ser Glu Ala<br>           925              930              935 | 2176 |
| CTT GCT GAT TTT ATG CTC GCC CGT TTT GCC ATG GAT CAG ATT CAG CAG<br>Leu Ala Asp Phe Met Leu Ala Arg Phe Ala Met Asp Gln Ile Gln Gln<br>           940              945              950 | 2224 |
| TGG CTT AAA CAA TCC GTA GAA ATA TTT GGT GAA AAC CAG AAG GTA ACG<br>Trp Leu Lys Gln Ser Val Glu Ile Phe Gly Glu Asn Gln Lys Val Thr<br>      955              960              965 | 2272 |
| GCG GAA CTG CAA AAA GCC ATG TCT TCT GCG GTA CAG CAA AAT GCG GAT<br>Ala Glu Leu Gln Lys Ala Met Ser Ser Ala Val Gln Gln Asn Ala Asp<br>  970              975              980 | 2320 |
| GCT TCG CGT TTT ATT CTG CGC CAG AGT CGC GCA TAA AAACTGCCAA<br>Ala Ser Arg Phe Ile Leu Arg Gln Ser Arg Ala  *<br>985              990              995 | 2366 |
| AATAAAGGGA GAAAAATATG TTAATTAGTA ATGTGGGAAT AAATCCCGCC GCTTATTTAA | 2426 |
| ATAATCATTC TGTTGAGAAT AGTTCACAGA CAGCTTCGCA ATCCGTTAGC GCTAAAGATA | 2486 |
| TTCTGAATAG TATTGGTATT AGCAGCAGTA AAGTCAGTGA CCTGGGGTTG AGTCCTACAC | 2546 |
| TGAGCGCGCC TGCGCCAGGG GTATTAACGC AAACCCCCGG AACGATCACG TCCTCTTTAA | 2606 |
| AAGCCAGTAT TCAAAATACC GACATGAATC AGGATTTGAA TGCTCTGGCA AATAATGTCA | 2666 |
| CGACTAAAGC GAATGAGGTT GTGCAAACCC AGTTACGCGA GCAGCAGGCA GAAGTCGGAA | 2726 |
| AGTTTTTTGA TATTAGCGGA ATGTCTTCCA GTGCCGTTGC GCTGTTGGCT GCCGCGAATA | 2786 |
| CGTTAATGCT GACGTTGAAC CAGGCTGATA GCAAACTGTC TGGTAAGTTG TCATTAGTCA | 2846 |
| GTTTTGATGC AGCTAAAACG ACGGCAAGCT CCATGATGCG CGAAGGGATG AATGCGTTGT | 2906 |

-continued

```
CCGGTAGTAT TTCCCAGAGC GCGCTTCAGT TGGGGATCAC TGGCGTGGGC GCCAAACTGG      2966

AATATAAGGG GCTGCAGAAT GAAAGAGGCG CGCTTAAACA TAATGCCGCG AAGATCGATA      3026

AACTGACCAC TGAAAGCCAC AGTATTAAAA ACGTGCTGAA CGGGCAGAAT AGCGTCAAAC      3086

TCGGTGCTGA AGGCGTCGAT TCTCTGAAAT CGTTAAATAT AAGAAAACCG GTACCGATGC      3146

GACGAAAAAT CTTAATGATG CGACGCTTAA ATCTAATGCC GGAACCAGCG CCACGGAAAG      3206

TCTGGGTATT AAAGACAGTA ATAAACAAAG TCTCCCTGAA CATCTATATC TTGTCGAAAC      3266

GTCTTGAGTC TGTCGAATCC GATATTCGTC TTGAGCAGAA TTACATGGAT ATTACCCGAA      3326

TCGATAGCGC GCAAGATGCA GATGACGGGC GATCTGATTA TGAAGAACTC GGTCACGGTC      3386

GGTGGTATTG CAGGGGCGTC CGGGCAGTAC GCCGCTACTC AGGTAACGTT TCCGAGCAGC      3446

AAATTAGCCA GGTGAATAAC CGGGTTGCCA GCACCGCATC GGACGAAGCC CGTGAAAGTT      3506

CACGTAAATC GACCAGCCTG ATTCAGGAAA TGCTGAAAAC AATGGAGAGC ATTAACCAGT      3566

CGAAAGCATC CGCACTCGCT GCTATCGCAG GCAATATTCG CGCTTAATCT GAAAGG         3622
```

(2) INFORMATION FOR SEQ ID NO:8:

(i) SEQUENCE CHARACTERISTICS:
        (A) LENGTH: 593 amino acids
        (B) TYPE: amino acid
        (D) TOPOLOGY: linear (ii) MOLECULE TYPE: protein (xi) SEQUENCE DESCRIPTION: SEQ ID NO:8:

```
Met Val Asn Asp Ala Ser Ser Ile Ser Arg Ser Gly Tyr Thr Gln Asn
 1               5                  10                  15

Pro Arg Leu Ala Glu Ala Ala Phe Glu Gly Val Arg Lys Asn Thr Asp
            20                  25                  30

Phe Leu Lys Ala Ala Asp Lys Ala Phe Lys Asp Val Val Ala Thr Lys
        35                  40                  45

Ala Gly Asp Leu Lys Ala Gly Thr Lys Ser Gly Glu Ser Ala Ile Asn
    50                  55                  60

Thr Val Gly Leu Lys Pro Pro Thr Asp Ala Ala Arg Glu Lys Leu Ser
65                  70                  75                  80

Ser Glu Gly Gln Leu Thr Leu Leu Gly Lys Leu Met Thr Leu Leu
                85                  90                  95

Gly Asp Val Ser Leu Ser Gln Leu Glu Ser Arg Leu Ala Val Trp Gln
                100                 105                 110

Ala Met Ile Glu Ser Gln Lys Glu Met Gly Ile Gln Val Ser Lys Glu
            115                 120                 125

Phe Gln Thr Ala Leu Gly Glu Ala Gln Glu Ala Thr Asp Leu Tyr Glu
        130                 135                 140

Ala Ser Ile Lys Lys Thr Asp Thr Ala Lys Ser Val Tyr Asp Ala Ala
145                 150                 155                 160

Thr Lys Lys Leu Thr Gln Ala Gln Asn Lys Leu Gln Ser Leu Asp Pro
                165                 170                 175

Ala Asp Pro Gly Tyr Ala Gln Ala Glu Ala Val Glu Gln Ala Gly
            180                 185                 190

Lys Glu Ala Thr Glu Ala Lys Glu Ala Leu Asp Lys Ala Thr Asp Ala
        195                 200                 205

Thr Val Lys Ala Gly Thr Asp Ala Lys Ala Lys Ala Glu Lys Ala Asp
    210                 215                 220

Asn Ile Leu Thr Lys Phe Gln Gly Thr Ala Asn Ala Ala Ser Gln Asn
225                 230                 235                 240
```

Gln Val Ser Gln Gly Glu Gln Asp Asn Leu Ser Asn Val Ala Arg Leu
                245                 250                 255

Thr Met Leu Met Ala Met Phe Ile Glu Ile Val Gly Lys Asn Thr Glu
            260                 265                 270

Glu Ser Leu Gln Asn Asp Leu Ala Leu Phe Asn Ala Leu Gln Glu Gly
        275                 280                 285

Arg Gln Ala Glu Met Glu Lys Lys Ser Ala Glu Phe Gln Glu Glu Thr
    290                 295                 300

Arg Lys Ala Glu Glu Thr Asn Arg Ile Met Gly Cys Ile Gly Lys Val
305                 310                 315                 320

Leu Gly Ala Leu Leu Thr Ile Val Ser Val Ala Ala Val Phe Thr
                325                 330                 335

Gly Gly Ala Ser Leu Ala Leu Ala Ala Val Gly Leu Ala Val Met Val
                340                 345                 350

Ala Asp Glu Ile Val Lys Ala Ala Thr Gly Val Ser Phe Ile Gln Gln
                355                 360                 365

Ala Leu Asn Pro Ile Met Glu His Val Leu Lys Pro Leu Met Glu Leu
        370                 375                 380

Ile Gly Lys Ala Ile Thr Lys Ala Leu Glu Gly Leu Gly Val Asp Lys
385                 390                 395                 400

Lys Thr Ala Glu Met Ala Gly Ser Ile Val Gly Ala Ile Val Ala Ala
                405                 410                 415

Ile Ala Met Val Ala Val Ile Val Val Ala Val Val Gly Lys Gly
                420                 425                 430

Ala Ala Ala Lys Leu Gly Asn Ala Leu Ser Lys Met Met Gly Glu Thr
            435                 440                 445

Ile Lys Lys Leu Val Pro Asn Val Leu Lys Gln Leu Ala Gln Asn Gly
    450                 455                 460

Ser Lys Leu Phe Thr Gln Gly Met Gln Arg Ile Thr Ser Gly Leu Gly
465                 470                 475                 480

Asn Val Gly Ser Lys Met Gly Leu Gln Thr Asn Ala Leu Ser Lys Glu
                485                 490                 495

Leu Val Gly Asn Thr Leu Asn Lys Val Ala Leu Gly Met Glu Val Thr
                500                 505                 510

Asn Thr Ala Ala Gln Ser Ala Gly Gly Val Ala Glu Gly Val Phe Ile
            515                 520                 525

Lys Asn Ala Ser Glu Ala Leu Ala Asp Phe Met Leu Ala Arg Phe Ala
    530                 535                 540

Met Asp Gln Ile Gln Gln Trp Leu Lys Gln Ser Val Glu Ile Phe Gly
545                 550                 555                 560

Glu Asn Gln Lys Val Thr Ala Glu Leu Gln Lys Ala Met Ser Ser Ala
                565                 570                 575

Val Gln Gln Asn Ala Asp Ala Ser Arg Phe Ile Leu Arg Gln Ser Arg
            580                 585                 590

Ala (2) INFORMATION FOR SEQ ID NO:9:

(i) SEQUENCE CHARACTERISTICS:
        (A) LENGTH: 5393 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
    (A) ORGANISM: Salmonella typhi
    (B) STRAIN: Ty2

(ix) FEATURE:
    (A) NAME/KEY: CDS
    (B) LOCATION: 543..2324
    (D) OTHER INFORMATION: /gene= "sipB"

(xi) SEQUENCE DESCRIPTION: SEQ ID NO:9:

```
GTTAAGTTCT ACAAAGTCGG TGACAGATAA CAGGAGTAAG TAATGGATTA TCAAATAAT      60

GTCAGCGAAG AACGTGTTGC GGAAATGATT TGGGATGCCG TTAGTGAAGG CGCCACGCTA     120

AAAGACGTTC ACGGGATCCC TCAAGATATG ATGGACGGTT TATATGCTCA TGCTTATGAG     180

TTTTATAACC AGGGACGACT GGATGAAGCT GAGACATTCT TTCGTTTCTT ATGCATTTAT     240

GATTTTTACA ATCCCGATTA CACCATGGGA CTGGCGGCGG TATGCCAACT GAAAAAACAA     300

TTTCAGAAAG CATGTGACCT TTATGCAGTA GCGTTTACGT TACTTAAAAA TGATTATCGC     360

CCCGTTTTTT TTACCGGGCA GTGTCAATTA TTAATGCGTA AGGCGGCAAA AGCCAGACAG     420

TGTTTTGAAC TTGTCAATGA ACGTACTGAA GATGAGTCTC TGCGGGCAAA AGCGTTGGTC     480

TATCTGGAGG CGCTAAAAAC GGCGGAGACA GAGCAGCACA GTGAACAAGA AAAGGAATAA     540
```

```
TT ATG GTA AAT GAC GCA AGT AGC ATT AGC CGT AGC GGA TAT ACC CAA       587
   Met Val Asn Asp Ala Ser Ser Ile Ser Arg Ser Gly Tyr Thr Gln
   595             600                 605

AAT CCG CGC CTC GCT GAG GCG GCT TTT GAA GGC GTT CGT AAG AAC ACG       635
Asn Pro Arg Leu Ala Glu Ala Ala Phe Glu Gly Val Arg Lys Asn Thr
610             615                 620                 625

GAC TTT TTA AAA GCG GCG GAT AAA GCT TTT AAA GAT GTG GTG GCA ACG       683
Asp Phe Leu Lys Ala Ala Asp Lys Ala Phe Lys Asp Val Val Ala Thr
                630                 635                 640

AAA GCG GGC GAC CTT AAA GCC GGA ACA AAG TCC GGC GAG AGC GCT ATT       731
Lys Ala Gly Asp Leu Lys Ala Gly Thr Lys Ser Gly Glu Ser Ala Ile
                645                 650                 655

AAT ACG GTG GGT CTA AAG CCG CCT ACG GAC GCC GCC CGG GAA AAA CTC       779
Asn Thr Val Gly Leu Lys Pro Pro Thr Asp Ala Ala Arg Glu Lys Leu
            660                 665                 670

TCC AGC GAA GGG CAA TTG ACA TTA CTG CTT GGC AAG TTA ATG ACA CTA       827
Ser Ser Glu Gly Gln Leu Thr Leu Leu Leu Gly Lys Leu Met Thr Leu
675                 680                 685

CTG GGC GAT GTT TCG CTG TCT CAA CTG GAG TCT CGT CTG GCG GTA TGG       875
Leu Gly Asp Val Ser Leu Ser Gln Leu Glu Ser Arg Leu Ala Val Trp
690                 695                 700                 705

CAG GCG ATG ATT GAG TCA CAA AAA GAG ATG GGG ATT CAG GTA TCG AAA       923
Gln Ala Met Ile Glu Ser Gln Lys Glu Met Gly Ile Gln Val Ser Lys
                710                 715                 720

GAA TTC CAG ACG GCT CTG GGA GAG GCT CAG GAG GCG ACG GAT CTC TAT       971
Glu Phe Gln Thr Ala Leu Gly Glu Ala Gln Glu Ala Thr Asp Leu Tyr
                725                 730                 735

GAA GCC AGC ATC AAA AAG ACG GAT ACC GCC AAG AGT GTT TAT GAC GCT      1019
Glu Ala Ser Ile Lys Lys Thr Asp Thr Ala Lys Ser Val Tyr Asp Ala
                740                 745                 750

GCG GCC AAA AAA CTG ACG CAG GCG CAA AAT AAA TTG CAA TCG CTG GAC      1067
Ala Ala Lys Lys Leu Thr Gln Ala Gln Asn Lys Leu Gln Ser Leu Asp
755                 760                 765

CCA GCT GAC CCC GGC TAT GCA CAA GCT GAA GCC GCG GTA GAA CAG GCC      1115
Pro Ala Asp Pro Gly Tyr Ala Gln Ala Glu Ala Ala Val Glu Gln Ala
770                 775                 780                 785

GGA AAA GAA GCG ACA GAG GCG AAA GAG GCC TTA GAT AAG GCC ACG GAT      1163
Gly Lys Glu Ala Thr Glu Ala Lys Glu Ala Leu Asp Lys Ala Thr Asp
                790                 795                 800
```

```
GCG ACG GTT AAA GCA GGC ACA GAC GCC AAA GCG AAA GCC GAG AAA GCG         1211
Ala Thr Val Lys Ala Gly Thr Asp Ala Lys Ala Lys Ala Glu Lys Ala
            805                 810                 815

GAT AAC ATT CTG ACC AAA TTC CAG GGA ACG GCT AAT GCC GCC TCT CAG         1259
Asp Asn Ile Leu Thr Lys Phe Gln Gly Thr Ala Asn Ala Ala Ser Gln
            820                 825                 830

AAT CAG GTT TCC CAG GGT GAG CAG GAT AAT CTG TCA AAT GTC GCC CGC         1307
Asn Gln Val Ser Gln Gly Glu Gln Asp Asn Leu Ser Asn Val Ala Arg
835                 840                 845

CTC ACT ATG CTC ATG GCC ATG TTT ATT GAG ATT GTG GGC AAA AAT ACG         1355
Leu Thr Met Leu Met Ala Met Phe Ile Glu Ile Val Gly Lys Asn Thr
850                 855                 860                 865

GAA GAA AGC CTG CAA AAC GAT CTT GCG CTT TTC AAC GCC TTG CAG GAA         1403
Glu Glu Ser Leu Gln Asn Asp Leu Ala Leu Phe Asn Ala Leu Gln Glu
            870                 875                 880

GGG CGT CAG GCG GAG ATG GAA AAG AAA TCG GCT GAA TTC CAG GAA GAG         1451
Gly Arg Gln Ala Glu Met Glu Lys Lys Ser Ala Glu Phe Gln Glu Glu
            885                 890                 895

ACG CGC AAA GCC GAG GAA ACG AAC CGC ATT ATG GGA TGT ATC GGG AAA         1499
Thr Arg Lys Ala Glu Glu Thr Asn Arg Ile Met Gly Cys Ile Gly Lys
            900                 905                 910

GTC CTC GGC GCG CTG CTA ACC ATT GTC AGC GTT GTG GCC GCT GTT TTT         1547
Val Leu Gly Ala Leu Leu Thr Ile Val Ser Val Val Ala Ala Val Phe
915                 920                 925

ACC GGT GGG GCG AGT CTG GCG CTG GCT GCG GTG GGA CTT GCG GTA ATG         1595
Thr Gly Gly Ala Ser Leu Ala Leu Ala Ala Val Gly Leu Ala Val Met
930                 935                 940                 945

GTG GCC GAT GAA ATT GTG AAG GCG GCG ACG GGG GTG TCG TTT ATT CAG         1643
Val Ala Asp Glu Ile Val Lys Ala Ala Thr Gly Val Ser Phe Ile Gln
            950                 955                 960

CAG GCG CTA AAC CCG ATT ATG GAG CAT GTG CTG AAG CCG TTA ATG GAG         1691
Gln Ala Leu Asn Pro Ile Met Glu His Val Leu Lys Pro Leu Met Glu
            965                 970                 975

CTG ATT GGC AAG GCG ATT ACC AAA GCG CTG GAA GGA TTA GGC GTC GAT         1739
Leu Ile Gly Lys Ala Ile Thr Lys Ala Leu Glu Gly Leu Gly Val Asp
            980                 985                 990

AAG AAA ACG GCA GAG ATG GCA GGC AGC ATT GTT GGT GCG ATT GTC GCC         1787
Lys Lys Thr Ala Glu Met Ala Gly Ser Ile Val Gly Ala Ile Val Ala
995                 1000                1005

GCT ATT GCC ATG GTA GCG GTC ATT GTG GTG GTC GCA GTT GTC GGG AAA         1835
Ala Ile Ala Met Val Ala Val Ile Val Val Val Ala Val Val Gly Lys
1010                1015                1020                1025

GGC GCG GCG GCG AAA CTG GGT AAC GCG CTG AGC AAA ATG ATG GGC GAA         1883
Gly Ala Ala Ala Lys Leu Gly Asn Ala Leu Ser Lys Met Met Gly Glu
                1030                1035                1040

ACG ATT AAG AAG TTG GTG CCT AAC GTG CTG AAA CAG TTG GCA CAA AAC         1931
Thr Ile Lys Lys Leu Val Pro Asn Val Leu Lys Gln Leu Ala Gln Asn
                1045                1050                1055

GGC AGC AAA CTC TTT ACC CAG GGG ATG CAA CGT ATT ACT AGC GGC CTG         1979
Gly Ser Lys Leu Phe Thr Gln Gly Met Gln Arg Ile Thr Ser Gly Leu
                1060                1065                1070

GGT AAT GTG GGT AGC AAG ATG GGC CTG CAA ACG AAT GCC TTA AGT AAA         2027
Gly Asn Val Gly Ser Lys Met Gly Leu Gln Thr Asn Ala Leu Ser Lys
    1075                1080                1085

GAG CTG GTA GGT AAT ACC CTA AAT AAA GTG GCG TTG GGC ATG GAA GTC         2075
Glu Leu Val Gly Asn Thr Leu Asn Lys Val Ala Leu Gly Met Glu Val
1090                1095                1100                1105

ACG AAT ACC GCA GCC CAG TCA GCC GGT GGG GTT GCC GAG GGG GTA TTT         2123
Thr Asn Thr Ala Ala Gln Ser Ala Gly Gly Val Ala Glu Gly Val Phe
                1110                1115                1120
```

```
ATT AAA AAT GCC AGC GAG GCG CTT GCT GAT TTT ATG CTC GCC CGT TTT      2171
Ile Lys Asn Ala Ser Glu Ala Leu Ala Asp Phe Met Leu Ala Arg Phe
        1125                1130                1135

GCC ATG GAT CAG ATT CAG CAG TGG CTT AAA CAA TCC GTA GAA ATA TTT      2219
Ala Met Asp Gln Ile Gln Gln Trp Leu Lys Gln Ser Val Glu Ile Phe
        1140                1145                1150

GGT GAA AAC CAG AAG GTA ACG GCG GAA CTG CAA AAA GCC ATG TCT TCT      2267
Gly Glu Asn Gln Lys Val Thr Ala Glu Leu Gln Lys Ala Met Ser Ser
        1155                1160                1165

GCG GTA CAG CAA AAT GCG GAT GCT TCG CGT TTT ATT CTG CGC CAG AGT      2315
Ala Val Gln Gln Asn Ala Asp Ala Ser Arg Phe Ile Leu Arg Gln Ser
1170                1175                1180                1185

CGC GCA TAA AAACTGCCAA AATAAAGGGA GAAAAATATG TTAATTAGTA              2364
Arg Ala  *

ATGTGGGAAT AAATCCCGCC GCTTATTTAA ATAATCATTC TGTTGAGAAT AGTTCACAGA    2424

CAGCTTCGCA ATCCGTTAGC GCTAAAGATA TTCTGAATAG TATTGGTATT AGCAGCAGTA    2484

AAGTCAGTGA CCTGGGGTTG AGTCCTACAC TGAGCGCGCC TGCGCCAGGG GTATTAACGC    2544

AAACCCCCGG AACGATCACG TCCTTTTTAA AAGCCAGTAT TCAAAATACC GACATGAATC    2604

AGGATTTGAA TGCCCTGGCA AATAATGTCA CGACTAAAGC GAATGAGGTT GTGCAAACCC    2664

AGTTACGCGA GCAGCAGGCA GAAGTCGGAA AGTTTTTTGA TATTAGCGGA ATGTCTTCCA    2724

GTGCCGTTGC GCTGTTGGCT GCCGCGAATA CGTTAATGCT GACGTTGAAC CAGGCTGATA    2784

GCAAACTGTC TGGTAAGTTG TCATTAGTCA GTTTTGATGC AGCTAAAACG ACGGCAAGCT    2844

CCATGATGCG CGAAGGGATG AATGCGTTGT CCGGTAGTAT TTCCCAGAGC GCGCTTCAGT    2904

TGGGGATCAC TGGCGTGGGC GCCAAACTGG AATATAAGGG GCTGCAGAAT GAAAGAGGCG    2964

CGCTTAAACA TAATGCCGCG AAGATCGATA AACTGACCAC TGAAAGCCAC AGTATTAAAA    3024

ACGTGCTGAA CGGGCAGAAT AGCGTCAAAC TTGGTGCTGA AGGCGTCGAT TCTCTGAAAT    3084

CGTTAAAATAT GAAGAAAACC GGTACCGATG CGACGAAAAA TCTTAATGAT GCGACGCTTA   3144

AATCTAATGC CGGAACCAGC GCCACGGAAA GTCTGGGTAT TAAAAACAGT AATAAACAAA    3204

TCTCCCCTGA ACATCAGGCT ATTCTGTCGA AACGTCTTGA GTCTGTCGAA TCCGATATTC    3264

GTCTTGAGCA GAATACCATG GATATGACCC GAATCGATGC GCGCAAGATG CAGATGACGG    3324

GCGATCTGAT TATGAAGAAC TCAGTCACGG TCGGTGGTAT TGCAGGGGCG TCCAGGCAGT    3384

ACGCCGCTAC TCAGGAACGT TCCGAGCAGC AAATTAGCCA GGTGAATAAC CGGGTTGCCA    3444

GCACCGCATC GGACGAAGCC CGTGAAAGTT CACGTAAATC GACCAGCCTG ATTCAGGAAA    3504

TGCTGAAAAC AATGGAGAGC ATTAACCAGT CGAAAGCATC CGCACTCGCT GCTATCGCAG    3564

GCAATATTCG CGCTTAATCT GACAGATCAA CTATACGCCA TCAGGGGGGG ATTTAATCGC    3624

CCTCCTGATG GCGAACTGGG GATATTATGC TTAATATTCA AAATTATTCC GCTTCTCCTC    3684

ATCCGGGGAT CGTTGCCGAA CGGCCGCAGA CTCCTTCGGC GAGCGAGCAC GCCGAGATTG    3744

CCGTGGTACC GTCTACCACA GAACATCGCG GCACAGATAT CATTTCATTA TCGCAGGCGG    3804

CTACTAAAAT CCAGCAGGCA CAGCAGACGC TGCAGTCAAC GCCACCGATT TCTGAAGAGA    3864

ATAATGACGA GCGCACGCTG GCGCGCCAAC AGTTGACCAG CAGCCTGAAT GCGCTGGCGA    3924

AGTCCGGCGT GTCATTATCC GCAGAACAAA ATGAGAACCT GCGGAGCACG TTTTCTGCGC    3984

GACGTCGGCC TTATTTAGCG CTTCGCCTAT GGCCAGCGAG AACAACCATT TCTGATGCTG    4044

AGATTTGGGA TATGGTTTCC CAAAATATAT CGGCGATAGG TGACAGCTAC CTGGGCGTTT    4104

ATGAAAACGT TGTCGCAGTC TATACCGATT TTTATCAGGC CTTCAGTGAT ATTCTTTCCA    4164
```

```
AAATGGGAGG CTGGTTATCG CCTGGTAAGG ATGGAAATAC CATTAAGCTA AATGTTGACT    4224

CACTTAAAAG TGAAATAAGT AGTTTAATTA ATAAATACAC TCAAATAAAT AAAAATACGA    4284

TTTTATTTCC CTCGCAAACT GGCAGCGGAA TGACAACAGC AACGAAAGCG GAAGCTGAGC    4344

AGTGGATTAA AGAATTGAAT TTACCGGACA GCTGTCTAAA GGCGTCTGGT TCTGGTTATG    4404

TCGTACTGGT GGATACGGGG CCACTGAGCA AATGGTTAG CGATCTTAAT GGAATAGGAT     4464

CGGGTTCAGC CCTTGAACTG GATAACGCCA AATATCAAGC CTGGCAGTCG GGTTTTAAAG    4524

CACAGGAAGA AAATCTGAAA ACCACATTAC AGACGCTGAC GCAAAAATAT AGCAATGCCA    4584

ATTCATTGTA CGACAACCTG GTAAAAGTGC TGAGCAGTAC GATAAGTAGC AGCCTGGAAA    4644

CCGCCAAAAG CTTCCTGCAA GGATAACAGA GAGGATATT AATAATGGTT ACAAGTGTAA      4704

GAACTCAGCC CCCCGTCATA ATGCCAGGTA TGCAGACCGA GATCAAAACG CAGGCCACGA    4764

ATCTTGCGGC GAATCTTTCC GCGGTCAGAG AAAGTGCCAC AGCAACGCTG TCAGGGGAAA    4824

TTAAAGGCCA GCAACTGGAA GATTTTCCCG CGCTGATCAA ACAGGCGAGT CTGGATGCGT    4884

TGTTTAAATG CGGGAAAGAC GCCGAGGCGT TAAAAGAAGT TTTTACCAAT TCAAATAATG    4944

TCGCCGGTAA GAAAGCGATA ATGGAGTTTG CCGGCCTCTT TCGTTCAGCG CTCAACGCCA    5004

CCAGTGATTC TCCTGAGGCG AAGACGCTAC TGATGAAGGT GGGGGCAGAG TATACCGCGC    5064

AAATCATAAA AGATGGCCTG AAAGAAAAGT CAGCTTTTGG GCCATGGCTG CCAGAAACAA    5124

AGAAAGCGGA AGCGAAGCTG GAAAACCTGG AAAAGCAGCT GTTAGATATC ATCAAAAATA    5184

ACACTGGCGG TGAATTAAGT AAATTATCGA CGAATCTTGT TATGCAGGAG GTGATGCCCT    5244

ATATTGCCAG CTGCATTGAA CATAACTTTG GCTGTACGTT AGATCCGTTA ACCCGCAGCA    5304

GTCTTACGCA GCTTGTTGAC AAAGCGGCGG CGAAGGCGGT TGAGGCGCTT GATATGTGCC    5364

ACCAAAAATT AACGCAAGAG CAGGGTACC                                     5393

(2) INFORMATION FOR SEQ ID NO:10:

(i) SEQUENCE CHARACTERISTICS:
        (A) LENGTH: 593 amino acids
        (B) TYPE: amino acid
        (D) TOPOLOGY: linear (ii) MOLECULE TYPE: protein (xi) SEQUENCE DESCRIPTION: SEQ ID NO:10:

Met Val Asn Asp Ala Ser Ser Ile Ser Arg Ser Gly Tyr Thr Gln Asn
 1               5                  10                  15

Pro Arg Leu Ala Glu Ala Ala Phe Glu Gly Val Arg Lys Asn Thr Asp
            20                  25                  30

Phe Leu Lys Ala Ala Asp Lys Ala Phe Lys Asp Val Val Ala Thr Lys
        35                  40                  45

Ala Gly Asp Leu Lys Ala Gly Thr Lys Ser Gly Glu Ser Ala Ile Asn
    50                  55                  60

Thr Val Gly Leu Lys Pro Pro Thr Asp Ala Ala Arg Glu Lys Leu Ser
65                  70                  75                  80

Ser Glu Gly Gln Leu Thr Leu Leu Gly Lys Leu Met Thr Leu Leu
                85                  90                  95

Gly Asp Val Ser Leu Ser Gln Leu Glu Ser Arg Leu Ala Val Trp Gln
                100                 105                 110

Ala Met Ile Glu Ser Gln Lys Glu Met Gly Ile Gln Val Ser Lys Glu
            115                 120                 125

Phe Gln Thr Ala Leu Gly Glu Ala Gln Glu Ala Thr Asp Leu Tyr Glu
        130                 135                 140
```

-continued

```
Ala Ser Ile Lys Lys Thr Asp Thr Ala Lys Ser Val Tyr Asp Ala Ala
145                 150                 155                 160

Ala Lys Lys Leu Thr Gln Ala Gln Asn Lys Leu Gln Ser Leu Asp Pro
            165                 170                 175

Ala Asp Pro Gly Tyr Ala Gln Ala Glu Ala Ala Val Glu Gln Ala Gly
            180                 185                 190

Lys Glu Ala Thr Glu Ala Lys Glu Ala Leu Asp Lys Ala Thr Asp Ala
        195                 200                 205

Thr Val Lys Ala Gly Thr Asp Ala Lys Ala Lys Ala Glu Lys Ala Asp
210                 215                 220

Asn Ile Leu Thr Lys Phe Gln Gly Thr Ala Asn Ala Ala Ser Gln Asn
225                 230                 235                 240

Gln Val Ser Gln Gly Glu Gln Asp Asn Leu Ser Asn Val Ala Arg Leu
            245                 250                 255

Thr Met Leu Met Ala Met Phe Ile Glu Ile Val Gly Lys Asn Thr Glu
            260                 265                 270

Glu Ser Leu Gln Asn Asp Leu Ala Leu Phe Asn Ala Leu Gln Glu Gly
        275                 280                 285

Arg Gln Ala Glu Met Glu Lys Lys Ser Ala Glu Phe Gln Glu Glu Thr
290                 295                 300

Arg Lys Ala Glu Glu Thr Asn Arg Ile Met Gly Cys Ile Gly Lys Val
305                 310                 315                 320

Leu Gly Ala Leu Leu Thr Ile Val Ser Val Ala Ala Val Phe Thr
            325                 330                 335

Gly Gly Ala Ser Leu Ala Leu Ala Ala Val Gly Leu Ala Val Met Val
            340                 345                 350

Ala Asp Glu Ile Val Lys Ala Ala Thr Gly Val Ser Phe Ile Gln Gln
        355                 360                 365

Ala Leu Asn Pro Ile Met Glu His Val Leu Lys Pro Leu Met Glu Leu
        370                 375                 380

Ile Gly Lys Ala Ile Thr Lys Ala Leu Glu Gly Leu Gly Val Asp Lys
385                 390                 395                 400

Lys Thr Ala Glu Met Ala Gly Ser Ile Val Gly Ala Ile Val Ala Ala
            405                 410                 415

Ile Ala Met Val Ala Val Ile Val Val Ala Val Val Gly Lys Gly
            420                 425                 430

Ala Ala Ala Lys Leu Gly Asn Ala Leu Ser Lys Met Met Gly Glu Thr
            435                 440                 445

Ile Lys Lys Leu Val Pro Asn Val Leu Lys Gln Leu Ala Gln Asn Gly
450                 455                 460

Ser Lys Leu Phe Thr Gln Gly Met Gln Arg Ile Thr Ser Gly Leu Gly
465                 470                 475                 480

Asn Val Gly Ser Lys Met Gly Leu Gln Thr Asn Ala Leu Ser Lys Glu
            485                 490                 495

Leu Val Gly Asn Thr Leu Asn Lys Val Ala Leu Gly Met Glu Val Thr
            500                 505                 510

Asn Thr Ala Ala Gln Ser Ala Gly Gly Val Ala Glu Gly Val Phe Ile
        515                 520                 525

Lys Asn Ala Ser Glu Ala Leu Ala Asp Phe Met Leu Ala Arg Phe Ala
        530                 535                 540

Met Asp Gln Ile Gln Gln Trp Leu Lys Gln Ser Val Glu Ile Phe Gly
545                 550                 555                 560
```

```
Glu Asn Gln Lys Val Thr Ala Glu Leu Gln Lys Ala Met Ser Ser Ala
            565                 570                 575

Val Gln Gln Asn Ala Asp Ala Ser Arg Phe Ile Leu Arg Gln Ser Arg
            580                 585                 590

Ala
```